US012545677B2

(12) United States Patent
Xu et al.

(10) Patent No.: US 12,545,677 B2

(45) Date of Patent: Feb. 10, 2026

(54) COMPOUNDS USEFUL AS FACTOR XIa INHIBITORS

(71) Applicant: JANSSEN PHARMACEUTICA NV, Beerse (BE)

(72) Inventors: Guozhang Xu, Spring House, PA (US); Mark J. Macielag, Spring House, PA (US); Zhijie Liu, Spring House, PA (US); Tho V. Thieu, Spring House, PA (US); Ravi Nargund, Spring House, PA (US)

(73) Assignee: Janssen Pharmaceutica NV, Beerse (BE)

( * ) Notice: Subject to any disclaimer, the term of this patent is extended or adjusted under 35 U.S.C. 154(b) by 483 days.

(21) Appl. No.: 18/006,261

(22) PCT Filed: Jul. 21, 2021

(86) PCT No.: PCT/EP2021/070430
§ 371 (c)(1),
(2) Date: Jan. 20, 2023

(87) PCT Pub. No.: WO2022/018156
PCT Pub. Date: Jan. 27, 2022

(65) Prior Publication Data

US 2023/0312560 A1 Oct. 5, 2023

Related U.S. Application Data

(60) Provisional application No. 63/054,826, filed on Jul. 22, 2020.

(51) Int. Cl.

| | |
|---|---|
| ***C07D 471/04*** | (2006.01) |
| ***A61P 7/02*** | (2006.01) |
| ***C07D 487/04*** | (2006.01) |
| ***C07D 519/00*** | (2006.01) |
| ***C07F 9/6561*** | (2006.01) |

(52) U.S. Cl.
CPC .............. *C07D 471/04* (2013.01); *A61P 7/02* (2018.01); *C07D 487/04* (2013.01); *C07D 519/00* (2013.01); *C07F 9/6561* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 4,808,405 | A | 2/1989 | Smith et al. |
| 4,845,079 | A | 7/1989 | Luly et al. |
| 4,885,292 | A | 12/1989 | Ryono et al. |
| 4,894,437 | A | 1/1990 | Tenbrink |
| 4,980,283 | A | 12/1990 | Huang et al. |
| 5,034,512 | A | 7/1991 | Hudspeth et al. |
| 5,036,053 | A | 7/1991 | Himmelsbach et al. |
| 5,036,054 | A | 7/1991 | Kaltenbronn et al. |
| 5,055,466 | A | 10/1991 | Weller et al. |
| 5,063,207 | A | 11/1991 | Doherty et al. |
| 5,063,208 | A | 11/1991 | Rosenberg et al. |
| 5,064,965 | A | 11/1991 | Ocain et al. |
| 5,066,643 | A | 11/1991 | Abeles et al. |
| 5,071,837 | A | 12/1991 | Doherty et al. |
| 5,075,451 | A | 12/1991 | Ocain et al. |
| 5,089,471 | A | 2/1992 | Hanson et al. |
| 5,095,119 | A | 3/1992 | Ocain et al. |
| 5,098,924 | A | 3/1992 | Poss |
| 5,104,869 | A | 4/1992 | Albright et al. |
| 5,106,835 | A | 4/1992 | Albright et al. |
| 5,114,937 | A | 5/1992 | Hamby et al. |
| 5,116,835 | A | 5/1992 | Ruger et al. |
| 6,063,847 | A | 5/2000 | Chackalamannil et al. |
| 6,326,380 | B1 | 12/2001 | Chackalamannil et al. |
| 6,645,987 | B2 | 11/2003 | Chackalamannil et al. |
| 7,037,920 | B2 | 5/2006 | Chackalamannil et al. |
| 7,235,567 | B2 | 6/2007 | Wu |
| 7,304,078 | B2 | 12/2007 | Chackalamannil et al. |
| 9,944,625 | B2 | 4/2018 | Orwat et al. |
| 2006/0154915 | A1 | 7/2006 | Corte et al. |
| 2014/0275061 | A1 | 9/2014 | Orwat et al. |
| 2016/0185773 | A1 | 6/2016 | Edwards et al. |
| 2017/0305880 | A1 | 10/2017 | Orwat et al. |
| 2017/0305917 | A1 | 10/2017 | Courtney et al. |
| 2023/0295157 | A1 | 9/2023 | Xu et al. |

FOREIGN PATENT DOCUMENTS

| | | | |
|---|---|---|---|
| EP | 0028489 | A1 | 5/1981 |
| EP | 1495028 | A1 | 1/2005 |
| EP | 1294714 | B1 | 8/2007 |

(Continued)

OTHER PUBLICATIONS

"2-[4-[2-[(3s)-7-[5-chloro-2-(Tetrazol-1-yl)phenyl]-5-oxo-2,3,8,8a-tetrahydro-ii-i-indolizin-3-a-1h-imidazol-5-Aphenynacetic Acid", PubChem, CID 146247689, pp. 1-9, Jun. 27, 2020.

(Continued)

*Primary Examiner* — Brian J Davis

(57) ABSTRACT

The present invention is directed to Factor XIa inhibitors, tautomers, stereoisomers, isotopologues, and pharmaceutically acceptable salts and solvates thereof, pharmaceutical compositions containing said compounds and the use of said compounds in the treatment and/or prophylaxis of thromboembolic disorders, inflammatory disorders, and diseases or conditions in which plasma kallikrein activity is implicated.

19 Claims, No Drawings

(56) References Cited

FOREIGN PATENT DOCUMENTS

| | | | | |
|---|---|---|---|---|
| EP | 1495018 | B1 | 11/2007 | |
| EP | 3290413 | A1 | 3/2018 | |
| JP | 2017218449 | A | 12/2017 | |
| WO | 94/03479 | A1 | 2/1994 | |
| WO | WO 01/29050 | A2 * | 4/2001 | ........... C07D 498/04 |
| WO | 01/40231 | A1 | 6/2001 | |
| WO | 01/96330 | A2 | 12/2001 | |
| WO | 03089435 | A1 | 10/2003 | |
| WO | 2009124167 | A1 | 10/2009 | |
| WO | 2013/055984 | A1 | 4/2013 | |
| WO | 2014022767 | A1 | 2/2014 | |
| WO | 2016093285 | A1 | 6/2016 | |
| WO | 2017019819 | A1 | 2/2017 | |
| WO | 2017023992 | A1 | 2/2017 | |

OTHER PUBLICATIONS

"4-[2-[(3S)-8-Bromo-7-[5-chloro-2-(tetrazol-1-yl)phenyl]-5-oxo-2,3,8,8a-tetrahydro-1H-indolizin-3-yl]-1H-imidazol-5-yl]thiophene-2-carboxylic acid", PubChem, CID 153061176, pp. 1-8, Aug. 13, 2020.

Hanessian et al., "Synthesis of Diversely Functionalized Indolizidinones and Related Bicyclic Lactams Using Intramolecular Grubbs Olefin Metathesis and Dieckmann Condensation", The Journal of Organic Chemistry, vol. 68, No. 19, pp. 7219-7233, Sep. 19, 2003.

International Search Report and Written Opinion, received for PCT Application No. PCT/EP2021/070430, mailed on Sep. 24, 2021, 13 pages.

Quan et al., "Factor Xis Inhibitors as New Anticoagulants", Journal of Medicinal Chemistry, vol. 61, pp. 7425-7447, 2018.

Xiaoyong et al., "The Antithrombin Activity Detection of Eh in Vitro", China Biotechnology, vol. 31, No. 5, pp. 108-112, 2011. (English Abstract Submitted).

Bernatowicz et al., "Development of Potent Thrombin Receptor Antagonist Peptides", J. Med. Chern., 1996, vol. 39, 4879-4887.

Gailani et al., "Intrinsic Pathway of Coagulation and Arterial Thrombosis Arterioscler", Thromb. Vase. Biol., 2007, 27, 2507-2513.

Hoffman, "A cell-based model of coagulation and the role of factor VIIa", Blood Reviews, 2003, 17, S1-S5.

Howard et al., "Factor IXa Inhibitors as Novel Anticoagulants", Arterioscler. Thromb. Vase. Biol., 2007, 27, 722-727.

Wong et al., "Nonpeptide factor Xa inhibitors III: effects of DPC423, an orally-active pyrazole antithrombotic agent, on arterial thrombosis in rabbits", J Pharmacol. Exp. Ther., 2002, vol. 303(3), 993-1000.

Xie et al., "Discovery and development of plasma kallikrein inhibitors for multiple diseases", European Journal of Medicinal Chemistry 190 (2020) 112137.

* cited by examiner

COMPOUNDS USEFUL AS FACTOR XIa INHIBITORS

CROSS-REFERENCE TO RELATED APPLICATIONS

This application is the National Stage Application of International Patent Application No. PCT/EP2021/070430, filed Jul. 21, 2021, which claims the benefit of U.S. Provisional Application No. 63/054,826, filed on Jul. 22, 2020, which is incorporated by reference herein in its entirety.

FIELD OF THE INVENTION

The present invention is directed to Factor XIa inhibitors, tautomers, stereoisomers, isotopologues, and pharmaceutically acceptable salts and solvates thereof, pharmaceutical compositions containing said compounds, and the use of said compounds in the treatment and/or prophylaxis of thromboembolic disorders, inflammatory disorders, and diseases or conditions in which plasma kallikrein activity is implicated.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the bloodstream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets.

Factor XIa, a plasma serine protease involved in the regulation of blood coagulation, is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.,* 27:2507-2513 (2007)). The resulting burst of thrombin converts fibrinogen to fibrin that polymerizes to form the structural framework of a blood clot, and activates platelets, which are a key cellular component of coagulation (Hoffman, M., *Blood Reviews,* 17:S1-S5 (2003)). Therefore, factor XIa plays a key role in propagating this amplification loop and is thus an attractive target for antithrombotic therapy.

In addition to stimulation via tissue factor, the coagulation system can be activated particularly on negatively charged surfaces, which include not only surface structures of foreign cells (e.g. bacteria) but also artificial surfaces such as vascular prostheses, stents and extracorporeal circulation. On the surface, initially factor XII (FXII) is activated to factor XIIa which subsequently activates factor XI, attached to cell surfaces, to factor XIa. This leads to further activation of the coagulation cascade as described above. In addition, factor XIIa also activates bound plasma prokallikrein to plasma kallikrein (PK) which, in a potentiation loop, leads to further factor XII activation, overall resulting in amplification of the initiation of the coagulation cascade. In addition, PK is an important bradykinin-releasing protease which leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

Thus, there remains a need for Factor XIa inhibitor compounds that have pharmacokinetic and pharmacodynamic properties suitable for use as human pharmaceuticals for the treatment and/or prophylaxis of thromboembolic disorders.

SUMMARY OF THE INVENTION

The present invention is directed to a compound of formula (I)

(I)

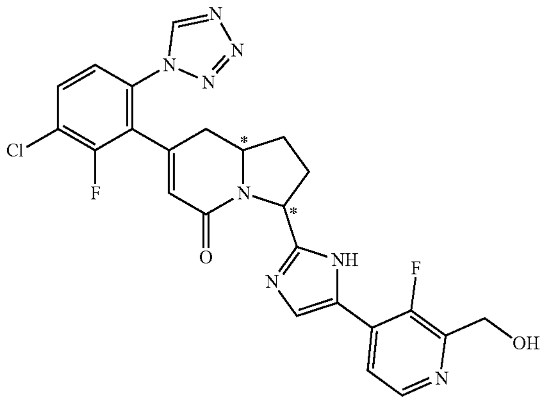

also known as 7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one, and tautomers, stereoisomers, isotopologues, and pharmaceutically acceptable salts or solvates thereof.

The present invention is further directed to a compound of formula (II)

(II)

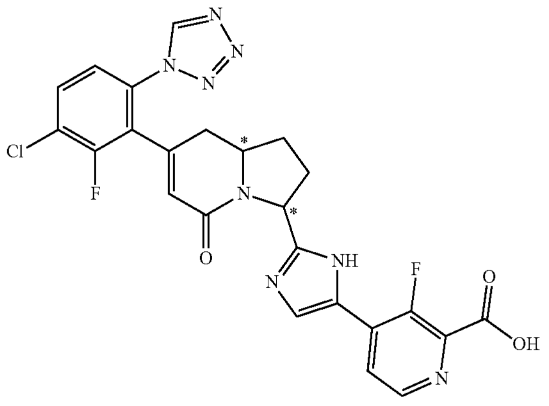

also known as 4-(2-(7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinic acid, and tautomers, stereoisomers, isotopologues, and pharmaceutically acceptable salts or solvates thereof.

The present invention is further directed to a compound of formula (III)

(III)

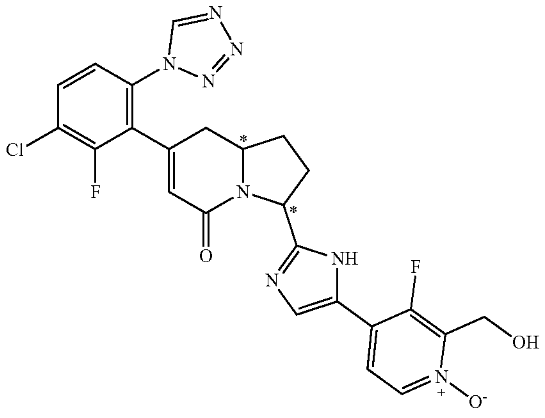

also known as 4-(2-(7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoro-2-(hydroxymethyl)pyridine 1-oxide, and tautomers, stereoisomers, isotopologues, and pharmaceutically acceptable salts or solvates thereof.

The present invention is further directed to a compound of formula (IV)

(IV)

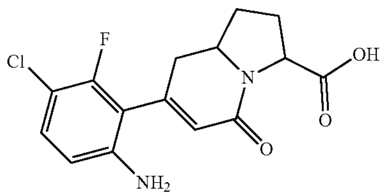

also known as 7-(6-amino-3-chloro-2-fluorophenyl)-5-oxo-1,2,3,5,8,8a-hexahydroindolizine-3-carboxylic acid, and stereoisomers, isotopologues, and salts thereof.

The present invention is further directed to a compound of formula (V)

(V)

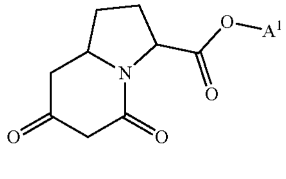

wherein $A^1$ is $C_{1-4}$alkyl, and stereoisomers, isotopologues, and salts thereof.

The present invention is further directed to a compound of formula (VI)

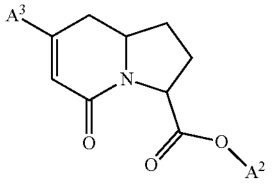

(VI)

wherein $A^2$ is $C_{1-4}$alkyl, and $A^3$ is selected from $—O—SO_2—CF_3$, $—O—SO_2—CF_2CF_2H$, or $—O—SO_2—CF_2CF_2CF_3$, and stereoisomers, isotopologues, and salts thereof.

The present invention is further directed to processes for the preparation of a compound of formula (I), compound of formula (II), a compound of formula (III), a compound of formula (IV), a compound of formula (V), or a compound of formula (VI). The present invention is further directed to a compound of formula (I), compound of formula (II), a compound of formula (III), a compound of formula (IV), a compound of formula (V), or a compound of formula (VI), prepared according to any of the process(es) described herein.

Illustrative of the invention are pharmaceutical compositions comprising a pharmaceutically acceptable carrier and a compound of formula (I), compound of formula (II), or a compound of formula (III) as described herein.

An illustration of the invention is a pharmaceutical composition made by mixing a compound of formula (I), compound of formula (II), or a compound of formula (III) as described herein and a pharmaceutically acceptable carrier. Illustrating the invention is a process for making a pharmaceutical composition comprising mixing a compound of formula (I), compound of formula (II), or a compound of formula (III) as described herein and a pharmaceutically acceptable carrier.

Exemplifying the invention are methods for the treatment and/or prophylaxis of thromboembolic disorders, inflammatory disorders or diseases or conditions in which plasma kallikrein activity is implicated, as described herein, comprising administering to a subject in need thereof a therapeutically effective amount of any of the compounds or pharmaceutical compositions described above.

Exemplifying the invention are methods for the treatment and/or prophylaxis of thromboembolic disorders, such as arterial cardiovascular thromboembolic disorders, venous cardiovascular thromboembolic disorders, arterial cerebrovascular thromboembolic disorders, and venous cerebrovascular thromboembolic disorders, comprising administering to a subject in need thereof a therapeutically effective amount of any of the compounds or pharmaceutical compositions described above. Examples of thromboembolic disorders include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In an embodiment, the present invention is directed to a compound of formula (I), compound of formula (II), or a compound of formula (III) for use as a medicament. In another embodiment, the present invention is directed to a compound of formula (I), compound of formula (II), or a compound of formula (III) for use in the treatment and/or prophylaxis of thromboembolic disorders, inflammatory disorders or diseases or conditions in which plasma kallikrein activity is implicated.

In another embodiment, the present invention is directed to a compound of formula (I), compound of formula (II), or a compound of formula (III) for use in the treatment and/or prophylaxis of a thromboembolic disorder, such as arterial cardiovascular thromboembolic disorders, venous cardiovascular thromboembolic disorders, arterial cerebrovascular thromboembolic disorders, and venous cerebrovascular thromboembolic disorders. In another embodiment, the present invention is directed to a compound of formula (I), compound of formula (II), or a compound of formula (III) for use in the treatment and/or prophylaxis of a thromboembolic disorder selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention is directed to a compound of formula (I) or a compound of formula (II) for use in the treatment and/or prophylaxis of a thromboembolic disorder selected from the group consisting of hereditary angioedema (HAE) and diabetic macular edema (DME).

In another embodiment, the present invention is directed to a composition comprising a compound of formula (I), compound of formula (II), or a compound of formula (III) for use in the treatment and/or prophylaxis of a disorder, disease or condition as described herein. In another embodiment, the present invention is directed to a composition comprising a compound of formula (I), compound of formula (II), or a compound of formula (III) for use in the treatment and/or prophylaxis of a thromboembolic disorder, an inflammatory disorder or a disease or condition in which plasma kallikrein activity is implicated.

In another embodiment, the present invention is directed to a composition comprising a compound of formula (I), compound of formula (II), or a compound of formula (III) for use in the treatment and/or prophylaxis of a thromboembolic disorder, such as arterial cardiovascular thromboembolic disorders, venous cardiovascular thromboembolic disorders, arterial cerebrovascular thromboembolic disorders, and venous cerebrovascular thromboembolic disorders. In another embodiment, the present invention is directed to a composition comprising a compound of formula (I), compound of formula (II), or a compound of formula (III) for use in the treatment and/or prophylaxis of a thromboembolic disorder selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention is directed to a composition comprising a compound of formula (I) or a compound of formula (II) for use in the treatment and/or prophylaxis of a thromboembolic disorder such as hereditary angioedema (HAE) or diabetic macular edema (DME).

Another example of the invention is the use of any of the compounds described herein in the preparation of a medicament for the treatment and/or prophylaxis of a disorder, disease or condition as described herein. Another example of the invention is the use of any of the compounds described herein in the preparation of a medicament for the treatment and/or prophylaxis of a thromboembolic disorder, an inflammatory disorder or a disease or condition in which plasma kallikrein activity is implicated.

Another example of the invention is the use of any of the compounds described herein in the preparation of a medicament for the treatment and/or prophylaxis of a thromboembolic disorder selected from the group consisting of (a) arterial cardiovascular thromboembolic disorders, (b) venous cardiovascular thromboembolic disorders, (c) arterial cerebrovascular thromboembolic disorders, and (d) venous cerebrovascular thromboembolic disorders. Another example of the invention is the use of any of the compounds described herein in the preparation of a medicament for the treatment and/or prophylaxis of (a) unstable angina, (b) an acute coronary syndrome, (c) atrial fibrillation, (d) first myocardial infarction, (e) recurrent myocardial infarction, (f) ischemic sudden death, (g) transient ischemic attack, (h) stroke, (i) atherosclerosis, (j) peripheral occlusive arterial disease, (k) venous thrombosis, (l) deep vein thrombosis, (m) thrombophlebitis, (n) arterial embolism, (o) coronary arterial thrombosis, (p) cerebral arterial thrombosis, (q) cerebral embolism, (r) kidney embolism, (s) pulmonary embolism, or (t) thrombosis resulting from medical implants, devices, or procedures in which blood is exposed to an artificial surface that promotes thrombosis. Another example of the invention is the use of any of the compounds described herein in the preparation of a medicament for the treatment and/or prophylaxis of: (a) hereditary angioedema (HAE) or (b) diabetic macular edema (DME).

Another example of the invention is the use of any of the compounds described herein in a method for treating a thromboembolic, inflammatory or a disease or condition in which plasma kallikrein activity is implicated as described herein, in a subject in need thereof.

Another example of the invention is the use of any of the compounds described herein in a method for the treatment and/or prophylaxis of (a) arterial cardiovascular thromboembolic disorders, (b) venous cardiovascular thromboembolic disorders, (c) arterial cerebrovascular thromboembolic disorders, or (d) venous cerebrovascular thromboembolic disorders, in a subject in need thereof. Another example of the invention is the use of any of the compounds described herein in a method for the treatment and/or prophylaxis of (a) unstable angina, (b) an acute coronary syndrome, (c) atrial fibrillation, (d) first myocardial infarction, (e) recurrent myocardial infarction, (f) ischemic sudden death, (g) transient ischemic attack, (h) stroke, (i) atherosclerosis, (j) peripheral occlusive arterial disease, (k) venous thrombosis, (l) deep vein thrombosis, (m) thrombophlebitis, (n) arterial embolism, (o) coronary arterial thrombosis, (p) cerebral arterial thrombosis, (q) cerebral embolism, (r) kidney embolism, (s) pulmonary embolism, or (t) thrombosis resulting from medical implants, devices, or procedures in which blood is exposed to an artificial surface that promotes thrombosis, in a subject in need thereof. Another example of the invention is the use of any of the compounds described herein in a method for the treatment and/or prophylaxis of (a) hereditary angioedema (HAE) or (b) diabetic macular edema (DME), in a subject in need thereof.

In another example, the present invention is directed to a compound as described herein, for use in a method for the treatment and/or prophylaxis of disorders, diseases or conditions as described herein, in a subject in need thereof. In another example, the present invention is directed to a compound as described herein, for use in a method for the treatment and/or prophylaxis of a thromboembolic, inflammatory disorder, or a disease or condition in which plasma kallikrein activity is implicated, as described herein, in a subject in need thereof.

In another example, the present invention is directed to a compound as described herein, for use in methods for the treatment and/or prophylaxis of a thromboembolic disorder, such as arterial cardiovascular thromboembolic disorders, venous cardiovascular thromboembolic disorders, arterial cerebrovascular thromboembolic disorders, and venous cerebrovascular thromboembolic disorders, in a subject in need thereof. In another example, the present invention is directed to a compound as described herein, for use in methods for the treatment and/or prophylaxis of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis, in a subject in need thereof. In another example, the present invention is directed to a compound as described herein, for use in a method for the treatment and/or prophylaxis of hereditary angioedema (HAE) or diabetic macular edema (DME), in a subject in need thereof.

The present invention is further directed to a compound, composition (e.g. pharmaceutical composition), method of treatment, method of preparation or use, as herein described.

DETAILED DESCRIPTION OF THE INVENTION

The present invention is directed to a compound of formula (I)

(I)

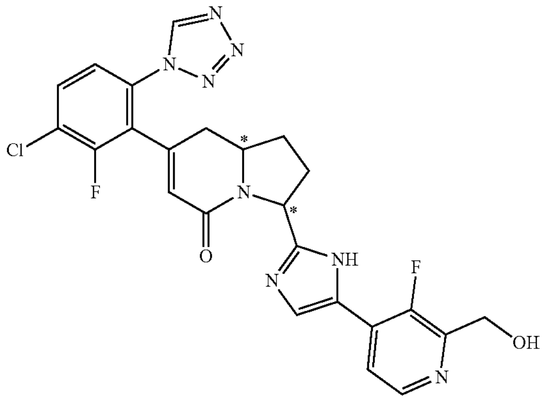

and tautomers, stereoisomers, isotopologues, and pharmaceutically acceptable salts or solvates thereof. The present invention is further directed to a compound of formula (II)

(II)

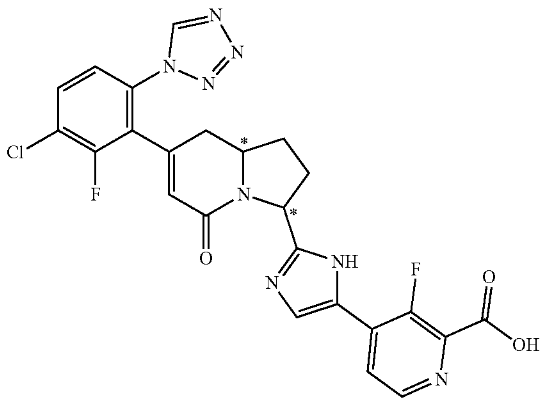

and tautomers, stereoisomers, isotopologues, and pharmaceutically acceptable salts or solvates thereof. The present invention is further directed to a compound of formula (III)

(III)

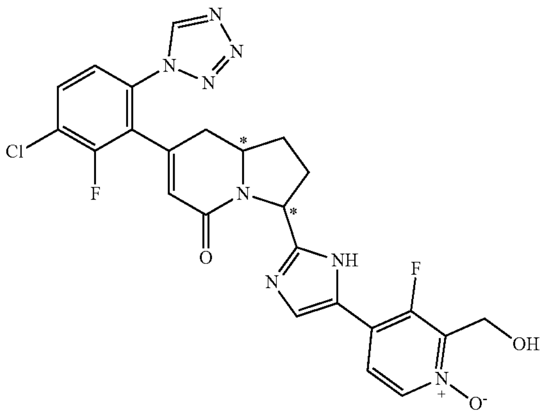

and tautomers, stereoisomers, isotopologues, and pharmaceutically acceptable salts or solvates thereof.

The compounds of formula (I), compounds of formula (II) and compounds of formula (III) of the present invention are useful for the treatment and/or prophylaxis of thromboembolic disorders, inflammatory disorders and diseases or conditions in which plasma kallikrein activity is implicated.

In certain embodiment, the present invention is directed to a compound of formula (I-A)

(I-A)

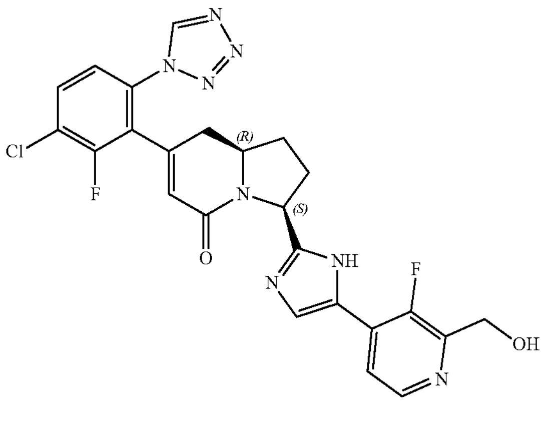

also known as (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one, and tautomers, stereoisomers, isotopologues, and pharmaceutically acceptable salts or solvates thereof.

In certain embodiments, the present invention is directed to a compound of formula (I-B)

(I-B)

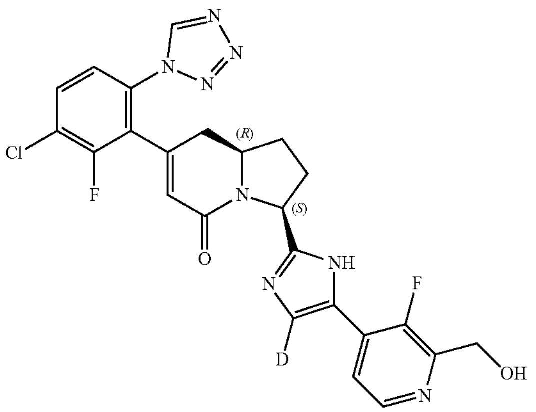

also known as (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl-4-d)-2,3,8,8a-tetrahydroindolizin-5(1H)-one and tautomers, stereoisomers, isotopologues, and pharmaceutically acceptable salts or solvates thereof.

In certain embodiments, the present invention is directed to a compound of formula (I-C)

(I-C)

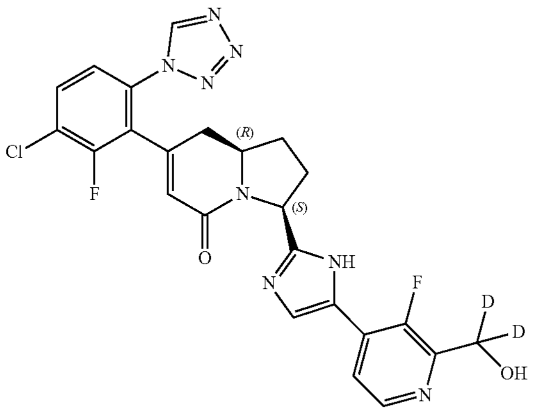

also known as (3S,8aR)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one, and tautomers, stereoisomers, isotopologues, and pharmaceutically acceptable salts or solvates thereof.

In certain embodiments, the present invention is directed to a compound of formula (I-D)

(I-D)

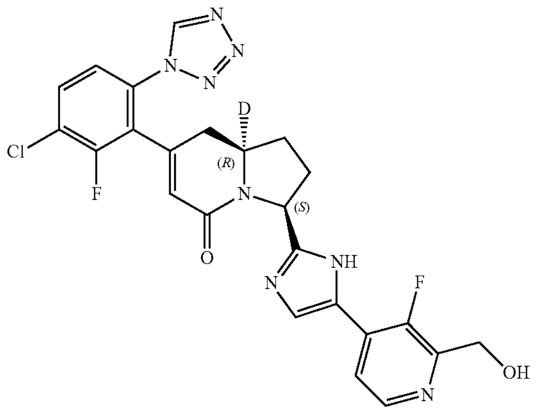

also known as (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8a-d, and tautomers, stereoisomers, isotopologues, and pharmaceutically acceptable salts or solvates thereof.

In certain embodiments, the present invention is directed to a compound of formula (I-E)

(I-E)

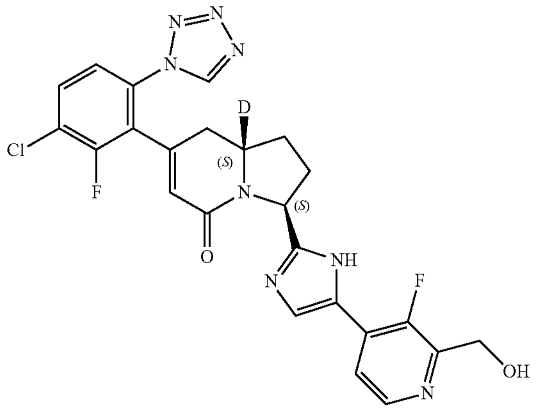

also known as (3S*,8aS)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8a-d, and tautomers, stereoisomers, isotopologues, and pharmaceutically acceptable salts or solvates thereof.

In certain embodiments, the present invention is directed to a compound of formula (I-F)

(I-F)

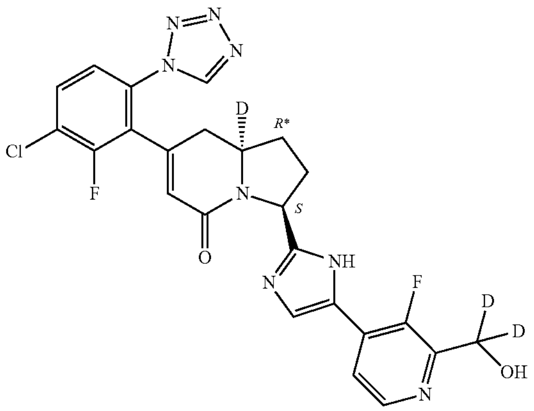

also known as (3S,8aR*)-7-(3-chloro-2-fluoro-6-(1H-tetrazol-1-yl)phenyl)-3-(5-(3-fluoro-2-(hydroxymethyl-d2)pyridin-4-yl)-1H-imidazol-2-yl)-2,3,8,8a-tetrahydroindolizin-5(1H)-one-8a-d, and tautomers, stereoisomers, isotopologues, and pharmaceutically acceptable salts or solvates thereof.

In certain embodiments, the present invention is directed to a compound of formula (I-G)

(I-G)

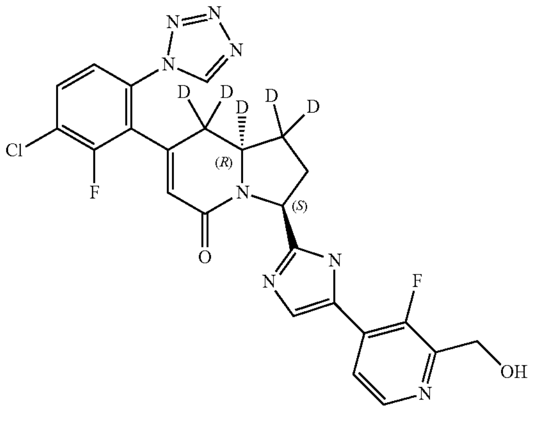

also known as (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-1,1,8,8,8a-d5, and tautomers, stereoisomers, isotopologues, and pharmaceutically acceptable salts or solvates thereof.

In certain embodiments, the present invention is directed to a compound of formula (I-H)

(I-H)

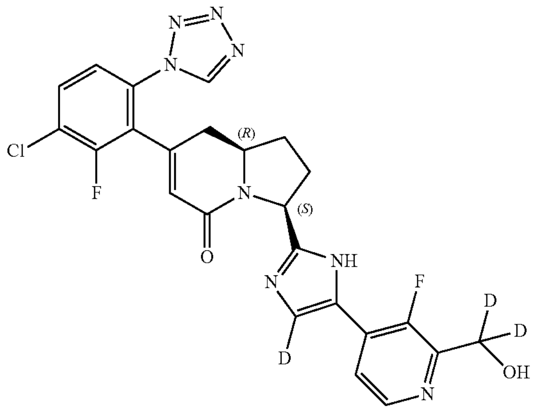

also known as (3S,8aR)-7-(3-chloro-2-fluoro-6-(1H-tetrazol-1-yl)phenyl)-3-(5-(3-fluoro-2-(hydroxymethyl-d2)pyridin-4-yl)-1H-imidazol-2-yl-4-d)-2,3,8,8a-tetrahydroindolizin-5(1H)-one, and tautomers, stereoisomers, isotopologues, and pharmaceutically acceptable salts or solvates thereof.

In certain embodiments, the present invention is directed to a compound of formula (I-J)

(I-J)

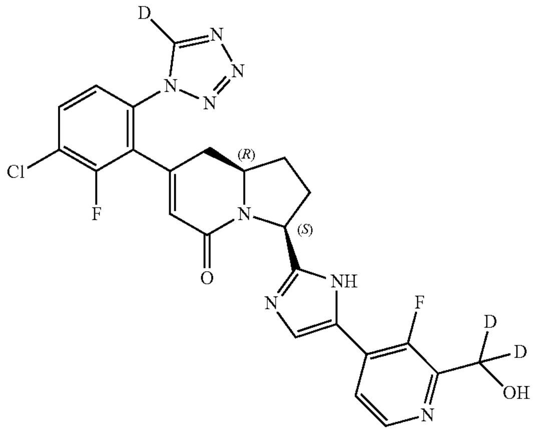

also known as (3R,8aS)-7-(3-Chloro-2-fluoro-6-(1H-tetrazol-1-yl-d)phenyl)-3-(4-(3-fluoro-2-(hydroxymethyl-d2)pyridin-4-yl)-1H-imidazol-2-yl)-2,3,8,8a-tetrahydroindolizin-5(1H)-one, and tautomers, stereoisomers, isotopologues, and pharmaceutically acceptable salts or solvates thereof.

In certain embodiments, the present invention is directed to a compound of formula (I-K)

(I-K)

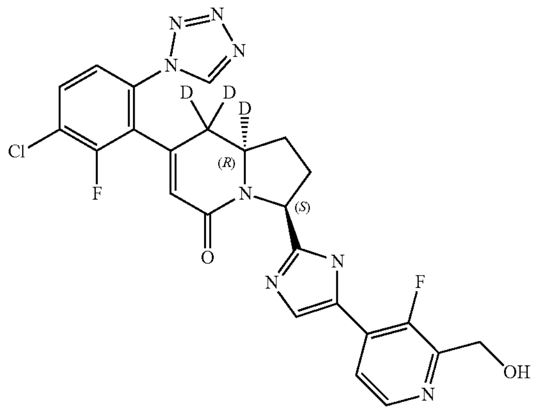

also known as (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8,8,8a-d3, and tautomers, stereoisomers, isotopologues, and pharmaceutically acceptable salts or solvates thereof.

In certain embodiments, the present invention is directed to a compound of formula (I-L)

(I-L)

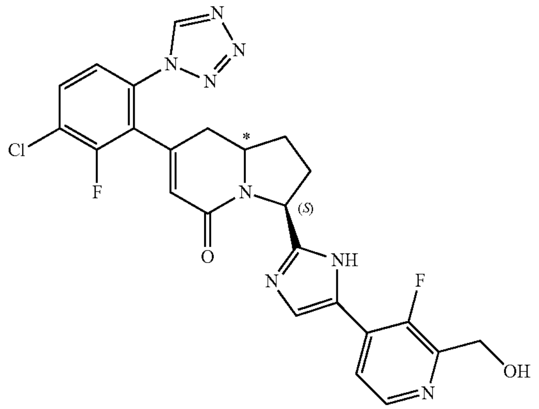

also known as (3S)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one, and tautomers, stereoisomers, isotopologues, and pharmaceutically acceptable salts or solvates thereof.

In certain embodiments, the present invention is directed to a compound of formula (II-A)

(II-A)

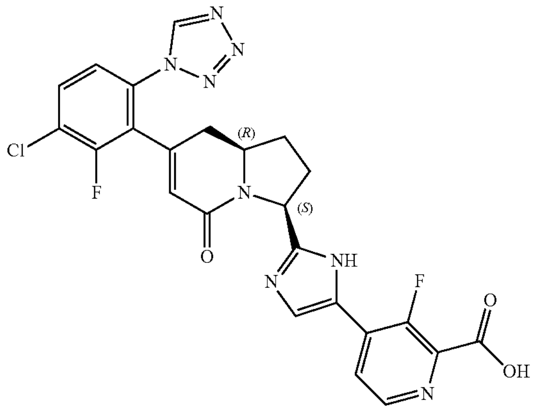

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinic acid, and tautomers, stereoisomers, isotopologues, and pharmaceutically acceptable salts or solvates thereof.

In certain embodiments, the present invention is directed to a compound of formula (II-B)

(II-B)

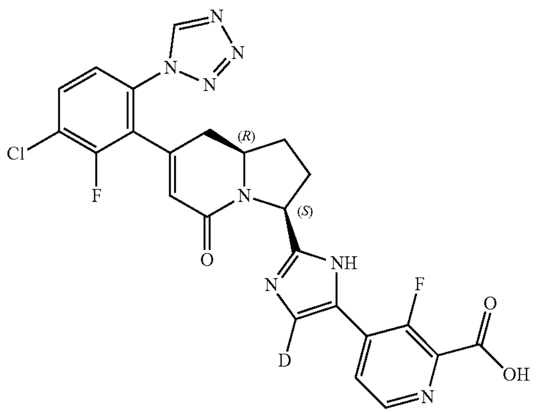

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl-4-d)-3-fluoropicolinic acid, and tautomers, stereoisomers, isotopologues, and pharmaceutically acceptable salts or solvates thereof.

In certain embodiments, the present invention is directed to a compound of formula (II-D)

(II-D)

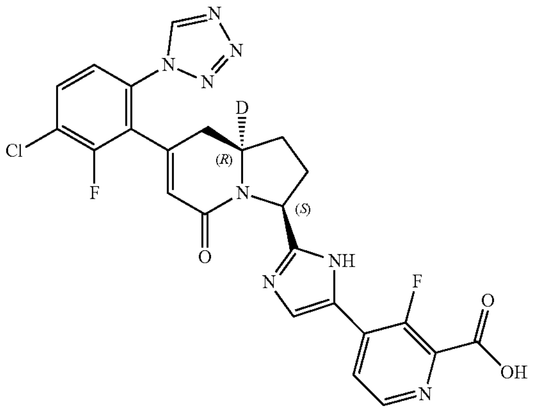

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl-8a-d)-1H-imidazol-5-yl)-3-fluoropicolinic acid, and tautomers, stereoisomers, isotopologues, and pharmaceutically acceptable salts or solvates thereof.

In certain embodiments, the present invention is directed to a compound of formula (II-E)

(II-E)

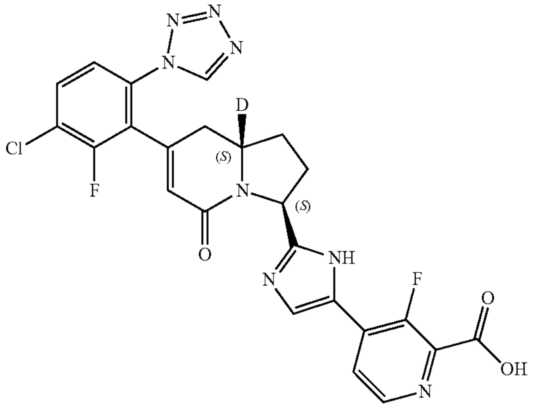

also known as 4-(2-((3S,8aS)-7-(3-chloro-2-fluoro-6-(1H-tetrazol-1-yl)phenyl)-5-oxo-1,2,3,5,8,8a-hexahydroindolizin-3-yl-8a-d)-1H-imidazol-5-yl)-3-fluoropicolinic acid, and tautomers, stereoisomers, isotopologues, and pharmaceutically acceptable salts or solvates thereof.

In certain embodiments, the present invention is directed to a compound of formula (II-F)

(II-F)

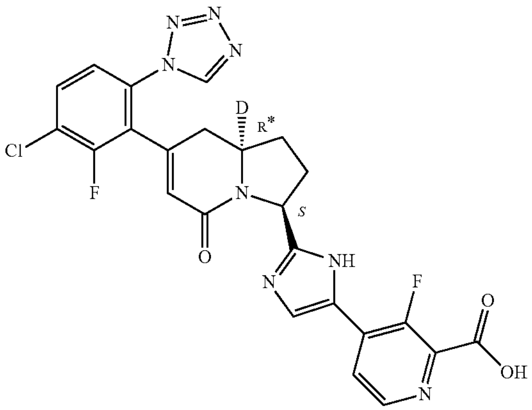

also known as 4-(2-((3S,8aR*)-7-(3-chloro-2-fluoro-6-(1H-tetrazol-1-yl)phenyl)-5-oxo-1,2,3,5,8,8a-hexahydroindolizin-3-yl-8a-d)-1H-imidazol-5-yl)-3-fluoropicolinic acid, and tautomers, stereoisomers, isotopologues, and pharmaceutically acceptable salts or solvates thereof.

In certain embodiments, the present invention is directed to a compound of formula (II-G)

(II-G)

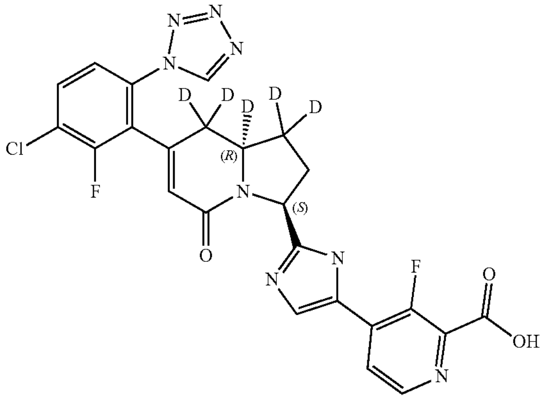

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl-1,1,8,8,8a-d5)-1H-imidazol-5-yl)-3-fluoropicolinic acid, and tautomers, stereoisomers, isotopologues, and pharmaceutically acceptable salts or solvates thereof.

In certain embodiments, the present invention is directed to a compound of formula (II-J)

(II-J)

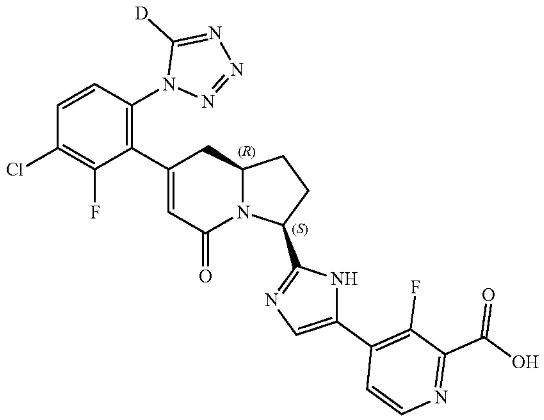

also known as 4-(2-((3S,8aR)-7-(3-chloro-2-fluoro-6-(1H-tetrazol-1-yl-d)phenyl)-5-oxo-1,2,3,5,8,8a-hexahydroindolizin-3-yl)-1H-imidazol-5-yl)-3-fluoropicolinic acid, and tautomers, stereoisomers, isotopologues, and pharmaceutically acceptable salts or solvates thereof.

In certain embodiments, the present invention is directed to a compound of formula (II-K)

(II-K)

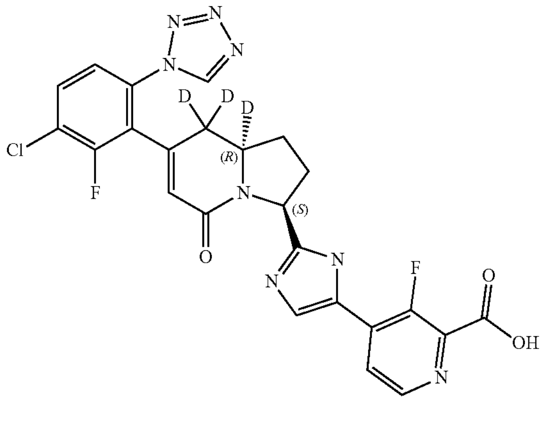

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl-8,8,8a-d3)-1H-imidazol-5-yl)-3-fluoropicolinic acid, and tautomers, stereoisomers, isotopologues, and pharmaceutically acceptable salts or solvates thereof.

In certain embodiments, the present invention is directed to a compound of formula (II-L)

(II-L)

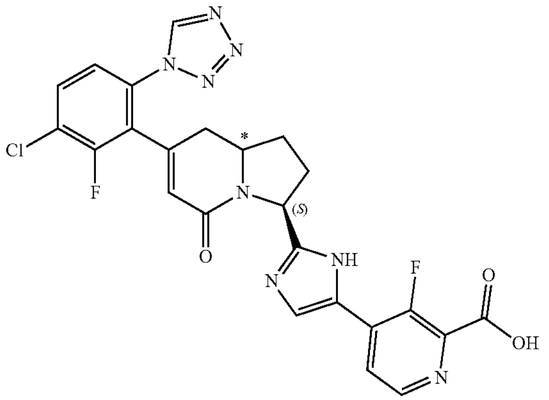

also known as 4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinic acid, and tautomers, stereoisomers, isotopologues, and pharmaceutically acceptable salts or solvates thereof.

In certain embodiments, the present invention is directed to a compound of formula (III-A)

(III-A)

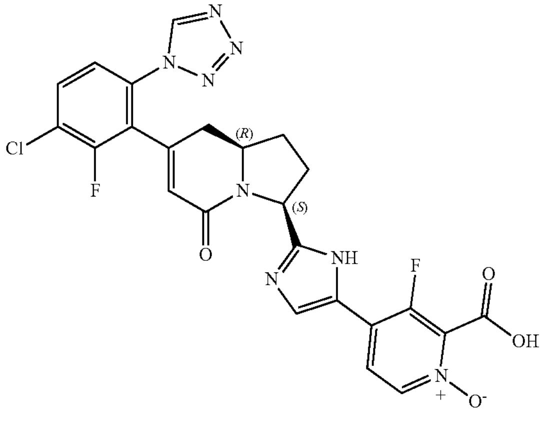

also known as (4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoro-2-(hydroxymethyl)pyridine 1-oxide, and tautomers, stereoisomers, isotopologues, and pharmaceutically acceptable salts or solvates thereof.

In certain embodiments, the present invention is directed to a compound of formula (III-B)

(III-B)

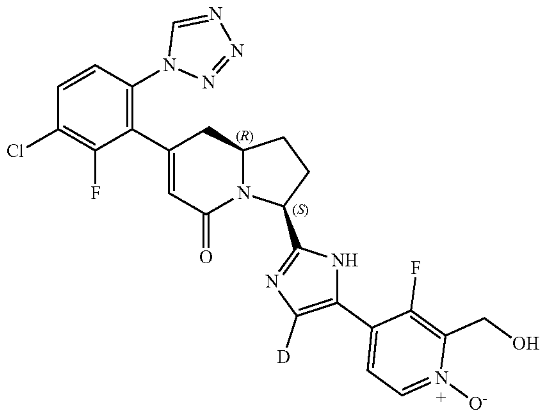

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl-4-d)-3-fluoro-2-(hydroxymethyl)pyridine 1-oxide, stereoisomers, isotopologues, and pharmaceutically acceptable salts or solvates thereof.

In certain embodiments, the present invention is directed to a compound of formula (III-C)

(III-C)

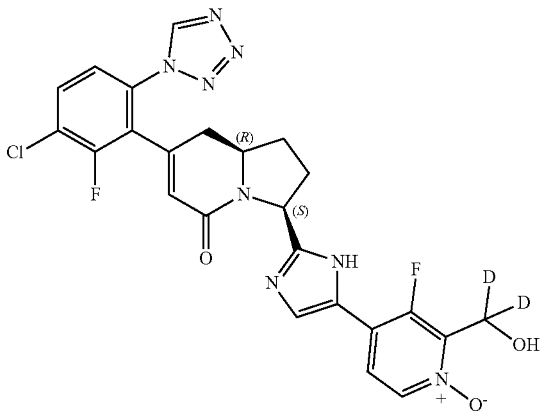

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoro-2-(hydroxymethyl-d2)pyridine 1-oxide, and tautomers, stereoisomers, isotopologues, and pharmaceutically acceptable salts or solvates thereof.

In certain embodiments, the present invention is directed to a compound of formula (III-D)

(III-D)

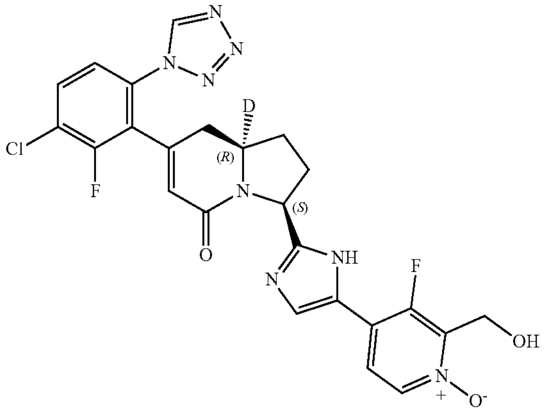

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl-8a-d)-1H-imidazol-5-yl)-3-fluoro-2-(hydroxymethyl)pyridine 1-oxide, and tautomers, stereoisomers, isotopologues, and pharmaceutically acceptable salts or solvates thereof.

In certain embodiments, the present invention is directed to a compound of formula (III-E)

(III-E)

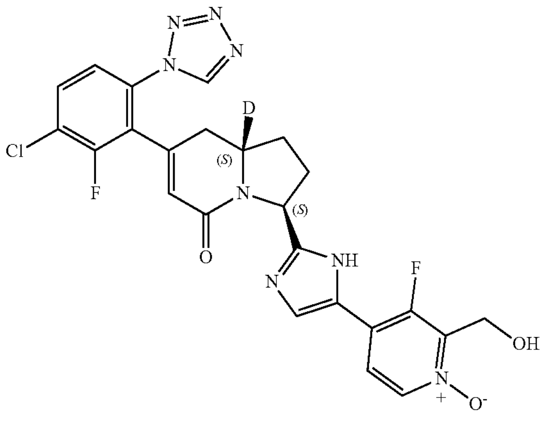

also known as 4-(2-((3S,8aS)-7-(3-chloro-2-fluoro-6-(1H-tetrazol-1-yl)phenyl)-5-oxo-1,2,3,5,8,8a-hexahydroindolizin-3-yl-8a-d)-1H-imidazol-5-yl)-3-fluoro-2-(hydroxymethyl)pyridine 1-oxide, and tautomers, stereoisomers, isotopologues, and pharmaceutically acceptable salts or solvates thereof.

In certain embodiments, the present invention is directed to a compound of formula (III-F)

(III-F)

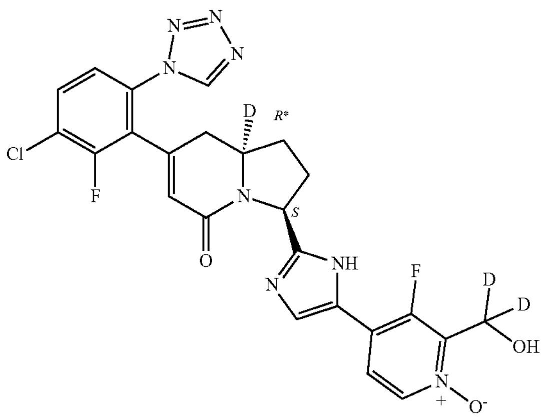

also known as 4-(2-((3S,8aR*)-7-(3-chloro-2-fluoro-6-(1H-tetrazol-1-yl)phenyl)-5-oxo-1,2,3,5,8,8a-hexahydroindolizin-3-yl-8a-d)-1H-imidazol-5-yl)-3-fluoro-2-(hydroxymethyl-d2)pyridine 1-oxide, and tautomers, stereoisomers, isotopologues, and pharmaceutically acceptable salts or solvates thereof.

In certain embodiments, the present invention is directed to a compound of formula (III-G)

(III-G)

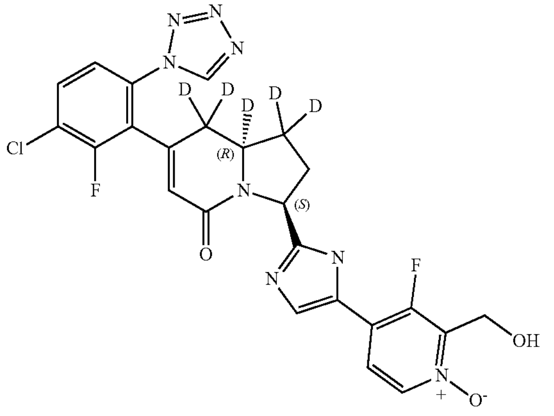

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl-1,1,8,8,8a-d5)-1H-imidazol-5-yl)-3-fluoro-2-(hydroxymethyl)pyridine 1-oxide, and tautomers, stereoisomers, isotopologues, and pharmaceutically acceptable salts or solvates thereof.

In certain embodiments, the present invention is directed to a compound of formula (III-H)

(III-H)

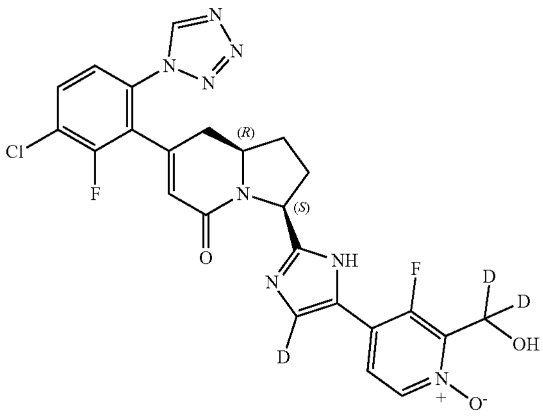

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl-4-d)-3-fluoro-2-(hydroxymethyl-d2)pyridine 1-oxide, and tautomers, stereoisomers, isotopologues, and pharmaceutically acceptable salts or solvates thereof.

In certain embodiments, the present invention is directed to a compound of formula (III-J)

(III-J)

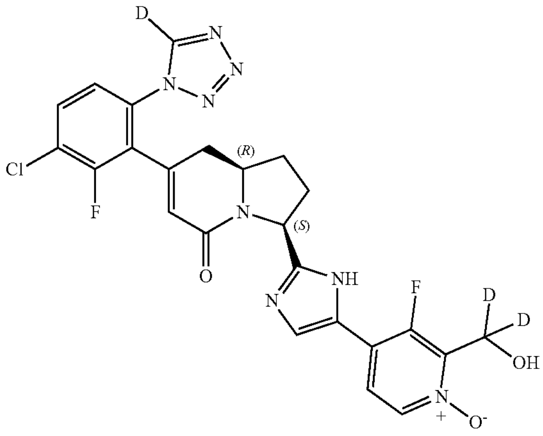

also known as 4-(2-((3S,8aR)-7-(3-chloro-2-fluoro-6-(1H-tetrazol-1-yl-d)phenyl)-5-oxo-1,2,3,5,8,8a-hexahydroindolizin-3-yl)-1H-imidazol-5-yl)-3-fluoro-2-(hydroxymethyl-d2)pyridine 1-oxide, and tautomers, stereoisomers, isotopologues, and pharmaceutically acceptable salts or solvates thereof.

In certain embodiments, the present invention is directed to a compound of formula (III-K)

(III-K)

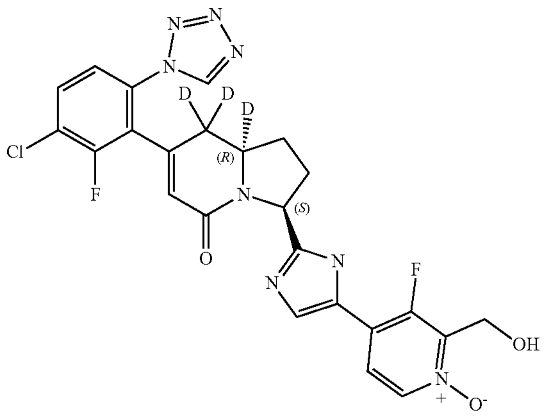

also known as 4-(2-((3S,8aR)-7-(3-chloro-2-fluoro-6-(1H-tetrazol-1-yl)phenyl)-5-oxo-1,2,3,5,8,8a-hexahydroindolizin-3-yl-8,8,8a-d3)-1H-imidazol-5-yl)-3-fluoro-2-(hydroxymethyl)pyridine 1-oxide, and tautomers, stereoisomers, isotopologues, and pharmaceutically acceptable salts or solvates thereof.

In certain embodiments, the present invention is directed to a compound of formula (III-L)

(III-L)

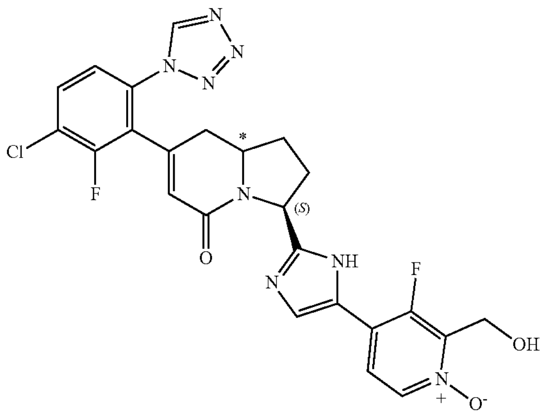

also known as 4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoro-2-(hydroxymethyl)pyridine 1-oxide, and tautomers, stereoisomers, isotopologues, and pharmaceutically acceptable salts or solvates thereof.

The present invention is further directed to a compound of formula (IV)

(IV)

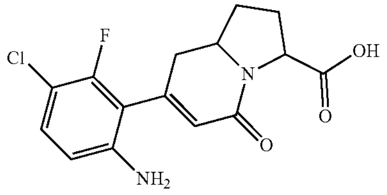

also known as 7-(6-amino-3-chloro-2-fluorophenyl)-5-oxo-1,2,3,5,8,8a-hexahydroindolizine-3-carboxylic acid, and stereoisomers, isotopologues, and salts thereof. The present invention is further directed to a compound of formula (V)

(V)

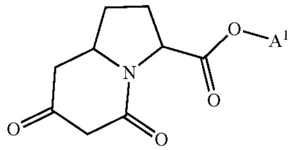

and stereoisomers, isotopologues, and salts thereof. The present invention is further directed to a compound of formula (VI)

(VI)

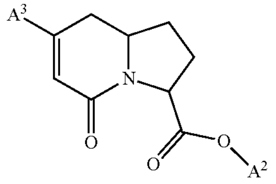

wherein $A^2$ is $C_{1-4}$alkyl, and $A^3$ is selected from $—O—SO_2—CF_3$, $—O—SO_2—CF_2CF_2H$, or $—O—SO_2—CF_2CF_2CF_3$, and stereoisomers, isotopologues, and salts thereof.

The compounds of formula (IV), compounds of formula (V), and compounds of formula (VI) are useful as intermediates in the synthesis of the compounds of formula (I), compounds of formula (II) and/or compounds of formula (III).

In certain embodiments, the present invention is further directed to a compound of formula (IV-A)

(IV-A)

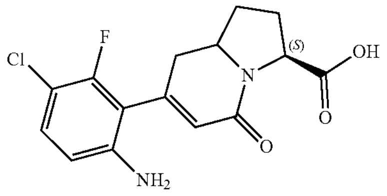

also known as (3S)-7-(6-amino-3-chloro-2-fluorophenyl)-5-oxo-1,2,3,5,8,8a-hexahydroindolizine-3-carboxylic acid, and stereoisomers, isotopologues, and salts thereof.

In certain embodiments of the present invention, $A^1$ is $C_{2-4}$alkyl. In certain embodiments of the present invention, $A^1$ is selected form the group consisting of methyl, ethyl, isopropyl and t-butyl. In certain embodiments of the present invention, $A^1$ is selected from the group consisting of methyl, ethyl and t-butyl. In certain embodiments of the present invention, $A^1$ is selected methyl or ethyl. In certain embodiments of the present invention, $A^1$ is methyl or t-butyl. In certain embodiments of the present invention, $A^1$ is methyl. In certain embodiments of the present invention, $A^1$ is ethyl or t-butyl. In certain embodiments of the present invention, $A^1$ is ethyl.

In certain embodiments, the present invention is directed to compounds of formula (V-S)

(V-S)

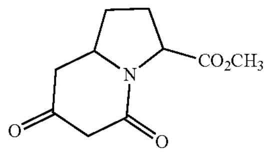

also known as also known as methyl 5,7-dioxooctahydroindolizine-3-carboxylate, and stereoisomers, isotopologues, and salts thereof. In certain embodiments, the present invention is further directed to a compound of formula (V-A)

(V-A)

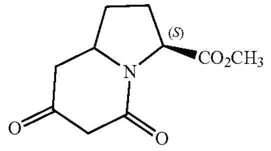

also known as methyl (3S)-5,7-dioxooctahydroindolizine-3-carboxylate, and stereoisomers, isotopologues, and salts thereof.

In certain embodiments of the present invention, $A^2$ is selected form the group consisting of methyl, ethyl, isopropyl and t-butyl. In certain embodiments of the present invention, $A^2$ is selected from the group consisting of methyl, ethyl and t-butyl. In certain embodiments of the present invention, $A^2$ is selected methyl or ethyl. In certain embodiments of the present invention, $A^2$ is methyl or t-butyl. In certain embodiments of the present invention, $A^2$ is methyl.

In certain embodiments of the present invention, $A^3$ is selected from $—O—SO_2—CF_3$ or $—O—SO_2—CF_2CF_2H$. In certain embodiments of the present invention, $A^3$ is selected from $—O—SO_2—CF_3$, or $—O—SO_2—CF_2CF_2CF_3$. In certain embodiments of the present invention, $A^3$ is $—O—SO_2—CF_3$. In certain embodiments of the present invention, $A^3$ is $—O—SO_2—CF_2CF_2H$. In certain embodiments of the present invention, $A^3$ is $—O—SO_2—CF_2CF_2CF_3$, The present invention is directed to a compound of formula (VI-S)

(VI)

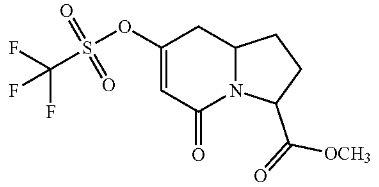

also known as methyl 5-oxo-7-(((trifluoromethyl)sulfonyl)oxy)-1,2,3,5,8,8a-hexahydroindolizine-3-carboxylate, and stereoisomers, isotopologues, and salts thereof. In certain embodiments, the present invention is directed to a compound of formula (VI-A)

(VI-A)

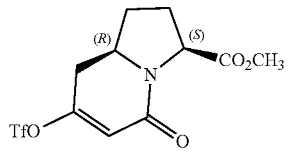

also known as methyl (3S,8aR)-5-oxo-7-(((trifluoromethyl)sulfonyl)oxy)-1,2,3,5,8,8a-hexahydroindolizine-3-carboxylate, and stereoisomers, isotopologues and salts thereof.

In certain embodiments of the present invention, the compound of formula (IV), the compound of formula (V) and/or the compound of formula (VI) is present in an excess of the corresponding 8S-enantiomer.

In certain embodiments, the present invention is directed to methods for the treatment and/or prophylaxis of a thromboembolic disorder comprising administering to a patient in need of such treatment and/or prophylaxis a therapeutically effective amount of a least one of the compounds of the present invention, or a stereoisomer, isotopologue, or pharmaceutically acceptable salt or solvate thereof.

As used herein, the term “thromboembolic disorders” includes arterial cardiovascular thromboembolic disorders, venous cardiovascular or cerebrovascular thromboembolic disorders, and thromboembolic disorders in the chambers of the heart or in the peripheral circulation. The term “thromboembolic disorders” as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In certain embodiments, the term “thromboembolic disorders” includes acute coronary syndrome, stroke, deep vein thrombosis, and pulmonary embolism. In certain embodiments, the "thromboembolic disorders" include hereditary angioedema (HAE) and diabetic macular edema (DME).

In certain embodiments, the present invention is directed to methods for the treatment and/or prophylaxis of an inflammatory disorder comprising: administering to a patient in need of such treatment and/or prophylaxis a therapeutically effective amount of at least one of the compounds of the present invention or a stereoisomer, isotopologue, or pharmaceutically acceptable salt or solvate thereof. Examples of the inflammatory disorders include, but are not limited to, sepsis, acute respiratory distress syndrome, and systemic inflammatory response syndrome.

In certain embodiments, the present invention is directed to methods for the treatment and/or prophylaxis of a disease or condition in which plasma kallikrein activity is implicated, comprising administering to a patient in need of such treatment and/or prophylaxis a therapeutically effective amount of at least one of the compounds of the present invention or a stereoisomer, isotopologue, or pharmaceutically acceptable salt or solvate thereof. The diseases or conditions in which plasma kallikrein activity is implicated include, but are not limited to, impaired visual acuity, diabetic retinopathy, diabetic macular edema, hereditary angioedema, diabetes, pancreatitis, nephropathy, cardiomyopathy, neuropathy, inflammatory bowel disease, arthritis, inflammation, septic shock, hypotension, cancer, adult respiratory distress syndrome, disseminated intravascular coagulation, and cardiopulmonary bypass surgery.

In certain embodiments, the present invention provides a method for the primary prophylaxis of a thromboembolic disorder. In certain embodiments, the present invention provides a method for the primary prophylaxis of a thromboembolic disorder wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In certain embodiments, the present invention provides a method for the secondary prophylaxis of a thromboembolic disorder. In certain embodiments, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

In certain embodiments of the present invention, a compound of formula (I), compound of formula (II), or a compound of formula (III) may be administered in combination with one or more anticoagulant, anti-thrombin agent, anti-platelet agent, fibrinolytic, hypolipidemic agent, antihypertensive agent, and/or anti-ischemic agent. Suitable examples include, but are not limited to warfarin, heparin, aprotinin, a synthetic pentasaccharide, a boroarginine derivative, a boropeptide, heparin, hirudin, argatroban, a thromboxane-A2-receptor antagonist, a thromboxane-A2-synthetase inhibitor, a PDE-III inhibitor, a PDE V inhibitor, an ADP receptor antagonist, an antagonist of the purinergic receptor P2Y1, an antagonist of the purinergic receptor P2Y12, tissue plasminogen activator and modified forms thereof, anistreplase, urokinase, streptokinase, tenecteplase, lanoteplase, a PAI-I inhibitor, an alpha-2-antiplasmin inhibitor, an anisoylated plasminogen streptokinase activator complex, a HMG-CoA reductase inhibitor, a squalene synthetase inhibitor, a fibrate, a bile acid sequestrant, an ACAT inhibitor, a MTP inhibitor, a lipoxygenase inhibitor, a cholesterol absorption inhibitor, a cholesterol ester transfer protein inhibitor, an alpha adrenergic blocker, a beta adrenergic blocker, a calcium channel blocker, a diuretic, a renin inhibitor, an angiotensin-converting enzyme inhibitor, an angiotensin-II-receptor antagonist, an ET receptor antagonist, a Dual ET/A11 antagonist, a neutral endopeptidase inhibitor, a vasopeptidase inhibitor, a Class I agent, a Class II agent, a Class III agent, a Class IV agent, an IAch inhibitor, an IKur inhibitor and a cardiac glycoside.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

One skilled will recognize that in naming the compounds of the present invention, the S* (or *S) and R* (or *R) designations indicate that although the compound was prepared/or is present in an excess of the corresponding stereoisomer, the exact stereo-configuration is not determined. The S and R designations indicate that the compound was prepared/is present in an excess of the corresponding S or R stereoisomer, with the exact stereo-configuration as noted.

Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at a diastereomeric excess of greater than or equal to about 80%, more preferably, at a diastereomeric excess of greater than or equal to about 90%, more preferably still, at a diastereomeric excess of greater than or equal to about 95%, more preferably still, at a diastereomeric excess of greater than or equal to about 98%, most preferably, at a diastereomeric excess of greater than or equal to about 99%.

In certain embodiments, the present invention is directed to a compound of formula (I), compound of formula (II), or a compound of formula (III) in an enantiomeric excess of one of the R- or S-enantiomers (at either of stereocenters denoted with the "*"). In certain embodiments of the present invention, a compound of formula (I), compound of formula (II), or compound of formula (III) is present in an enantiomeric excess of one of the R- or S-enantiomers (at either of the stereocenters denoted with the "*") of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I), compound of formula (II), or the compound of formula (III) is present in an enantiomeric excess of one of the R- or S-enantiomers (at either of the stereocenters denoted with the "*") of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In certain embodiments, the present invention is directed to compound of formula (I), compound of formula (II), or a compound of formula (III) in a diastereomeric or stereoisomeric excess of one of the possible diastereomers or stereoisomers. In certain embodiments of the present invention, a compound of formula (I), compound of formula (II), or a compound of formula (III) is present in a diastereomeric or stereoisomeric excess of one of the possible diastereomers or stereoisomers, of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I), compound of formula (II), or the compound of formula (III) is present in a diastereomeric or stereoisomeric excess of one of the possible diastereomers or stereoisomers of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In certain embodiments, the present invention is directed to a compound of formula (I), compound of formula (II), or compound of formula (III) wherein the stereocenter at the 3-position of the hexahydroindolizin-5(1H)-one is present in a stereoisomeric excess of the corresponding S or R stereoisomer.

In certain embodiments, the present invention is directed to a compound of formula (I), compound of formula (II), or compound of formula (III) wherein the stereocenter at the 8-position of the hexahydroindolizin-5(1H)-one is present in a stereo-isomeric excess of the corresponding S or R stereoisomer.

In certain embodiments, the present invention is directed to a compound of formula (I), compound of formula (II), or compound of formula (III) wherein the stereocenter at the 3-position of the hexahydroindolizin-5(1H)-one is present in a stereoisomeric excess of the corresponding S stereoisomer, and wherein the stereocenter at the 8-position of the hexahydroindolizin-5(1H)-one is present in a stereo-isomeric excess of the corresponding R stereoisomer.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

As used herein, unless otherwise noted, the term "isotopologues" shall mean molecules that differ only in their isotopic composition. More particularly, an isotopologue of a molecule differs from the parent molecule in that it contains at least one atom which is an isotope (i.e. has a different number of neutrons from its parent atom).

For example, isotopologues of water include, but are not limited to, "light water" (HOH or $H_2O$), "semi-heavy water" with the deuterium isotope in equal proportion to protium (HDO or $^1H^2HO$), "heavy water" with two deuterium isotopes of hydrogen per molecule ($D_2O$ or $^2H_2O$), "super-heavy water" or tritiated water ($T_2O$ or $^3H_2O$), where the hydrogen atoms are replaced with tritium ($^3H$) isotopes, two heavy-oxygen water isotopologues ($H_2{}^{18}O$ and $H_2{}^{17}O$) and isotopologues where the hydrogen and oxygen atoms may each independently be replaced by isotopes, for example the doubly labeled water isotopologue $D_2{}^{18}O$. In certain embodiments, isotopologues may be "isotopomers". Isotopomers include both constitutional isomers and stereoisomers solely based on isotopic location. For example, $CH_3CHDCH_3$ and $CH_3CH_2CH_2D$ are a pair of constitutional isotopomers of n-propane; whereas (R)—$CH_3CHDOH$ and (S)—$CH_3CHDOH$ or (Z)—$CH_3CH{=}CHD$ and (E)-$CH_3CH{=}CHD$ are examples of isotopic stereoisomers of ethanol and n-propene, respectively.

It is intended that within the scope of the present invention, any one or more element(s), in particular when mentioned in relation to a compound of formula (I), compound of formula (II), or a compound of formula (III), shall comprise all isotopes and isotopic mixtures of said element (s), either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabeled compounds of formula (I) or compounds of formula (II) may comprise one or more radioactive isotope(s) selected from the group of $^3H$, $^{11}C$ $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

In certain embodiments of the present invention, the compound of formula (I), compound of formula (II), or the compound of formula (III) contains one or more, preferably one to eight, more preferably, one to six, more preferably, one to five, more preferably, one to three, more preferably one to two deuterium atoms bound to a ring or chain carbon atom. In certain embodiments of the present invention, the compound of formula (I), compound of formula (II), or the compound of formula (III) contains one or more, preferably one to three, more preferably, one to two deuterium atoms bound to a ring or chain carbon atom.

One skilled in the art will further recognize that the compounds of formula (I), compound of formula (II), and compounds of formula (III) may exist as tautomers (i.e. structural isomers that may readily interconvert), more particularly tatutomers at the imidazolyl portion of the compound. One skilled in the art will further recognize that the compounds of formula (I), compounds of formula (II), and compounds of formula (III) may exist as either tautomeric form, or as any mixture of its tautomeric forms.

It is further intended that the present invention includes the compounds described herein, including all isomers thereof (including, but not limited to stereoisomers, enantiomers, diastereomers, tautomers, isotopologues, atropisomers, and the like).

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

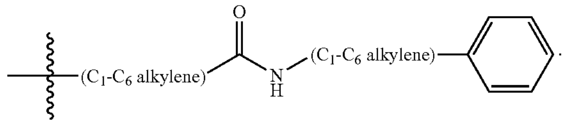

Abbreviations used in the specification, particularly the Schemes and Examples, are as listed in the Table A, below:

TABLE A

| Abbreviations | |
|---|---|
| AcOH = | Acetic Acid |
| ACN or MeCN = | Acetonitrile |
| APO (cells) = | Apoptotic (cells) |
| aPTT = | Activated Partial Thromboplastin Time |
| aq. = | Aqueous |
| AUC = | Area Under the Curve |
| AV = | Arteriovenous |
| $BF_3$•$Et_2O$ = | Boron trifluoride etherate |
| BINAP = | (2,2'-Bis(diphenylphosphino)-1,1'-binaphthyl) |
| BN (cells) = | Binucleated (cells) |
| B(O—iPr)$_3$ = | Tris(isopropyl) Borate |
| Boc or BOC = | tert-Butoxyloxycarbonyl (i.e. —C(O)—O—C($CH_3$)$_3$) |
| (BOC)$_2$O or (Boc)$_2$O = | Boc Anhydride or Di-tert-butyl dicarbonate |
| BSA = | Bovine Serum Albumin |
| CDI = | 1,1,-Carbonyldiimidazole |
| CHAPS = | 3-[(3-cholamidopropyl)dimethylammonio]-1-propanesulfonate |
| CYP = | Cytochrome P450 |
| DAPI = | (4',6-Diamidino-2-phenylindole) |
| DBU = | 1,8-Diazabicyclo[5.4.0]undec-7-ene |
| DCM = | Dichloromethane |
| DDI = | Drug-Drug Interaction |
| DEA = | Diethanolamine |
| DIEA or DIPEA = | Diisopropyl ethylamine |
| DMF = | N,N-Dimethylformamide |
| DMSO = | Dimethylsulfoxide |
| EA or EtOAc = | Ethyl Acetate |
| EGTA = | (Ethylene glycol-bis(β-aminoethyl ether)-N,N,N',N'-tetraacetic acid) |
| EMEM = | Eagle's minimal essential medium |
| EtOH = | Ethanol |
| $Et_2O$ = | Diethyl Ether |
| $Et_3N$ or TEA = | Triethylamine |
| Factor XIa or FXIa = | Factor XIa |
| FCCP = | (Carbonyl cyanide-p-trifluoromethoxyphenylhydrazone) |
| FIX = | Factor IX |
| FBS = | Fetal Bovine Serum |
| Grubbs 2$^{nd}$ Generation Catalyst = | (1,3-Bis(2,4,6-trimethylphenyl)-2-imidazolidinylidene)dichloro(phenylmethylene)(tri cyclohexylphosphine)ruthenium |
| GSH = | Glutathione |
| HEPES (buffer) | (4-(2-Hydroxyethyl)-1-piperazineethanesulfonic acid) buffer solution |
| hERG or HERG = | Human ether-à-go-go-related gene |
| Hex = | Hexane(s) |
| HLM = | Human Liver Microsomes |

TABLE A-continued

| Abbreviations | |
|---|---|
| HPbCD = | (2-Hydroxypropyl)-beta-cyclodextrin |
| HPLC = | High Performance Liquid Chromatography |
| HPMC = | Hydroxypropyl methylcellulose |
| i.d. = | Inner (or interior) Diameter |
| i.v. = | Intravenous |
| IBX = | 2-Iodoxybenzoic Acid |
| IPA = | Isopropyl Alcohol |
| KHB = | Krebs-Henseleit Buffer |
| LC-MS or LC/MS = | Liquid chromatography-mass spectrometry |
| LDA = | Lithium diisopropylamide |
| m-CPBA = | meta-Chloroperoxybenzoic acid |
| Me = | Methyl |
| MeCN or CAN = | Acetonitrile |
| MeOH = | Methanol |
| MgATP = | Adenosine 5'-(tetrahydrogen triphosphate) Magnesium Salt |
| MN = | Micronuclei |
| MNC = | MicroNucleated Cells |
| MNT = | Micronucleus Test |
| NADPH | Nicotinamide Adenine Dinucleotide Phosphate Hydrogen |
| NaOt-Bu or t-BuONa = | Sodium tert-Butoxide |
| NBS = | N-Bromosuccinimide |
| n-BuLi = | n-Butyllithium |
| $NH_4OAc$ = | Ammonium Acetate |
| NIS = | N-Iodosuccinimide |
| NMR = | Nuclear Magnetic Resonance |
| OCR = | Oxygen Consumption Rate |
| Pd/C = | Palladium on Carbon (catalyst) |
| Pd(dppf)$Cl_2$ = | [1,1-Bis(diphenylphosphino)ferrocene] dichloropalladium (II) |
| Pd($PPh_3$)$_4$ = | Tetrakis(triphenylphosphine)palladium(0) |
| PE = | Petroleum ether |
| PEG 400 = | Polyethylene Glycol 400 |
| Pen/Strep = | Penicillin/streptomycin |
| PhI(OAc)$_2$ | (Diacetoxyiodo)benzene |
| $PhNTf_2$ = | Bis(trifluoromethanesulfonyl)aniline |
| PK = | Phamacokinetics |
| POLY (cells) = | Polynucleated (cells) |
| PPP = | Platelet Poor Plasma |
| RFU = | Relative Fluorescence Unit(s) |
| RPD = | Relative Population Doubling |
| RT = | Retention Time |
| SD = | Standard Deviation |
| SEM = | Standard Error of Mean |
| SRC = | Spare Respiratory Capacity |
| TBSCl = | tert-Butyldimethylsilyl chloride |
| TDI = | Time Dependent Inhibition |
| TEA = | Triethylamine |
| TEMPO = | (2,2,6,6-Tetramethylpiperidin-1-yl)oxyl or (2,2,6,6-tetramethylpiperidin-1-yl)oxidanyl |
| Tf or triflyl = | Trifluoromethylsulfonyl (i.e. —$SO_2$—$CF_3$) |
| TFA = | Trifluoroacetic Acid |
| TFAA = | Trifluoroacetic anhydride |
| THF = | Tetrahydrofuran |
| $TMSN_3$ = | Trimethylsilylazide |
| $T_3P$ = | Propanephosphonic acid anhydride (PPAA) |
| Tris (buffer) = | 2-Amino-2-(hydroxymethyl)-1,3-propanediol |
| UV = | Ultraviolet |

As used herein, unless otherwise noted, the term "isolated form" shall mean that the compound is present in a form which is separate from any solid mixture with another compound(s), solvent system or biological environment. In an embodiment of the present invention, the compound of formula (I) is present in an isolated form. In an embodiment of the present invention, the compound of formula (II) is present in an isolated form. In an embodiment of the present invention, the compound of formula (III) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form. In an embodiment of the present invention, the compound of formula (II) is present as a substantially pure form. In an embodiment of the present invention, the compound of formula (III) is present as a substantially pure form.

As used herein, unless otherwise noted, the term "substantially free of a corresponding salt form(s)" when used to described a compound of formula (I), a compound of formula (II), or a compound of formula (III) shall mean that mole percent of the corresponding salt form(s) in the isolated compound of formula (I), isolated compound of formula (II), or isolated compound of formula (II) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s). In an embodiment of the present invention, the compound of formula (II) is present in a form which is substantially free of corresponding salt form(s). In an embodiment of the present invention, the compound of formula (III) is present in a form which is substantially free of corresponding salt form(s).

As used herein, unless otherwise noted, the terms "treating", "treatment" and the like, shall include the management and care of a subject or patient, preferably a mammal, more preferably a human, for the purpose of combating a disease, condition, or disorder and includes the administration of a compound of the present invention to prevent the onset of the symptoms or complications, alleviate the symptoms or complications, slow the progression of the disease or disorder, or eliminate the disease, condition, or disorder. The terms "treating" or "treatment" further include: (a) inhibiting the disease-state, i.e., arresting its development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a stereoisomer, isotopologue, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

As used herein, "risk reduction" covers therapies that lower the incidence of development of a clinical disease state. As such, primary and secondary prevention therapies are examples of risk reduction.

One skilled in the art will recognize that wherein the present invention is directed to methods of prophylaxis, the subject in need thereof (e.g., a subject in need of prophylaxis) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical professional to be at risk of developing said disorder, disease or condition. For example, the subject may be deemed at risk of developing a disorder, disease or condition (and therefore in need of prophylaxis or prophylactic treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

As used herein, the term "composition" is intended to encompass a product comprising the specified ingredients in the specified amounts, as well as any product which results, directly or indirectly, from combinations of the specified ingredients in the specified amounts.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The compounds of the present invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, for example, may occur when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently or consecutively to the mammal being treated. When administered in combination each component may be administered at the same time or sequentially in any order at different points in time. Thus, each component may be administered separately but sufficiently closely in time so as to provide the desired therapeutic effect.

One or more additional pharmacologically active agents may be administered in combination with the compounds of the invention. The additional active agent (or agents) is intended to mean a pharmaceutically active agent (or agents) that is active in the body, including pro-drugs that convert to pharmaceutically active form after administration, which is different from the compound of formula (I) or compound of formula (II), and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of formula (I) or compound of formula (II) in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers (ARBs) (e.g., losartan (i.e., COZAAR®), valsartan, candesartan, olmesartan, telmesartan, eprosartan, irbesartan and any of these drugs used in combination with hydrochlorothiazide such as HYZAAR® (losartan combination with hydrochlorothiazide); diuretics, e.g. hydrochlorothiazide (HCTZ); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892 (CAS Registry Number 126222-34-2, also known as remikiren); A 65317 (CAS Registry Number 119625-78-4); CP 80794 (CAS Registry Number 119625-78-4, also known as terlakiren)); ES 1005 (CAS Registry Number 115404-79-0); ES 8891 (CAS Registry Number 129445-88-1); SQ 34017 (CAS Registry Number 695226-77-8); aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamide hemifumarate); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible. Compounds which can be alternatively or additionally administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Anticoagulant agents (or coagulation inhibitory agents) that may be used in combination with the compounds of this invention include warfarin, heparin (either unfractionated heparin or any commercially available low molecular weight heparin, for example enoxaparin and dalteparin), aprotinin, synthetic pentasaccharide inhibitors of Factor Xa such as fondaparinux and idraparinux, direct Factor Xa inhibitors such as rivaroxaban, apixaban, betrixaban, edoxaban, otamixaban, direct acting thrombin inhibitors including hirudin, dabigatran, argatroban, ximelagatran, melagatran, lepirudin, desirudin, and bivalirudin, as well as other factor Vila inhibitors, Villa inhibitors, DCa inhibitors, Xa inhibitors, XIa inhibitors, fibrinogen receptor antagonists (including abciximab, eptifibatide and tirofiban), TAFI inhibitors, and others known in the art. Factor DCa inhibitors include synthetic active-site blocked competitive inhibitors, oral inhibitors and RNA aptamers. These are described in the previously cited Howard et al. reference (Howard, E L, Becker K C, Rusconi, C P, Becker R C. Factor IXa Inhibitors as Novel Anticoagulants. Arterioscler Thromb Vase Biol. 2007; 27: 722-727).

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred.

Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors P2Y1 and P2Y12 with P2Y12 being even more preferred. Preferred P2Y12 receptor antagonists include ticlopidine, prasugrel, clopidogrel, elinogrel, ticagrelor and cangrelor, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-I and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, dabigatran and argatroban, including pharmaceutically acceptable salts and prodrugs thereof.

Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role. Thrombin receptor antagonist peptides have been identified based on structure-activity studies involving substitutions of amino acids on thrombin receptors. In Bernatowicz et al, J Med. Chem., vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-NH2 and N-trans-cinnamoyl-p-fluoroPhe-p-guanidinoPhe-Leu-Arg-Arg-NH2. Peptide thrombin receptor antagonists are also disclosed in WO 94/03479. Substituted tricyclic thrombin receptor antagonists are disclosed in U.S. Pat. Nos. 6,063,847, 6,326,380 and WO 01/96330 and U.S. Pat. No. 7,037,920. Other thrombin receptor antagonists include those disclosed in U.S. Pat. Nos. 7,304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complexes, including pharmaceutically acceptable salts or prodrugs thereof. The term anistreplase, as used herein, refers to anisoylated plasminogen streptokinase activator complexes, as described, for example, in European Patent No. 0028489. The term urokinase, as used herein, is intended to denote both dual and single chain urokinase, the latter also being referred to herein as prourokinase. Examples of suitable anti-arrhythmic agents for use in combination with the present compounds include: Class I agents (such as propafenone); Class II agents (such as carvedilol and propranolol); Class III agents (such as sotalol, dofetilide, amiodarone, azimilide and ibutilide); Class IV agents (such as ditiazem and verapamil); IAch inhibitors, and IKur inhibitors (e.g., compounds such as those disclosed in WO01/40231).

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example, wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

One skilled in the art will recognize that wherein a reaction step of the present invention may be carried out in a variety of solvents or solvent systems, said reaction step may also be carried out in a mixture of the suitable solvents or solvent systems.

One skilled in the art will further recognize that the reaction or process step(s) as herein described are allowed to proceed for a sufficient period of time until the reaction is complete, as determined by any method known to one skilled in the art, for example, chromatography (e.g. HPLC). In this context a "completed reaction or process step" shall mean that the reaction mixture contains a significantly diminished amount of the starting material(s)/reagent(s) and a significantly increased amount of the desired product(s), as compared to the amounts of each present at the beginning of the reaction.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$═CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be identified in texts such as T. W. Greene & P. G. M. Wuts, Protective Groups in Organic Synthesis, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be identified in texts such as T. W. Greene & P. G. M. Wuts, Protective Groups in Organic Synthesis, John Wiley & Sons, 1991.

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha\text{-obs}]/[\alpha\text{-max}])\times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1 S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Synthesis

Compounds of formula (I), compounds of formula (II), compounds of formula (III), compounds of formula (IV), compounds of formula (V), and compounds of formula (VI) of the present invention may be prepared as described in the Synthesis Examples which follow hereinafter. The preparation of the starting materials used in the synthesis examples which follow hereinafter is well within the skill of persons versed in the art.

Pharmaceutical Compositions

The present invention further comprises pharmaceutical compositions containing a compound of formula (I) and/or a compound of formula (II) and/or compound of formula (III) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.05 mg/day to about 1000 mg/day, or any amount or range therein, about 0.1 mg/day to about 500 mg/day, or any amount or range therein, preferably from about 1 mg/day to about 300 mg/day, or any amount or range therein.

The dosages, however, may be varied depending upon the requirement of the patients, the severity of the condition being treated and the compound being employed. Daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form yielding the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of the treatment and/or prophylaxis of thromboembolic disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein, preferably from about 0.05 mg to about 300 mg of the compound, or any amount or range therein, more preferably from about 0.1 mg to about 100 mg of the compound, or any amount or range therein, more preferably from about 0.1 mg to about 50 mg of the compound, or any amount or range therein; and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) and/or a compound of formula (II) and/or compound of formula (III) as the active ingredient is intimately admixed with a pharmaceutical carrier according to conventional pharmaceutical compounding techniques, which carrier may take a wide variety of forms depending on the form of preparation desired for administration (e.g. oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain. Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

Compounds of the present invention may be administered in any of the foregoing compositions and according to dosage regimens established in the art whenever treatment or prophylaxis of thromboembolic disorders, inflammatory disorders or diseases or conditions in which plasma kallikrein activity is implicated is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug may be ordinarily supplied at a dosage level of from about 0.005 mg/kg to about 10 mg/kg of body weight per day, or any amount or range therein. Preferably, the range is from about 0.01 to about 5.0 mg/kg of body weight per day, or any amount or range therein, more preferably, from about 0.1 to about 1.0 mg/kg of body weight per day, or any amount or range therein, more preferably, from about 0.1 to about 0.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

SYNTHESIS EXAMPLES

Example 1: Intermediate 1 Compound of Formula (IV-A)

(3S)-7-(6-Amino-3-chloro-2-fluorophenyl)-5-oxo-1,2,3,5,8,8a-hexahydroindolizine-3-carboxylic acid

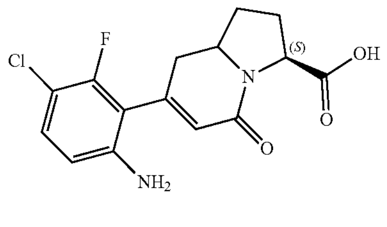

Step 1: Synthesis of 1-(tert-butyl) 2-methyl (2S)-5-methoxypyrrolidine-1,2-dicarboxylate To a solution of 1-(tert-butyl) 2-methyl (S)-5-oxopyrrolidine-1,2-dicarboxylate (2.1 g, 8.63 mmol, 1.0 equiv.) in THF (40 mL) was added lithium triethylborohydride (13 mL, 13 mmol, 1.5 equiv., 1 M in THF) dropwise at −78° C. and under $N_2$. The reaction was stirred for 40 min at −78° C., and then $Na_2CO_3$ (aq., 10 mL) was added at −78° C. and the mixture warmed to 0° C. Hydrogen peroxide (1 mL, 30%) was added and the resulting mixture was stirred for 30 min at room temperature. THF was removed from the mixture under vacuum, and the resulting residue was extracted with diethyl ether, washed with brine, dried and concentrated under vacuum to yield a colorless oil. The colorless oil was dissolved in methanol (40 mL), and p-toluenesulfonic acid (149 mg, 0.86 mmol, 0.1 equiv.) was added to the mixture. The resulting solution was stirred overnight at room temperature. The reaction was quenched with water and the resulting mixture was extracted with diethyl ether. The combined organic layer was washed with brine, dried over $Na_2SO_4$ and concentrated to yield 1-(tert-butyl) 2-methyl (2S)-5-methoxypyrrolidine-1,2-dicarboxylate as a colorless oil.

Step 2: Synthesis of 1-(tert-butyl) 2-methyl (2S)-5-allylpyrrolidine-1,2-dicarboxylate To a solution of 1-(tert-butyl) 2-methyl (2S)-5-methoxypyrrolidine-1,2-dicarboxylate (10 g, 38.6 mmol, 1.0 equiv.) in $Et_2O$ (200 mL) were added allyltrimethylsilane (27 ml, 169.7 mmol, 4.4 equiv.) and boron trifluoride etherate (6.57 g, 46.3 mmol, 1.2 equiv.) at −40° C. and under a $N_2$ atmosphere. The resulting mixture was stirred for 30 min at −40° C., warmed to room temperature and then stirred for 40 min. The reaction was quenched with $Na_2CO_3$ (aq.) and the resulting mixture was extracted with ethyl acetate. The combined organic layer was washed with brine, dried over $Na_2SO_4$ and concentrated. The resulting residue was purified by silica gel chromatography (0-20% EtOAc/petroleum ether) to yield 1-(tert-butyl) 2-methyl (2S)-5-allylpyrrolidine-1,2-dicarboxylate as a yellow oil. LC/MS: mass calculated for $C_{14}H_{23}NO_4$: 269.16, measured: 270.20 $[M+H]^+$.

Step 3: Synthesis of 1-(tert-butyl) 2-methyl (2S)-5-(2-oxoethyl)pyrrolidine-1,2-dicarboxylate To a solution of 1-(tert-butyl) 2-methyl (2S)-5-allylpyrrolidine-1,2-dicarboxylate (7.3 g, 27.1 mmol, 1.0 equiv.) in $THF/H_2O$ (120 mL) was added $OSO_4$ (347 mg, 1.36 mmol, 0.05 equiv.). The resulting mixture was stirred for 5 min at room temperature in the dark, and then sodium periodate (14.5 g, 67.8 mmol, 2.5 equiv.) was added. The mixture was stirred for 4 h at room temperature. The reaction was quenched with water and the resulting mixture was extracted with ethyl acetate. The combined organic layer was washed with brine and dried over $Na_2SO_4$. The solids were filtered out. The filtrate was concentrated under vacuum. The resulting residue was purified by silica gel chromatography (0-40% EA/PE) to yield 1-(tert-butyl) 2-methyl (2S)-5-(2-oxoethyl)pyrrolidine-1,2-dicarboxylate as a yellow oil. LC/MS: mass calculated for $C_{13}H_{21}NO_5$: 271.14, measured: 272.15 $[M+H]^+$, 216.05 $[M-C_4H_9]^+$.

Step 4: Synthesis of racemic 1-(tert-butyl) 2-methyl (2R)-5-(4-ethoxy-2-hydroxy-4-oxobutyl)pyrrolidine-1,2-dicarboxylate To a solution of ethyl acetate (0.936 mL, 9.583 mmol, 4 eq) in tetrahydrofuran (10 mL) was added 1 M of Lithium bis(trimethylsilyl)amide (9.583 mL, 9.583 mmol, 4 eq) at −78° C. under $N_2$ atmosphere. After stirring for 30 min at the same temperature, to the mixture was added 1-(tert-butyl) 2-methyl (2S)-5-(2-oxoethyl)pyrrolidine-1,2-dicarboxylate (650 mg, 2.396 mmol, 1 eq) in tetrahydrofuran (10 mL) and the mixture was stirred for 30 min at −78° C. The reaction was quenched with saturated aqueous ammonium chloride followed by extraction using ethyl acetate (3×20 mL). The organic layer was dried over magnesium sulfate, filtered and concentrated in vacuo. The residue obtained was purified by silica gel chromatography (0-45% ethyl acetate/petroleum ether) to afford the rac-1-(tert-butyl) 2-methyl (2R)-5-(4-ethoxy-2-hydroxy-4-oxobutyl)pyrrolidine-1,2-dicarboxylate as a yellow oil (747 mg, 86.751% yield). LC/MS: mass calculated for $C_{17}H_{29}NO_7$: 359, measured: 382 [M+Na]+.

Step 5: Synthesis of 1-(tert-butyl) 2-methyl (2S)-5-(4-ethoxy-2,4-dioxobutyl)pyrrolidine-1,2-dicarboxylate To a solution of 1-(tert-butyl) 2-methyl (2S)-5-(4-ethoxy-2-hydroxy-4-oxobutyl)pyrrolidine-1,2-dicarboxylate (3.3 g, 9.2 mmol, 1.0 equiv.) in acetonitrile (30 mL) was added 2-iodoxybenzoic acid (IBX) (10.3 g, 36.8 mmol, 4.0 equiv.). The resulting mixture was stirred overnight at 50° C. The solvent was removed and partitioned between EtOAc and brine. The organic layer was separated, dried, and concentrated under reduced pressure. The resulting residue was purified by silica gel chromatography (0-80% EtOAc/petroleum ether) to yield 1-(tert-butyl) 2-methyl (2S)-5-(4-ethoxy-2,4-dioxobutyl)pyrrolidine-1,2-dicarboxylate as a yellow oil. LC/MS: mass calculated for $C_{17}H_{27}NO_7$: 357.18, measured: 380.15 $[M+Na]^+$.

Step 6: Synthesis of methyl (3S)-5,7-dioxooctahydroindolizine-3-carboxylate

To a solution of 1-(tert-butyl) 2-methyl (2S)-5-(4-ethoxy-2,4-dioxobutyl)pyrrolidine-1,2-dicarboxylate (900 mg, 2.5 mmol, 1.0 equiv.) in DCM (2.5 ml) was added HCl (in 1,4-dioxane, 4 M, 2.5 ml). The resulting mixture was stirred for 1 h at room temperature. The solvent then was removed under vacuum to yield a yellow oil. The yellow oil was dissolved in toluene (5 mL), and sodium bicarbonate (2.1 g, 25.2 mmol, 10.0 equiv.) was added. The resulting mixture was stirred overnight at 110° C. The reaction was quenched with water and extracted with ethyl acetate. The combined organic layer was washed with brine, dried over $Na_2SO_4$ and concentrated. The resulting residue was purified by silica gel chromatography (0-50% EtOAc/petroleum ether) to yield methyl (3S)-5,7-dioxooctahydroindolizine-3-carboxylate as a yellow solid. LC/MS: mass calculated for $C_{10}H_{13}NO_4$: 211.08, measured: 212.10 $[M+H]^+$.

Step 7: Synthesis of methyl (3S)-5-oxo-7-(((trifluoromethyl)sulfonyl)oxy)-1,2,3,5,8,8a-hexahydroindolizine-3-carboxylate To a solution of methyl (3S)-5,7-dioxooctahydroindolizine-3-carboxylate (370 mg, 1.75 mmol, 1.0 equiv.) in dichloromethane (5 mL) were added triethylamine (355 mg, 3.5 mmol, 2.0 equiv.) and N,N-bis(trifluoromethylsulfonyl)aniline (751 mg, 2.1 mmol, 1.2 equiv.). The resulting mixture was stirred overnight at room temperature. The mixture was then concentrated and the residue purified by silica gel chromatography (0-80% EA/PE) to yield methyl (3S)-5-oxo-7-(((trifluoromethyl)sulfonyl)oxy)-1,2,3,5,8,8a-hexahydroindolizine-3-carboxylate as a yellow solid. LC/MS: mass calculated for $C_{11}H_{12}F_3NO_6S$: 343.03, measured: 344.05 $[M+H]^+$.

Step 8: Synthesis of methyl (3S)-7-(6-amino-3-chloro-2-fluorophenyl)-5-oxo-1,2,3,5,8,8a-hexahydroindolizine-3-carboxylate To a solution of methyl (3S)-5-oxo-7-(((trifluoromethyl)sulfonyl)oxy)-1,2,3,5,8,8a-hexahydroindolizine-3-carboxylate (350 mg, 1.02 mmol, 1.0 equiv.), (6-amino-3-chloro-2-fluorophenyl)boronic acid (232 mg, 1.2 mmol, 1.2 equiv.) and potassium carbonate (282 g, 2.04 mmol 2.0 equiv.) in 1,4-dioxane/$H_2O$ (5 mL, 10/1) was added [1,1'-bis(diphenylphosphino)ferrocene]dichloropalladium(II) (37 mg, 0.05 mmol, 0.1 equiv.). The resulting mixture was stirred for 2 h at 80° C. under $N_2$. The reaction was quenched with water and extracted with ethyl acetate. The combined organic layer was washed with brine and dried over $Na_2SO_4$. The solids were filtered out and the filtrate was concentrated under vacuum. The resulting residue was purified by silica gel chromatography (0-100% EtOAc/petroleum ether) to yield methyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{16}H_{16}ClFN_2O_3$: 338.08, measured: 339.10 $[M+H]^+$.

Step 9: Synthesis of (3S)-7-(6-amino-3-chloro-2-fluorophenyl)-5-oxo-1,2,3,5,8,8a-hexahydroindolizine-3-carboxylic acid To a solution of methyl (3S)-7-(6-amino-3-chloro-2-fluorophenyl)-5-oxo-1,2,3,5,8,8a-hexahydroindolizine-3-carboxylate (210 mg, 0.62 mmol, 1.0 equiv.) in THF/$H_2O$/MeOH (5 mL, 3/1/1) was added lithium hydroxide (124 mg, 3.10 mmol, 5.0 equiv.). The resulting mixture was stirred for 1 h at room temperature. The resulting mixture was adjusted to pH 4 with HCl, then extracted with ethyl acetate and washed with brine, dried and concentrated under vacuum to yield (3S)-7-(6-amino-3-chloro-2-fluorophenyl)-5-oxo-1,2,3,5,8,8a-hexahydroindolizine-3-carboxylic acid as a yellow solid. LC/MS: mass calculated for $C_{15}H_{14}ClFN_2O_3$: 324.07, measured: 325.05 $[M+H]^+$.

Example 2: Intermediate 2 Compound of Formula (V-A)

Methyl (3S)-5,7-dioxooctahydroindolizine-3-carboxylate

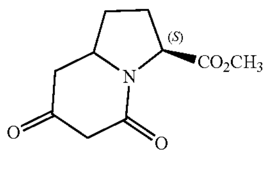

Step 1: Synthesis of methyl (2S)-5-allylpyrrolidine-2-carboxylate 1-(tert-Butyl) 2-methyl (2S)-5-allylpyrrolidine-1,2-dicarboxylate (10 g, 37.128 nmol, 1.0 eq) was dissolved in HCl solution (90 mL, 10 eq) (4 M in 1,4-dioxane). The resulting mixture was maintained for 2 h at room temperature with stirring. The solvent was removed under reduced pressure to yield methyl (2S)-5-allylpyrrolidine-2-carboxylate, which was used in the next step without further purification.

Step 2: Synthesis of methyl (2S)-1-acryloyl-5-allylpyrrolidine-2-carboxylate

At −78° C., to a solution of methyl (2S)-5-allylpyrrolidine-2-carboxylate (6 g, 35.457 mmol, 1.0 eq) in THF (200 mL) was added TEA (23 mL, 177.283 mmol, 5.0 eq) followed by addition of acryloyl chloride (3.2 g, 35.457 mmol, 1.0 eq). The resulting mixture was maintained for 40 min at room temperature with stirring. The reaction was quenched with $NH_4Cl$ (aq.) and the resulting layers separated. The aqueous phase was extracted with ethyl acetate. The organic layer was dried over $Na_2SO_4$, filtered and concentrated. The resulting residue obtained was purified by silica gel chromatography (EtOAc/PE) to yield methyl (2S)-1-acryloyl-5-allylpyrrolidine-2-carboxylate as a yellow oil.

Step 3: Synthesis of methyl (3S)-5-oxo-1,2,3,5,8,8a-hexahydroindolizine-3-carboxylate Under $N_2$, to a solution of methyl (2S)-1-acryloyl-5-allylpyrrolidine-2-carboxylate (7.2 g, 32.248 mmol, 1.0 eq) in DCM (100 mL) was added Grubbs' 2nd generation catalyst (2.7 g, 3.225 mmol, 0.1 eq). The resulting mixture was heated at 45° C. for 10 h. The solvent was removed under reduced pressure and the resulting residue was purified by silica gel column chromatography (EA/PE) to yield methyl (3S)-5-oxo-1,2,3,5,8,8a-hexahydroindolizine-3-carboxylate as a brown oil.

Step 4: Synthesis of (3S)-methyl 7-hydroxy-5-oxo-octahydroindolizine-3-carboxylate Under $N_2$, to a solution of CuCl (0.102 g, 1.025 mmol, 0.2 eq) in THF (100 mL) was added BINAP (0.638 g, 1.025 mmol, 0.2 eq). The resulting mixture was maintained for 15 min at room temperature with stirring. t-BuONa (0.098 g, 1.025 mmol, 0.2 eq) was added to the mixture. After 30 min of stirring, 4,4,4',4',5,5,5',5'-octamethyl-2,2'-bi(1,3,2-dioxaborolane) (1.561 g, 6.147 mmol, 1.2 eq) was added to the mixture, followed by addition of (3S)-methyl 5-oxo-1,2,3,5,8,8a-hexahydroindolizine-3-carboxylate (1 g, 5.123 mmol, 1.0 eq). MeOH (0.328 g, 10.245 mmol, 2.0 eq) was then added dropwise. The resulting mixture was stirred for 16 h at room temperature, then cooled down to 0° C. $H_2O_2$ was then added (6 mL, 51.226 mmol, 10 eq) and the resulting mixture was stirred for another 1 h. The solvent was removed under reduced pressure and the residue was purified by silica gel column chromatography (DCM/MeOH) to yield (3S)-methyl 7-hydroxy-5-oxo-octahydroindolizine-3-carboxylate as a brown oil.

Step 5: Synthesis of (3S)-methyl 5,7-dioxo-octahydroindolizine-3-carboxylate

To a solution of (3S)-methyl 7-hydroxy-5-oxo-octahydroindolizine-3-carboxylate (1 g) in DCM (100 mL) was added pyridinium chlorochromate (2 g, 9.38 mmol, 2.0 eq). The resulting mixture was stirred for 16 h at room temperature. The solvent was removed under reduced pressure and the residue was purified by silica gel column chromatography (EA/PE) to yield (3S)-methyl 5,7-dioxo-octahydroindolizine-3-carboxylate as a yellow oil.

Example 3: Intermediate 3 Compound of Formula (VI-A)

Methyl (3S,8aR)-5-oxo-7-(((trifluoromethyl)sulfonyl)oxy)-1,2,3,5,8,8a-hexahydroindolizine-3-carboxylate

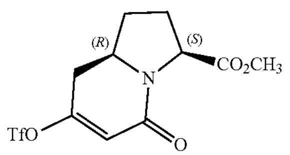

Step 1: Synthesis of 7-benzyl 1-methyl (S)-2-((tert-butoxycarbonyl)amino)-5-oxoheptanedioate Into a 10-L 3-necked round-bottom flask purged and maintained with an inert atmosphere of nitrogen, was added 1M LDA in THF (1132.2 mL, 1.00 equiv.), solvent THF (3400.00 mL), followed by the dropwise addition of a solution of benzyl acetate (170.00 g, 1131.998 mmol, 1.00 equiv.) in THF (850.0 mL) with stirring at −78° C. The resulting solution was stirred for 30 min at −78° C. To the solution was then added a solution of 1-tert-butyl 2-methyl (2S)-5-oxopyrrolidine-1,2-dicarboxylate (275.37 g, 1131.998 mmol, 1.00 equiv.) in THF (850.0 mL) dropwise, with stirring at −78° C. The resulting solution was maintained with stirring overnight at room temperature and then quenched by the addition of 5000 mL of $NH_4Cl$. The resulting solution was extracted with ethyl acetate (3×4000 mL). The resulting mixture was washed with brine (1×1000 mL). The resulting mixture was dried over anhydrous sodium sulfate and concentrated under vacuum. The residue was purified by silica gel column eluted with ethyl acetate/petroleum ether (1:9) to yield 7-benzyl 1-methyl (2S)-2-[(tert-butoxycarbonyl)amino]-5-oxoheptanedioate as a yellow oil.

Step 2: Synthesis of methyl (S,Z)-5-(2-(benzyloxy)-2-oxoethylidene)pyrrolidine-2-carboxylate Into a 5000-mL round-bottom flask purged and maintained with an inert atmosphere of nitrogen, was added 7-benzyl 1-methyl (2S)-2-[(tert-butoxycarbonyl)amino]-5-oxoheptanedioate (290.00 g, 1.00 equiv.) and TFA (469.50 g, 6.00 equiv.). The resulting solution was stirred for 2 h at room temperature and then concentrated under vacuum to remove most of TFA. The pH value of the solution was adjusted to 8 with $Na_2CO_3$. The resulting solution was extracted with DCM (3×500 mL). The combined organic phase was washed with brine (1×500 mL). The mixture was dried over anhydrous sodium sulfate and concentrated under vacuum to yield methyl(2S,5Z)-5-[2-(benzyloxy)-2-oxoethylidene]pyrrolidine-2-carboxylate as a semi-solid.

Step 3: Synthesis of 1-(tert-butyl) 2-methyl (2S,5R)-5-(2-(benzyloxy)-2-oxoethyl)pyrrolidine-1,2-dicarboxylate Into a 5000-mL autoclave, was placed methyl (2S,5Z)-5-[2-(benzyloxy)-2-oxoethylidene] pyrrolidine-2-carboxylate (175.00 g, 635.661 mmol, 1.00 equiv.), MeOH (3500.00 mL), $(Boc)_2O$ (138.73 g, 635.661 mmol, 1.00 equiv.), and $PtO_2$ (43.30 g, 190.698 mmol, 0.30 equiv.). The resulting mixture was reacted under hydrogen atmosphere (15 atm). The resulting solution was stirred for 12 h at 35° C. The precipitate was filtered off and the filtrate was concentrated to yield 1-(tert-butyl) 2-methyl (2S,5R)-5-(2-(benzyloxy)-2-oxoethyl)pyrrolidine-1,2-dicarboxylate, which was used in next step directly.

Step 4: Synthesis of methyl (2S,5R)-5-(2-(benzyloxy)-2-oxoethyl)pyrrolidine-2-carboxylate hydrochloride Into a 5000-mL round-bottom flask purged and maintained with an inert atmosphere of nitrogen, was placed 1-tert-butyl 2-methyl (2S,5R)-5-[2-(benzyloxy)-2-oxoethyl] pyrrolidine-1,2-dicarboxylate (244.00 g, 1.00 equiv.), DCM (2440.00 mL) and HCl (gas) in 1,4-dioxane (220.00 g, 4.000 mmol, 5.00 equiv.). The resulting solution was stirred for 3 h at room temperature. The reaction was concentrated to yield methyl (2S,5R)-5-[2-(benzyloxy)-2-oxoethyl]pyrrolidine-2-carboxylate hydrochloride as a yellow oil.

Step 5: Synthesis of methyl (2S,5R)-5-(2-(benzyloxy)-2-oxoethyl)-1-(3-methoxy-3-oxopropanoyl) pyrrolidine-2-carboxylate Into a 5000-mL 3-necked round-bottom flask purged and maintained with an inert atmosphere of nitrogen, was placed methyl (2S,5R)-5-[2-(benzyloxy)-2-oxoethyl]pyrrolidine-2-carboxylate (197.00 g, 710.371 mmol, 1.00 equiv.), DMF (1970.00 mL) and 1-methyl 3-potassium propanedioate (221.89 g, 1420.741 mmol, 2.00 equiv.). This was followed by the addition of pyridine (140.48 g, 1775.927 mmol, 2.50 equiv.) at 0° C. To the resulting mixture was then added $T_3P$ (452.05 g, 1420.742 mmol, 2.00 equiv.) at 0° C. The resulting solution was stirred for 12 h at 25° C. The reaction was then quenched by the addition of water (2000 mL) and extracted with ethyl acetate (3×2000 mL). The combined organic phase was washed with brine (1×2000 mL). The mixture was dried over anhydrous sodium sulfate and concentrated. The resulting residue was purified by Flash-Prep-HPLC with the following conditions (IntelFlash-1): Column, $C_{18}$ silica gel; mobile phase, ACN-$H_2O$=45 increasing to ACN-$H_2O$=60 within 20 minutes; to yield methyl (2S, 5R)-5-[2-(benzyloxy)-2-oxoethyl]-1-(3-methoxy-3-oxopropanoyl)pyrrolidine-2-carboxylate as a yellow oil.

Step 6: Synthesis of 2-((2R,5S)-1-(3-methoxy-3-oxopropanoyl)-5-(methoxycarbonyl)pyrrolidin-2-yl) acetic acid Into a 3000-mL round-bottom flask, was placed methyl (2S,5R)-5-[2-(benzyloxy)-2-oxoethyl]-1-(3-methoxy-3-oxopropanoyl)pyrrolidine-2-carboxylate (151.00 g), IPA (1510.00 mL) and Pd/C (15.10 g). The resulting suspension was stirred for 2 h at room temperature under 2 atm $H_2$. The precipitate was filtered off and the filtrate was concentrated to yield [(2R,5S)-1-(3-methoxy-3-oxopropanoyl)-5-(methoxycarbonyl)pyrrolidin-2-yl]acetic acid as a yellow oil.

Step 7: Synthesis of dimethyl (3S,8aR)-5,7-dioxooctahydroindolizine-3,6-dicarboxylate Into a 5000-mL 3-necked round-bottom flask purged and maintained with an inert atmosphere of nitrogen, was placed [(2R,5S)-1-(3-methoxy-3-oxopropanoyl)-5-(methoxycarbonyl)pyrrolidin-2-yl] acetic acid (104.00 g, 362.031 mmol, 1.00 equiv.), THF (3120.00 mL) and CDI (88.05 g, 543.047 mmol, 1.50 equiv.). The resulting mixture was stirred for 0.5 h at room temperature. To the resulting mixture was then added DBU (82.67 g, 543.047 mmol, 1.50 equiv.). The mixture was stirred for 2 hrs. at room temperature and then quenched by the addition of water/ice (2000 mL). The pH of the solution was adjusted to pH 3 with HCl (2 mol/L). The resulting solution was extracted with DCM/MeOH=3:1 (3×1500 mL), dried over anhydrous sodium sulfate and concentrated to yield 3,6-dimethyl (3S,8aR)-5,7-dioxo-hexahydroindolizine-3,6-dicarboxylate as a light yellow oil.

Step 8: Synthesis of methyl (3S,8aR)-5,7-dioxooctahydroindolizine-3-carboxylate

Into a 3000-mL round-bottom flask was placed 3,6-dimethyl (3S,8aR)-5,7-dioxo-hexahydroindolizine-3,6-dicarboxylate (94.00 g, 1.00 equiv.) and AcOH (940.00 mL). The resulting solution was stirred for 30 min at 110° C. The resulting solution was extracted with DCM/MeOH=2:1 (3×2000 mL), dried over anhydrous sodium sulfate and concentrated to yield of methyl (3S,8aR)-5,7-dioxo-hexahydroindolizine-3-carboxylate as a yellow oil.

Step 9: Synthesis of methyl (3S,8aR)-5-oxo-7-(((trifluoromethyl)sulfonyl)oxy)-1,2,3,5,8,8a-hexahydroindolizine-3-carboxylate Into a 3000-mL round-bottom flask purged and maintained with an inert atmosphere of nitrogen, was placed methyl (3S,8aR)-5,7-dioxo-hexahydroindolizine-3-carboxylate (55.00 g, 1.00 equiv.), DCM (1100.00 mL), DIEA (67.38 g, 2.00 equiv.) and $PhNTf_2$ (111.73 g, 1.20 equiv.). The resulting solution was stirred for 4 h at room temperature. The resulting mixture was washed with $NaHCO_3$ (2×2000 mL). The resulting mixture was concentrated under vacuum and the residue was purified by silica gel with PE/EA=1/4 to yield methyl(3S,8aR)-5-oxo-7-(trifluoromethanesulfonyloxy)-1,2,3,5,8,8a-hexahydro-1H-indolizine-3-carboxylate as a white solid.

Example 4: Intermediate 4

(6-Amino-3-chloro-2-fluorophenyl)boronic acid

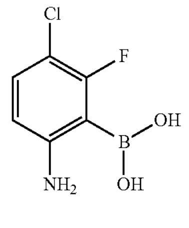 [SMILES: Nc1ccc(Cl)c(F)c1B(O)O]

Step 1: Synthesis of N-(4-chloro-3-fluorophenyl)-2,2,2-trifluoroacetamide

To a mixture of 4-chloro-3-fluorobenzenamine (20 g, 137.398 mmol, 1.00 equiv.) and $Na_2CO_3$ (24.7 g, 233.577 mmol, 1.70 equiv.) in $Et_2O$ (400 mL) was added TFAA (34.6 g, 164.878 mmol, 1.20 equiv.) dropwise, with stirring at −10° C. The resulting mixture was allowed to warm to room temperature overnight, then diluted with hexane (400 mL)

and filtered. The filtrate was washed with saturated sodium bicarbonate solution (2×200 mL), brine (2×200 mL), dried over $Na_2SO_4$, and filtered. The filtrate was concentrated to yield N-(4-chloro-3-fluorophenyl)-2,2,2-trifluoroacetamide as a white solid.

Step 2: Synthesis of 6-amino-3-chloro-2-fluorophenylboronic acid

Under an inert atmosphere of nitrogen, to a mixture of N-(4-chloro-3-fluorophenyl)-2,2,2-trifluoroacetamide (30 g, 124.188 mmol, 1.00 equiv.) in THF (500 mL) was added n-BuLi (99 mL, 248.375 mmol, 2.00 equiv., 2.5 M in hexane) dropwise with stirring at −78° C. The resulting mixture was stirred at −78° C. for 15 min, then allowed to warm to −50° C. The resulting clear brown solution was cooled to −78° C., and then $B(O\text{-}iPr)_3$ (51.3 g, 273.213 mmol, 2.20 equiv) was added dropwise. The mixture was stirred at −78° C. for 10 minutes, and then allowed to warm to room temperature. The resulting orange suspension was stirred at room temperature for 4 h, then cooled in an ice bath and quenched with 1 M HCl (300 mL). The resulting mixture was stirred at room temperature overnight, then extracted with EtOAc (300 mL×3), dried over $Na_2SO_4$, and filtered. The filtrate was concentrated and the residue was recrystallized (EtOAc/PE: 1/10) to yield 6-amino-3-chloro-2-fluorophenylboronic acid as a white solid.

Example 5: Compound of Formula (I-A)

(3S,8aR)-7-(3-Chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one

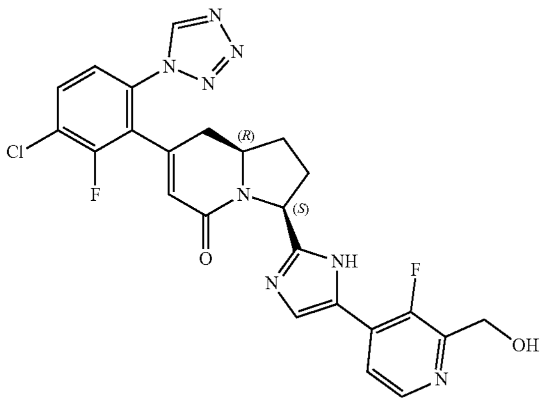

Step 1: Synthesis of 2-(((tert-butyldimethylsilyl)oxy)methyl)-3-fluoropyridine

To a solution of (3-fluoropyridin-2-yl)methanol (15.0 g, 118.002 mmol, 1.0 eq.) in DMF (200 mL) was added imidazole (16.1 g, 236.496 mmol, 2.0 eq.) followed by addition of tert-butylchlorodimethylsilane (21.3 g, 141.320 mmol, 1.2 eq.). The mixture was stirred at room temperature overnight. The reaction was quenched with water (200 mL). The resulting mixture was extracted with ethyl acetate (3×400 mL) then washed with water (3×200 mL). The organic layers were combined, dried over anhydrous sodium sulfate, filtered and concentrated. The resulting residue was purified by silica gel chromatography (0-30% PE/EA) to yield 2-(((tert-butyldimethylsilyl)oxy)methyl)-3-fluoropyridine as a yellow oil. LC/MS: mass calculated for $C_{12}H_{20}FNOSi$: 241.13, measured: 242.10 $[M+H]^+$.

Step 2: Synthesis of 2-(((tert-butyldimethylsilyl)oxy)methyl)-3-fluoro-4-iodopyridine To a solution of 2-(((tert-butyldimethylsilyl)oxy)methyl)-3-fluoropyridine (24.0 g, 99.430 mmol, 1.0 eq.) in THF (400 mL) was added LDA (59.7 mL, 119.4 mmol, 1.2 eq.) at −78° C. The mixture was stirred at −78° C. for 0.5 h. To the resulting mixture was then added a solution of iodine (30.3 g, 119.381 mmol, 1.2 eq.) in THF (60 mL) at −78° C. The mixture was stirred at −78° C. for 3 h. The reaction was quenched with $NH_4Cl$ solution (200 mL) and extracted with ethyl acetate (3×400 mL). The combined extracts were washed with water, dried over $Na_2SO_4$, filtered and concentrated. The resulting residue was purified by silica gel chromatography (0-30% EA/PE) to yield 2-(((tert-butyldimethylsilyl)oxy)methyl)-3-fluoro-4-iodopyridine as a white solid. LC/MS: mass calculated for $C_{12}H_{19}FINOSi$: 367.03, measured: 368.20 $[M+H]^+$.

Step 3: Synthesis of 2-(((tert-butyldimethylsilyl)oxy)methyl)-4-(1-ethoxyvinyl)-3-fluoropyridine To a solution of 2-(((tert-butyldimethylsilyl)oxy)methyl)-3-fluoro-4-iodopyridine (20.0 g, 54.455 mmol, 1.0 eq.) and bis(triphenylphosphine)palladium(II) chloride (3.8 g, 5.414 mmol, 0.1 eq.) in 1,4-dioxane (200 mL) was added tributyl (1-ethoxyvinyl)stannane (29.5 g, 81.683 mmol, 1.5 eq.). The mixture was stirred at 90° C. for 2 h. After cooling down to room temperature, the reaction was quenched with water (200 mL), then extracted with ethyl acetate (3×300 mL). The organic layers were combined, dried over anhydrous sodium sulfate, filtered and concentrated. The resulting residue was purified by $Al_2O_3$ chromatography (0-50% ethyl acetate/petroleum ether) to yield 2-(((tert-butyldimethylsilyl)oxy)methyl)-4-(1-ethoxyvinyl)-3-fluoropyridine as a yellow oil. LC/MS: mass calculated for $C_{16}H_{26}FNO_2Si$: 311.17, measured 312.15 $[M+H]^+$.

Step 4: Synthesis of 2-bromo-1-(2-(((tert-butyldimethylsilyl)oxy)methyl)-3-fluoropyridin-4-yl)ethan-1-one To a mixture of 2-(((tert-butyldimethylsilyl)oxy)methyl)-4-(1-ethoxyvinyl)-3-fluoropyridine (15 g, 48.159 mmol, 1.0 equiv.) in THF (120 mL) and $H_2O$ (30 mL) was added NBS (8.6 g, 48.319 mmol, 1.0 equiv.). The reaction was stirred at room temperature for 2 h. The resulting mixture was then diluted with EtOAc (700 mL), washed with brine (3×200 mL), dried over $Na_2SO_4$, and concentrated to yield 2-bromo-1-(2-(((tert-butyldimethylsilyl)oxy)methyl)-3-fluoropyridin-4-yl)ethan-1-one as an off-white solid. LC/MS: mass calculated for $C_{14}H_{21}BrFNO_2Si$: 361.05, measured: 362.00 $[M+H]^+$.

Step 5: Synthesis of 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate A mixture of (3S)-7-(6-amino-3-chloro-2-fluorophenyl)-5-oxo-1,2,3,5,8,8a-hexahydroindolizine-3-carboxylic acid (9.3 g, 28.64 mmol, 1.0 equiv.) and $Cs_2CO_3$ (5.6 g, 17.18 mmol, 0.6 equiv.) in DMF (90 mL) was stirred at 40° C. for 30 min. 2-Bromo-1-(2-(((tert-butyldimethylsilyl)oxy) methyl)-3-fluoropyridin-4-yl)ethan-1-one (14.5 g, 40.09 mmol, 1.4 equiv.) was then added and the mixture was stirred at room temperature for 4 h. The resulting mixture was diluted with EtOAc (900 mL), washed with water (3×150 mL), brine (2×150 mL), dried over $Na_2SO_4$ and concentrated. The resulting residue was applied onto a silica gel column (330 g, MeOH/DCM: 1/20) to yield 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate as a light yellow solid. LC/MS: mass calculated for $C_{29}H_{34}ClF_2N_3O_5Si$: 605.19, measured: 606.15 $[M+H]^+$.

Step 6: Synthesis of (3S)-7-(6-amino-3-chloro-2-fluorophenyl)-3-(5-(2-(((tert-butyldimethylsilyl)oxy) methyl)-3-fluoropyridin-4-yl)-1H-imidazol-2-yl)-2,3,8,8a-tetrahydroindolizin-5(1H)-one Under an inert atmosphere of nitrogen, a mixture of 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate (15.0 g, 24.75 mmol, 1.0 equiv.) and $NH_4OAc$ (19.1 g, 247.47 mmol, 10.0 equiv.) in AcOH (30 mL) and toluene (300 mL) was stirred at 110° C. for 1 h. The resulting mixture was concentrated under reduced pressure. The residue was applied onto a silica gel column (330 g, MeOH/DCM: 1/15) to yield (3S)-7-(6-amino-3-chloro-2-fluorophenyl)-3-(5-(2-((tert-butyldimethylsilyloxy)methyl)-3-fluoropyridin-4-yl)-1H-imidazol-2-yl)-2,3,8,8a-tetrahydroindolizin-5(1H)-one as a light yellow solid. LC/MS: mass calculated for $C_{29}H_{34}ClF_2N_5O_2Si$: 585.21, measured: 586.15 $[M+H]^+$.

Step 7: Synthesis of (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one A mixture of (3S)-7-(6-amino-3-chloro-2-fluorophenyl)-3-(5-(2-((tert-butyldimethylsilyloxy)methyl)-3-fluoropyridin-4-yl)-1H-imidazol-2-yl)-2,3,8,8a-tetrahydroindolizin-5(1H)-one (8 g, 13.648 mmol, 1.00 equiv.), $TMSN_3$ (15.724 g, 136.484 mmol, 10.00 equiv.) and trimethoxymethane (14.484 g, 136.484 mmol, 10.00 equiv.) in AcOH (60 mL) was stirred at 55° C. overnight. The resulting mixture was concentrated under reduced pressure. The residue was applied onto a C18 reverse phase column (330 g, ACN/$H_2O$ (0.05% $NH_4HCO_3$): 5%>>>35%>>>40%) to yield (3S)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one as a white solid. The white solid was further purified by Prep-SFC(Column: Exsil Chiral-NR, 250 mm*30 mm, 8 um; Mobile Phase A: $CO_2$, Mobile Phase B: MeOH (0.1% 2M $NH_3$-MeOH); Flow rate: 100 mL/min; Gradient: 50% B; 220 nm; RT1:6.78; RT2: 8.45; Injection Volume: 3 ml; Number Of Runs: 37;) to yield (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one as a white solid.

$^1H$ NMR (400 MHz, DMSO-$d_6$) δ 12.25 (s, 1H), 9.82 (s, 1H), 8.32 (d, J=5.0 Hz, 1H), 7.95 (t, J=8.7 Hz, 1H), 7.88 (t, J=5.4 Hz, 1H), 7.70 (d, J=8.7 Hz, 1H), 7.55 (d, J=3.9 Hz, 1H), 5.68 (d, J=2.6 Hz, 1H), 5.26 (t, J=5.9 Hz, 1H), 5.02 (d, J=8.7 Hz, 1H), 4.61 (dd, J=5.9, 2.3 Hz, 2H), 3.68-3.75 (m, 1H), 2.67-2.75 (m, 1H), 2.52-2.54 (m, 1H), 2.14-2.21 (m, 1H), 2.05-2.11 (m, 1H), 1.93-1.97 (m, 2H); $^{19}F$ NMR (376 MHz, DMSO-$d_6$) δ −112.85, −130.14; LC/MS: mass calculated for $C_{24}H_{19}ClF_2N_8O_2$: 524.13, measured: 525.10 $[M+H]^+$.

Example 6: Compound of Formula (I-B)

(3S,8aR)-7-(3-Chloro-2-fluoro-6-(1H-tetrazol-1-yl) phenyl)-3-(5-(3-fluoro-2-(hydroxymethyl)pyridin-4-yl)-1H-imidazol-2-yl-4-d)-2,3,8,8a-tetrahydroindolizin-5(1H)-one

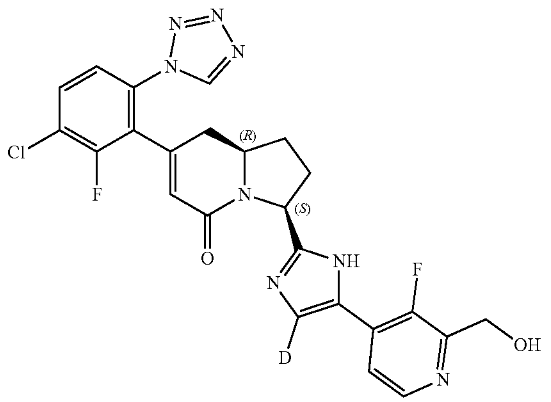

Step 1: Synthesis of (3S,8aR)-7-(3-chloro-2-fluoro-6-(1H-tetrazol-1-yl)phenyl)-3-(5-(3-fluoro-2-(hydroxymethyl)pyridin-4-yl)-4-iodo-1H-imidazol-2-yl)-2,3,8,8a-tetrahydroindolizin-5(1H)-one A mixture of (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one (180 mg, 0.343 mmol, 1.0 equiv.) and NIS (77 mg, 0.342 mmol, 1.0 equiv.) in DMF (8 mL) was stirred at room temperature for 2 h. The resulting mixture was diluted with EtOAc (80 mL), washed with water (4×20 mL), brine (2×20 mL), dried over $Na_2SO_4$, and concentrated. The residue was applied onto a silica gel column (40 g, MeOH/DCM: 1/15) to yield (3S,8aR)-7-(3-chloro-2-fluoro-6-(1H-tetrazol-1-yl) phenyl)-3-(5-(3-fluoro-2-(hydroxymethyl)pyridin-4-yl)-4-iodo-1H-imidazol-2-yl)-2,3,8,8a-tetrahydroindolizin-5(1H)-one as a light yellow solid. LC/MS: mass calculated for $C_{24}H_{18}ClF_2IN_8O_2$: 650.03, measured: 650.95 $[M+H]^+$.

Step 2: Synthesis of (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl-4-d)-2,3,8,8a-tetrahydroindolizin-5(1H)-one A mixture of (3S,8aR)-7-(3-chloro-2-fluoro-6-(1H-tetrazol-1-yl)phenyl)-3-(5-(3-fluoro-2-(hydroxymethyl)pyridin-4-yl)-4-iodo-1H-imidazol-2-yl)-2,3,8,8a-tetrahydroindolizin-5(1H)-one (210 mg, 0.323 mmol, 1.0 equiv.) and Zn (211 mg, 3.226 mmol, 10.0 equiv.) in $CD_3COOD$ (8 mL) and $D_2O$ (4 mL) was stirred at room temperature for 10 min. The resulting mixture was filtered, and the filtrate concentrated. The residue was applied onto a C18 reverse phase column (330 g, ACN/$H_2O$ (0.05% $NH_4HCO_3$):

5%>>>40%>>>40%) to yield (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl-4-d)-2,3,8,8a-tetrahydroindolizin-5(1H)-one as a light yellow solid.

$^1$H NMR (400 MHz, DMSO-$d_6$) δ 12.30 (br, 1H), 9.84 (s, 1H), 8.30-8.40 (m, 1H), 7.97 (t, J=7.9 Hz, 1H), 7.89 (t, J=5.4 Hz, 1H), 7.71 (dd, J=8.7, 1.5 Hz, 1H), 5.70 (d, J=2.7 Hz, 1H), 5.13-5.50 (m, 1H), 5.05 (d, J=8.7 Hz, 1H), 4.64 (s, 2H), 3.65-3.83 (m, 1H), 2.62-2.83 (m, 1H), 2.53-2.60 (m, 1H), 2.05-2.30 (m, 2H), 1.83-2.04 (m, 2H); $^{19}$F NMR (376 MHz, DMSO-$d_6$) δ −112.51, −130.07; LC/MS: mass calculated for $C_{24}H_{18}ClDF_2N_8O_2$: 525.14, measured: 526.15 $[M+H]^+$.

Example 7A: Compound of Formula (I-C)

(3S,8aR)-7-(3-Chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one

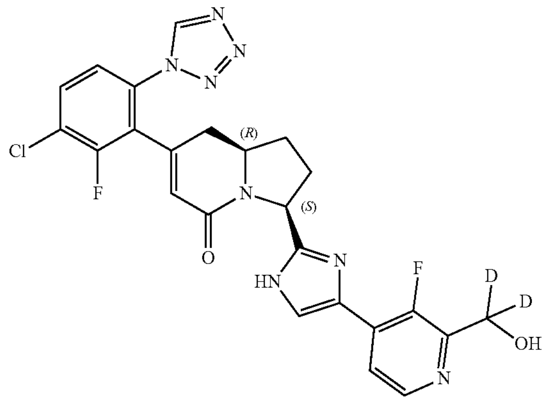

Step 1: Synthesis of (3-fluoropyridin-2-yl)methan-d2-ol

To a mixture of methyl 3-fluoropicolinate (5 g, 32.232 mmol, 1.00 equiv) in EtOH (80 mL) was added $NaBD_4$ (4.0 g, 96.696 mmol, 3.0 equiv) in portions at 0° C. The resulting mixture was stirred at room temperature for 2 h. The reaction was then quenched with saturated ammonium chloride solution (60 mL). The EtOH solvent was removed through reduced pressure evaporation by ROTOVAP. The resulting mixture was then extracted with EtOAc (3×100 mL), dried over $Na_2SO_4$, and concentrated to yield (3-fluoropyridin-2-yl)methan-d2-ol as a light yellow solid.

Step 2: Synthesis of 2-(((tert-butyldimethylsilyl)oxy)methyl-d2)-3-fluoropyridine To a mixture of (3-fluoropyridin-2-yl)methan-d2-ol (3.2 g, 24.781 mmol, 1.0 equiv) and TBSCl (5.6 g, 37.172 mmol, 1.5 equiv) in DMF (60 mL) was added $Et_3N$ (7.5 g, 74.344 mmol, 3.0 equiv). The resulting mixture was then stirred at room temperature for 5 h. The resulting mixture was diluted with EtOAc (600 mL), washed with water (3×150 mL), brine (2×150 mL), dried over $Na_2SO_4$, and concentrated. The residue was applied onto a silica gel column (80 g, EtOAc/PE: 1/3) to yield 2-(((tert-butyldimethylsilyl)oxy)methyl-d2)-3-fluoropyridine as light yellow solid. LC/MS: mass calculated for $C_{12}H_{18}D_2FNOSi$: 243.14, measured: 244.10 $[M+H]^+$.

Step 3: Synthesis of 2-(((tert-butyldimethylsilyl)oxy)methyl-d2)-3-fluoro-4-iodopyridine Under an inert atmosphere of nitrogen, to a mixture of 2-(((tert-butyldimethylsilyl)oxy)methyl-d2)-3-fluoropyridine (4.8 g, 19.721 mmol, 1.00 equiv) in THF (120 mL) was added LDA (11.8 mL, 23.666 mmol, 1.2 equiv, 2M in THF) at −78° C., and the resulting mixture was stirred at −78° C. for 30 min. To the resulting mixture was then added a solution of 12 (5.5 g, 21.694 mmol, 1.1 equiv) in THF (25 mL) at −78° C. The mixture was stirred at −78° C. for 2 h. The resulting mixture was quenched with saturated ammonium chloride solution (200 mL), extracted with EtOAc (3×200 mL), dried over $Na_2SO_4$, and concentrated. The residue was applied onto a silica gel column (80 g, EtOAc/PE: 1/4) to yield 2-(((tert-butyldimethylsilyl)oxy)methyl-d2)-3-fluoro-4-iodopyridine as a light yellow solid.

Step 4: Synthesis of 2-(((tert-butyldimethylsilyl)oxy)methyl-d2)-4-(1-ethoxyvinyl)-3-fluoropyridine Under an inert atmosphere of nitrogen, a mixture of 2-(((tert-butyldimethylsilyl)oxy)methyl-d2)-3-fluoro-4-iodopyridine (2.7 g, 7.311 mmol, 1.0 equiv), tributyl(1-ethoxyvinyl)stannane (5.3 g, 14.623 mmol, 2.0 equiv) and $Pd(PPh_3)_4$ (845 mg, 0.731 mmol, 0.1 equiv) in 1,4-dioxane (50 mL) was stirred at 100° C. overnight. The resulting mixture was concentrated and the residue was applied onto a silica gel column (80 g, EtOAc/PE: 1/3) to yield 2-(((tert-butyldimethylsilyl)oxy)methyl-d2)-4-(1-ethoxyvinyl)-3-fluoropyridine as a yellow solid. LC/MS: mass calculated for $C_{16}H_{24}D_2FNO_2Si$: 313.18, measured: 314.10 $[M+H]^+$.

Step 5: Synthesis of 2-bromo-1-(2-(((tert-butyldimethylsilyl)oxy)methyl-d2)-3-fluoropyridin-4-yl)ethan-1-one To a mixture of 2-(((tert-butyldimethylsilyl)oxy)methyl-d2)-4-(1-ethoxyvinyl)-3-fluoropyridine (2.5 g, 7.975 mmol, 1.0 equiv) in THF (60 mL) and $H_2O$ (20 mL) was added NBS (1.4 g, 7.975 mmol, 1.0 equiv). The reaction was stirred at room temperature for 1 h. The resulting mixture was diluted then with EtOAc (500 mL), washed with brine (3×100 mL), dried over $Na_2SO_4$, and concentrated to yield 2-bromo-1-(2-(((tert-butyldimethylsilyl)oxy)methyl-d2)-3-fluoropyridin-4-yl)ethan-1-one as s light yellow oil.

Step 6: Synthesis of 2-(2-(((tert-butyldimethylsilyl)oxy)methyl-d2)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate A mixture of (3S)-7-(6-amino-3-chloro-2-fluorophenyl)-5-oxo-1,2,3,5,8,8a-hexahydroindolizine-3-carboxylic acid (2.4 g, 7.391 mmol, 1.0 equiv) and $Cs_2CO_3$ (1.4 g, 4.434 mmol, 0.6 equiv) in DMF (60 mL) was stirred at 40° C. for 30 min. 2-Bromo-1-(2-(((tert-butyldimethylsilyl)oxy)methyl-d2)-3-fluoropyridin-4-yl)ethan-1-one (2.7 g, 7.391 mmol, 1.0 equiv) was then added and the mixture stirred at room temperature for 4 h. The resulting mixture was then diluted with EtOAc (500 mL), washed with water (3×100 mL), brine (2×100 mL), dried over $Na_2SO_4$, and concentrated. The residue was applied onto a silica gel column (80 g, MeOH/DCM: 1/20) to yield 2-(2-(((tert-butyldimethylsilyl)oxy)methyl-d2)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate as yellow solid. LC/MS: mass calculated for $C_{29}H_{32}ClD_2F_2N_3O_5Si$: 607.20, measured: 608.15 $[M+H]^+$.

Step 7: Synthesis of (3S)-7-(6-amino-3-chloro-2-fluorophenyl)-3-(4-(2-(((tert-butyldimethylsilyl)oxy) methyl-d2)-3-fluoropyridin-4-yl)-1H-imidazol-2-yl)-2,3,8,8a-tetrahydroindolizin-5(1H)-one Under an inert atmosphere of nitrogen, a mixture of 2-(2-(((tert-butyldimethylsilyl)oxy)methyl-d2)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate (3.5 g, 5.755 mmol, 1.0 equiv) and $NH_4OAc$ (3.5 g, 46.042 mmol, 8.0 equiv) in AcOH (10 mL) and toluene (100 mL) was stirred at 110° C. for 1 h. The resulting mixture was concentrated. The residue was applied onto a silica gel column (80 g, MeOH/DCM: 1/15) to yield (3S)-7-(6-amino-3-chloro-2-fluorophenyl)-3-(4-(2-(((tert-butyldimethylsilyl)oxy)methyl-d2)-3-fluoropyridin-4-yl)-1H-imidazol-2-yl)-2,3,8,8a-tetrahydroindolizin-5(1H)-one as a light yellow solid. LC/MS: mass calculated for $C_{29}H_{32}ClD_2F_2N_5O_2Si$: 587.23, measured: 588.15 $[M+H]^+$.

Step 8: Synthesis of (3S,8aR)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one A mixture of (3S)-7-(6-amino-3-chloro-2-fluorophenyl)-3-(4-(2-(((tert-butyldimethylsilyl)oxy)methyl-d2)-3-fluoropyridin-4-yl)-1H-imidazol-2-yl)-2,3,8,8a-tetrahydroindolizin-5(1H)-one (2.8 g, 4.761 mmol, 1.0 equiv), $TMSN_3$ (5.5 g, 47.606 mmol, 10.0 equiv) and trimethoxymethane (5.1 g, 47.606 mmol, 10.0 equiv) in AcOH (50 mL) was stirred at 55° C. overnight. The resulting mixture was concentrated. The residue was applied onto a $C_{18}$ reverse phase column (330 g, $ACN/H_2O$ (0.05% $NH_4HCO_3$): 5%>>>35%>>>40%) to yield (3S)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one as a white solid. The white solid was further purified by Prep-SFC(Column: Exsil Chiral-NR, 250 mm*30 mm, 8 um; Mobile Phase A: $CO_2$, Mobile Phase B: MeOH (0.5% 2M $NH_3$-MeOH)—HPLC; Flow rate: 100 mL/min; Gradient: 45% B; 220 nm; RT1:9.02; RT2:11.5; Injection Volume: 4.8 ml; Number Of Runs: 13;) to yield (3S,8aR)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one as a white solid.

$^1H$ NMR (400 MHz, DMSO-$d_6$) δ 12.27 (s, 1H), 9.85 (s, 1H), 8.35 (d, J=5.0 Hz, 1H), 7.98 (t, J=8.0 Hz, 1H), 7.90 (t, J=5.4 Hz, 1H), 7.72 (dd, J=8.7, 1.5 Hz, 1H), 7.58 (d, J=1.6 Hz, 1H), 5.71 (d, J=2.8 Hz, 1H), 5.24 (s, 1H), 5.05 (d, J=8.7 Hz, 1H), 3.65-3.84 (m, 1H), 2.73 (t, J=15.4 Hz, 1H), 2.54-2.62 (m, 1H), 2.17-2.30 (m, 1H), 2.06-2.16 (m, 1H), 1.89-2.05 (m, 2H); $^{19}F$ NMR (376 MHz, DMSO-$d_6$) δ −112.85, −130.23; LC/MS: mass calculated for $C_{24}H_{17}ClD_2F_2N_8O_2$: 526.14, measured: 527.05 $[M+H]^+$.

Example 7B: Compound of Formula (I-C)

(3S,8aR)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one

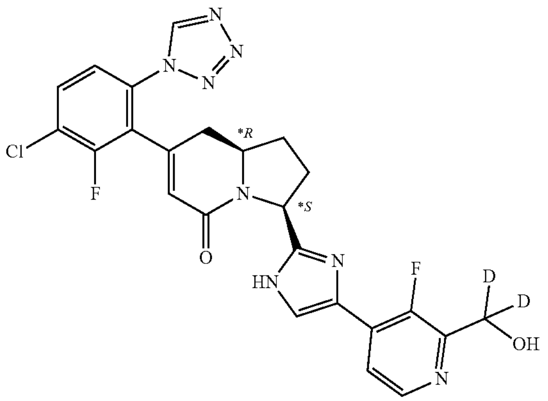

Step 1: 2-(2-(((tert-butyldimethylsilyl)oxy)methyl-d2)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate A mixture of ((3S)-7-(6-amino-3-chloro-2-fluorophenyl)-5-oxo-1,2,3,5,8,8a-hexahydroindolizine-3-carboxylic acid (260 mg, 0.80 mmol, 1.0 equiv.) and $Cs_2CO_3$ (156 mg, 0.48 mmol, 0.6 equiv.) in DMF (12 mL) was stirred at 40° C. for 30 min. 2-Bromo-1-(2-(((tert-butyldimethylsilyl)oxy)methyl-d2)-3-fluoropyridin-4-yl)ethan-1-one (437 mg, 1.20 mmol, 1.5 equiv.) was then added to the mixture. The reaction mixture was stirred at room temperature for 4 h. The resulting mixture was then diluted with EA (120 mL), washed with water (3×30 mL), brine (2×20 mL), dried over $Na_2SO_4$, and concentrated. The residue was purified by flash column chromatography on silica gel (0-10% MeOH/DCM) to yield 2-(2-(((tert-butyldimethylsilyl)oxy)methyl-d2)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{29}H_{32}ClD_2F_2N_3O_5Si$: 607.20, measured: 608.10 $[M+H]^+$.

Step 2: (3S)-7-(6-amino-3-chloro-2-fluorophenyl)-3-(4-(3-fluoro-2-(hydroxymethyl-d2)pyridin-4-yl)-1H-imidazol-2-yl)-2,3,8,8a-tetrahydroindolizin-5(1H)-one A mixture of 2-(2-(((tert-butyldimethylsilyl)oxy)methyl-d2)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate (280 mg, 0.46 mmol, 1.0 equiv.) and $NH_4OAc$ (355 mg, 4.60 mmol, 10.0 equiv.) in AcOH (3 mL) and toluene (30 mL) was stirred at 110° C. for 1 h, then cooled to room temperature, and concentrated under reduced pressure. The residue was purified by flash column chromatography on silica gel (0→9% MeOH/DCM) to yield (3S)-7-(6-amino-3-chloro-2-fluorophenyl)-3-(4-(3-fluoro-2-(hydroxymethyl-$d_2$)pyridin-4-yl)-1H-imidazol-2-yl)-2,3,8,8a-tetrahydroindolizin-5(1H)-one as a yellow solid. LC/MS: mass calculated for $C_{23}H_{18}ClD_2F_2N_5O_2$: 473.14, measured: 474.05 [M+H]$^+$.

Step 3: (3S,8aR)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one A mixture of ((3S)-7-(6-amino-3-chloro-2-fluorophenyl)-3-(4-(3-fluoro-2-(hydroxymethyl-d2)pyridin-4-yl)-1H-imidazol-2-yl)-2,3,8,8a-tetrahydroindolizin-5(1H)-one (200 mg, 0.422 mmol, 1.00 equiv), $TMSN_3$ (486 mg, 4.22 mmol, 10.0 equiv.) and trimethoxymethane (448 mg, 4.22 mmol, 10.0 equiv.) in AcOH (10 mL) was stirred at 50° C. for 4 h, then concentrated under reduced pressure. The residue was purified by flash column chromatography on silica gel (0→10% MeOH/DCM) to yield (3S)-7-(3-chloro-2-fluoro-6-(1H-tetrazol-1-yl)phenyl)-3-(4-(3-fluoro-2-(hydroxymethyl-$d_2$)pyridin-4-yl)-1H-imidazol-2-yl)-2,3,8,8a-tetrahydroindolizin-5(1H)-one as a light yellow solid, which was further purified by chiral-HPLC with to yield (3S,8aR)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one as a white solid.

LC/MS: mass calculated for $C_{24}H_{17}ClD_2F_2N_8O_2$: 526.14, measured (ES, m/z): 527.05 [M+H]$^+$. $^1$H NMR (400 MHz, DMSO-d6) d 12.27 (s, 1H), 9.85 (s, 1H), 8.35 (d, J=5.0 Hz, 1H), 7.98 (t, J=8.0 Hz, 1H), 7.90 (t, J=5.4 Hz, 1H), 7.72 (dd, J=8.7, 1.5 Hz, 1H), 7.58 (d, J=1.6 Hz, 1H), 5.71 (d, J=2.8 Hz, 1H), 5.24 (s, 1H), 5.05 (d, J=8.7 Hz, 1H), 3.65-3.84 (m, 1H), 2.73 (t, J=15.4 Hz, 1H), 2.54-2.62 (m, 1H), 2.17-2.30 (m, 1H), 2.06-2.16 (m, 1H), 1.89-2.05 (m, 2H). $^{19}$F NMR (376 MHz, DMSO-d6) d −112.85, −130.23

Example 8: Compound of Formula (I-D)

(3S,8aR)-7-(3-Chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8a-d

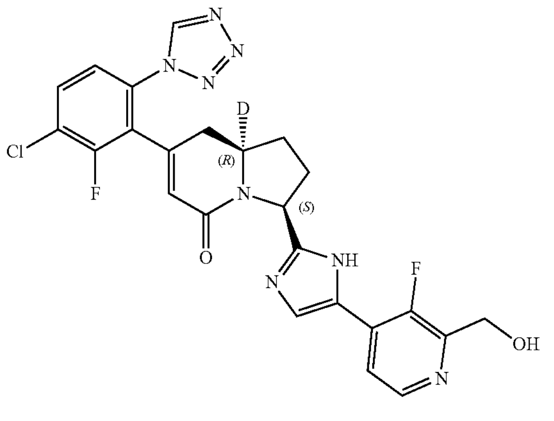

Step 1: 2-(2-(((Tert-butyldimethylsilyl)oxy)methyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate-8a-d To a solution of (3S)-7-(3-chloro-2-fluoro-6-(1H-tetrazol-1-yl)phenyl)-5-oxo-1,2,3,5,8,8a-hexahydroindolizine-3-carboxylic-8a-d acid (300 mg, 0.80 mmol, 1.0 equiv.) in $CH_3CN$ (10 mL) was added $K_2CO_3$ (142 mg, 1.03 mmol, 1.3 equiv.). After stirring at room temperature for 0.5 h, 2-bromo-1-(2-(((tert-butyldimethylsilyl)oxy)methyl)-3-fluoropyridin-4-yl)ethan-1-one (430 mg, 1.20 mmol, 1.5 equiv.) was added. The mixture was stirred at room temperature for 1 h. The resulting mixture was purified by silica gel column with MeOH/DCM (0→7%) to yield the 2-(2-(((tert-butyldimethylsilyl)oxy)methyl)-3-fluoropyridin-4-yl)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate-8a-d as a yellow oil. LC/MS: mass calculated for $C_{30}H_{32}DClF_2N_6O_5Si$: 659.20, measured (ES, m/z): 660.15 [M+H]$^+$.

Step 2: (3S)-3-(5-(2-(((Tert-butyldimethylsilyl)oxy)methyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one-8a-d To a solution of 2-(2-(((tert-butyldimethylsilyl)oxy)methyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate-8a-d (380 mg, 0.58 mmol, 1.0 equiv.) in toluene (10 mL) and acetic acid (1 mL) was added ammonium acetate (665 mg, 8.63 mmol, 15.0 equiv.). The mixture was stirred at 100° C. for 1 h. The solvent was removed under vacuum and the residue was purified by silica gel column with MeOH/DCM (0→10%) to yield (3S)-3-(5-(2-(((tert-butyldimethylsilyl)oxy)methyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one-8a-d as a yellow oil. LC/MS: mass calculated for $C_{30}H_{32}DClF_2N_8O_2Si$: 639.22, measured (ES, m/z): 640.20 [M+H]$^+$.

Step 3: (3S,8aR)-7-(3-Chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8a-d To a solution of (3S)-3-(5-(2-(((tert-butyldimethylsilyl)oxy)methyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one-8a-d (280 mg, 0.44 mmol, 1.0 equiv.) in THF (5 mL) was added triethylamine trihydrofluoride (1.3 mL). The mixture was stirred at 70° C. for 1 h. The solvent was removed under vacuum and the residue was purified by C18 column [condition: ACN-water-6.5 mM $NH_4HCO_3$+$NH_3H_2O$ (5→50%)] to yield a second residue. The second residue was purified by chiral HPLC [column: (R,R) WHELK-O1, 4.6*50 mm, 3.5 um; mobile phase: Hex (0.1% DEA): EtOH=55:45; flow rate: 1 mL/min] to yield (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8a-d as an off-white solid.

LC/MS: mass calculated for $C_{24}H_{18}ClDF_2N_8O_2$: 525.14, measured (ES, m/z): 526.10 [M+H]$^+$. $^1$H NMR (400 MHz, DMSO-$d_6$) δ 12.25 (s, 1H), 9.84 (s, 1H), 8.34 (d, J=5.1 Hz, 1H), 7.94-8.00 (m, 1H), 7.86-7.90 (m, 1H), 7.71 (dd, J=8.6, 1.5 Hz, 1H), 7.57 (d, J=3.8 Hz, 1H), 5.70 (d, J=2.7 Hz, 1H), 5.23-5.29 (m, 1H), 5.04 (d, J=8.7 Hz, 1H), 4.63 (dd, J=6.0, 2.3 Hz, 2H), 2.65-2.77 (d, J=16.7 Hz, 1H), 2.52-2.58 (m, 1H), 2.16-2.29 (m, 1H), 2.06-2.14 (m, 1H), 2.90-2.02 (m, 2H). $^{19}$F NMR (376 MHz, DMSO-$d_6$) δ −112.85, −130.16.

Example 9: Compound of Formula (I-E)

(3S,8aS)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8a-d

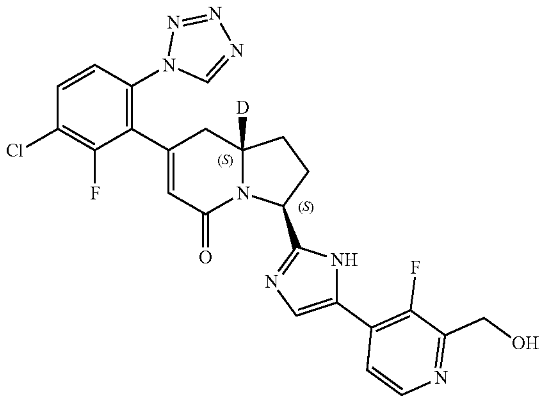

The title compound was prepared according to the procedure as described in Example 8 above, with a second fraction isolated and lyophilized to yield the title compound as a white solid.

LC/MS: mass calculated for $C_{24}H_{18}DClF_2N_8O_2$: 525.14, measured (ES, m/z): 526.10 $[M+H]^+$. $^1H$ NMR (400 MHz, DMSO-$d_6$) δ 12.52 (s, 1H), 9.84 (s, 1H), 8.34 (d, J=5.1 Hz, 1H), 7.94-8.01 (m, 1H), 7.85-7.92 (m, 1H), 7.71 (dd, J=8.7, 1.5 Hz, 1H), 7.62 (d, J=3.7 Hz, 1H), 5.70 (d, J=2.7 Hz, 1H), 5.00-5.08 (m, 1H), 4.64 (d, J=2.2 Hz, 2H), 2.42-2.46 (m, 1H), 2.31-2.41 (m, 1H), 2.20-2.30 (m, 1H), 1.95-2.08 (m, 1H), 1.64-1.78 (m, 1H), 1.14-1.28 (m, 1H). $^{19}F$ NMR (376 MHz, DMSO-$d_6$) δ −113.06, −129.81.

Example 10: Compound of Formula (I-F)

(3S,8aR*)-7-(3-Chloro-2-fluoro-6-(1H-tetrazol-1-yl)phenyl)-3-(5-(3-fluoro-2-(hydroxymethyl-d2)pyridin-4-yl)-1H-imidazol-2-yl)-2,3,8,8a-tetrahydroindolizin-5(1H)-one-8a-d

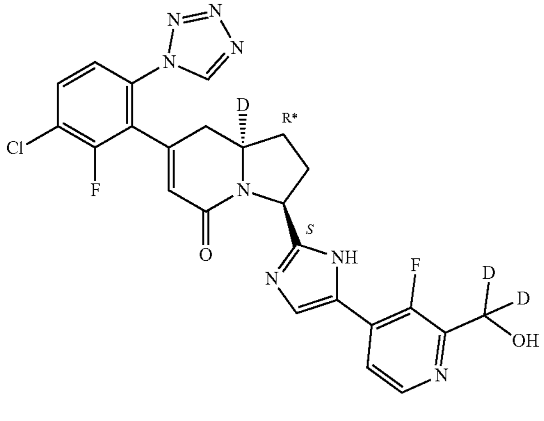

Step 1: 1-(tert-butyl) 2-methyl (2S)-5-methoxypyrrolidine-1,2-dicarboxylate-5-d

To a solution of 1-(tert-butyl) 2-methyl (2S)-5-hydroxypyrrolidine-1,2-dicarboxylate-5-d (14 g, 56.85 mmol, 1.0 equiv) in MeOH (140 mL) was added p-toluenesulfonic acid monohydrate (2.7 g, 14.21 mmol, 0.25 equiv). The mixture was stirred at room temperature overnight. The solvent was removed under vacuum and the residue was purified by silica gel column with EA/PE (0%-35%) to yield the 1-(tert-butyl) 2-methyl (2S)-5-methoxypyrrolidine-1,2-dicarboxylate-5-d as a yellow oil.

Step 2: 1-(tert-butyl) 2-methyl (2S)-5-((2,2-dimethyl-4-oxo-4H-1,3-dioxin-6-yl)methyl)pyrrolidine-1,2-dicarboxylate-5-d To a solution of 1-(tert-butyl) 2-methyl (2S)-5-methoxypyrrolidine-1,2-dicarboxylate-5-d (10 g, 38.4 mmol, 1.0 equiv) and ((2,2-dimethyl-4-methylene-4H-1,3-dioxin-6-yl)oxy)trimethylsilane (14.0 g, 65.32 mmol, 1.7 equiv) in tert-butylmethyl ether (100 mL) at −40° C. was added $BF_3{\cdot}Et_2O$ (6.8 g, 47.91 mmol, 1.25 equiv) over 10 min. The resulting mixture was stirred at −78° C. for 40 min. The reaction was allowed to warm to ambient temperature overnight. The reaction was quenched with saturated sodium bicarbonate solution (50 mL). The resulting mixture was extracted with ethyl acetate (3×100 mL). The organic layers were combined, dried over anhydrous sodium sulfate, filtered and concentrated. The residue was purified by silica gel chromatography (0-40% ethyl acetate/petroleum ether) to yield 1-(tert-butyl) 2-methyl (2S)-5-((2,2-dimethyl-4-oxo-4H-1,3-dioxin-6-yl)methyl)pyrrolidine-1,2-dicarboxylate-5-d as a yellow oil. LC/MS: mass calculated for $C_{18}H_{26}DNO_7$:370.19, measured: 393.20 $[M+H]^+$.

Step 3: methyl (2S)-5-((2,2-dimethyl-4-oxo-4H-1,3-dioxin-6-yl)methyl)pyrrolidine-2-carboxylate-5-d To a solution of 1-(tert-butyl) 2-methyl (2S)-5-((2,2-dimethyl-4-oxo-4H-1,3-dioxin-6-yl)methyl)pyrrolidine-1,2-dicarboxylate-5-d (8 g, 21.60 mmol, 1.0 equiv) in DCM (50 mL) was added TFA (10 mL). The mixture was stirred at room temperature for 1 h. The mixture was washed with $NaHCO_3$ solution (2×10 mL) and NaCl solution (1×10 mL). The organic layers were combined, dried over anhydrous sodium sulfate, filtered and concentrated to yield methyl (2S)-5-((2,2-dimethyl-4-oxo-4H-1,3-dioxin-6-yl)methyl)pyrrolidine-2-carboxylate-5-d as a yellow oil. LC/MS: mass calculated for $C_{13}H_{18}DNO_5$: 270.13, measured: 213.05 $[M+H-CO2Me]^+$.

Step 4: methyl (3S)-5-oxo-7-(((trifluoromethyl)sulfonyl)oxy)-1,2,3,5,8,8a-hexahydroindolizine-3-carboxylate-8a-d A mixture of methyl (2S)-5-((2,2-dimethyl-4-oxo-4H-1,3-dioxin-6-yl)methyl)pyrrolidine-2-carboxylate-5-d (6 g, 22.20 mmol, 1.0 equiv) in toluene (60 mL) was stirred at 100° C. for 1 h. The solvent was removed under vacuum and the residue was purified by silica gel column with MeOH/DCM (0%-20%) to yield methyl (3S)-5,7-dioxooctahydroindolizine-3-carboxylate-8a-d as a yellow oil.

To a solution of methyl (3S)-5,7-dioxooctahydroindolizine-3-carboxylate-8a-d (1 g, 4.71 mmol, 1.0 equiv) and triethylamine (1.4 g, 14.14 mmol, 3.0 equiv) in DCM (10 mL) was added 1,1,1-trifluoro-N-phenyl-N-((trifluoromethyl)sulfonyl)methanesulfonamide (1.7 g, 4.71 mmol) at 0° C. The mixture stirred at room temperature for 1 h. The reaction was quenched with water (20 mL). The resulting mixture was extracted with DCM (1×50 mL) and washed with water and NaCl solution (30 mL). The organic layers were combined, dried over anhydrous sodium sulfate, filtered and concentrated. The residue was purified by silica gel chromatography (0-20% ethyl acetate/petroleum ether) to yield the methyl (3S)-5-oxo-7-(((trifluoromethyl)sulfonyl)oxy)-1,2,3,5,8,8a-hexahydroindolizine-3-carboxylate-8a-d as a yellow oil. LC/MS: mass calculated for $C_{11}H_{11}DF_3NO_6S$: 344.04, measured: 345.00 $[M+H]^+$.

Step 5: methyl (3S)-7-(6-amino-3-chloro-2-fluorophenyl)-5-oxo-1,2,3,5,8,8a-hexahydroindolizine-3-carboxylate-8a-d To a solution of methyl (3S)-5-oxo-7-(((trifluoromethyl)sulfonyl)oxy)-1,2,3,5,8,8a-hexahydroindolizine-3-carboxylate-8a-d (1 g, 2.91 mmol, 1.0 equiv) in 1,4-dioxane (15 mL) and $H_2O$ (2 mL) was added (6-amino-3-chloro-2-fluorophenyl)boronic acid (1.1 g, 5.81 mmol, 1.0 equiv) followed by addition of $K_2CO_3$ (803 mg, 5.81 mmol, 2.0 equiv), $Pd(dppf)Cl_2$ (237 mg, 0.29 mmol, 0.1 equiv). The resulting mixture was maintained under nitrogen and stirred at 90° C. for 2 h. The reaction was quenched with saturated ammonium chloride solution (20 mL). The resulting mixture was extracted with ethyl acetate (3×20 mL). The organic layers were combined, dried over anhydrous sodium sulfate, filtered and concentrated. The residue was purified by silica gel chromatography (0-20% MEOH/DCM) to yield methyl (3S)-7-(6-amino-3-chloro-2-fluorophenyl)-5-oxo-1,2,3,5,8,8a-hexahydroindolizine-3-carboxylate-8a-d as a brown solid. LC/MS: mass calculated for $C_{16}H_{15}ClDFN_2O_3$: 339.09, measured: 340.05 $[M+H]^+$.

Step 6: (3S)-7-(6-amino-3-chloro-2-fluorophenyl)-5-oxo-1,2,3,5,8,8a-hexahydroindolizine-3-carboxylic-8a-d acid To a solution of methyl (3S)-7-(6-amino-3-chloro-2-fluorophenyl)-5-oxo-1,2,3,5,8,8a-hexahydroindolizine-3-carboxylate-8a-d (1.6 g, 4.71 mmol, 1.0 equiv) in tetrahydrofuran (20 mL) and water (4 mL) was added LiOH (169 mg, 7.06 mmol, 1.5 equiv). The reaction was stirred at room temperature for 1 h. The pH value was adjusted to 2~5 with 2 M HCl. The resulting mixture was extracted with ethyl acetate (2×50 mL). The organic layers were combined, dried over anhydrous sodium sulfate, filtered and concentrated to yield (3S)-7-(6-amino-3-chloro-2-fluorophenyl)-5-oxo-1,2,3,5,8,8a-hexahydroindolizine-3-carboxylic-8a-d acid as a brown solid. LC/MS: mass calculated for $C_{15}H_{13}ClDFN_2O_3$:325.07, measured: 326.20 $[M+H]^+$.

Step 7: (3S)-7-(3-chloro-2-fluoro-6-(1H-tetrazol-1-yl)phenyl)-5-oxo-1,2,3,5,8,8a-hexahydroindolizine-3-carboxylic-8a-d acid To a solution of (3S)-7-(6-amino-3-chloro-2-fluorophenyl)-5-oxo-1,2,3,5,8,8a-hexahydroindolizine-3-carboxylic-8a-d acid (1.6 g, 4.91 mmol, 1.0 equiv) in AcOH (6 mL) was added $TMSN_3$ (3 ml) and trimethoxymethane (3 mL). The mixture was stirred at room temperature overnight. The solvent was removed under vacuum and the residue was purified by C18 column with $CH_3CN$/water (5%-35%) to yield (3S)-7-(3-chloro-2-fluoro-6-(1H-tetrazol-1-yl)phenyl)-5-oxo-1,2,3,5,8,8a-hexahydroindolizine-3-carboxylic-8a-d acid as a yellow solid. LC/MS: mass calculated for $C_{16}H_{12}ClDFN_5O_3$: 378.08, measured: 379.05 $[M+H]^+$.

Step 8: 2-(2-(((tert-butyldimethylsilyl)oxy)methyl-d2)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate-8a-d To a solution of (3S)-7-(3-chloro-2-fluoro-6-(1H-tetrazol-1-yl)phenyl)-5-oxo-1,2,3,5,8,8a-hexahydroindolizine-3-carboxylic-8a-d acid (300 mg, 0.80 mmol, 1.0 equiv) in $CH_3CN$ (10 mL) was added $K_2CO_3$ (142 mg, 1.03 mmol, 1.3 equiv). After stirring at room temperature for 0.5 h, then 2-bromo-1-(2-(((tert-butyldimethylsilyl)oxy)methyl-d2)-3-fluoropyridin-4-yl)ethan-1-one (432 mg, 1.19 mmol, 1.5 equiv) was added. The mixture was stirred at room temperature for 1 h. The resulting mixture was purified by silica gel chromatography (0-7% MeOH/DCM) to yield 2-(2-(((tert-butyldimethylsilyl)oxy)methyl-d2)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate-8a-d as a yellow oil. LC/MS: mass calculated for $C_{30}H_{30}ClD_3F_2N_6O_5Si$: 661.21, measured: 662.15 $[M+H]^+$.

Step 9: (3S)-3-(5-(2-(((tert-butyldimethylsilyl)oxy)methyl-d2)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one-8a-d To a solution of 2-(2-(((tert-butyldimethylsilyl)oxy)methyl-d2)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate-8a-d (280 mg, 0.42 mmol, 1.0 equiv) in toluene (10 mL) and acetic acid glacial (1 mL) was added ammonium acetate (489 mg, 6.34 mmol, 15.0 equiv). The mixture was stirred at 100° C. for 1 h. The solvent was removed under vacuum and the residue was purified by silica gel column with MeOH/DCM (0%-10%) to yield (3S)-3-(5-(2-(((tert-butyldimethylsilyl)oxy)methyl-d2)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one-8a-d as a yellow oil. LC/MS: mass calculated for $C_{30}H_{30}ClD_3F_2N_8O_2Si$: 641.23, measured: 642.20 $[M+H]^+$.

Step 10: (3S,8aR*)-7-(3-chloro-2-fluoro-6-(1H-tetrazol-1-yl)phenyl)-3-(5-(3-fluoro-2-(hydroxymethyl-d2)pyridin-4-yl)-1H-imidazol-2-yl)-2,3,8,8a-tetrahydroindolizin-5(1H)-one-8a-d To a solution of (3S)-3-(5-(2-(((tert-butyldimethylsilyl)oxy)methyl-d2)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one-8a-d (140 mg, 0.22 mmol, 1.0 equiv) in THF (4 mL) was added triethylamine trihydrofluoride (1 mL). The mixture was stirred at 70° C. for 1 h. The solvent was removed under vacuum and the residue was purified by C18 column [condition: ACN-water-6.5 mM $NH_4HCO_3$+$NH_3H_2O$ (5%-50%)] to yield a residue. The residue was purified by chiral HPLC [column: (R,R)-Whelk-O1, 4.6*50 mm, 3.5 um; mobile phase A: Hex (0.1% DEA): EtOH=50:50, mobile phase B: flow rate: 1 mL/min] to yield (3S,8aR*)-7-(3-chloro-2-fluoro-6-(1H-tetrazol-1-yl)phenyl)-3-(5-(3-fluoro-2-(hydroxymethyl-d2)pyridin-4-yl)-1H-imidazol-2-yl)-2,3,8,8a-tetrahydroindolizin-5(1H)-one-8a-d as an off-white solid.

LC/MS: mass calculated for $C_{24}H_{16}D_3ClF_2N_8O_2$: 527.15, measured (ES, m/z): 642.20 $[M+H]^+$. $^1H$ NMR (400 MHz, DMSO-$d_6$) (400 MHz, DMSO-$d_6$) δ 12.29 (s, 1H), 9.84 (s, 1H), 8.34 (d, J=5.1 Hz, 1H), 7.93-8.02 (m, 1H), 7.84-7.92 (m, 1H), 7.70-7.75 (m, 1H), 7.58 (d, J=4.0 Hz, 1H), 5.69 (d, J=2.7 Hz, 1H), 5.12-5.32 (m, 1H), 5.04 (d, J=8.7 Hz, 1H), 2.63-2.80 (m, 1H), 2.50-2.56 (m, 1H), 2.17-2.31 (m, 1H), 2.05-2.15 (m, 1H), 1.90-2.01 (m, 2H). $^{19}F$-NMR: (376 MHz, DMSO-$d_6$) δ −112.86, −130.13.

Example 11: Compound of Formula (I-G)

(3S,8aR)-7-(3-Chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-1,1,8,8,8a-d5

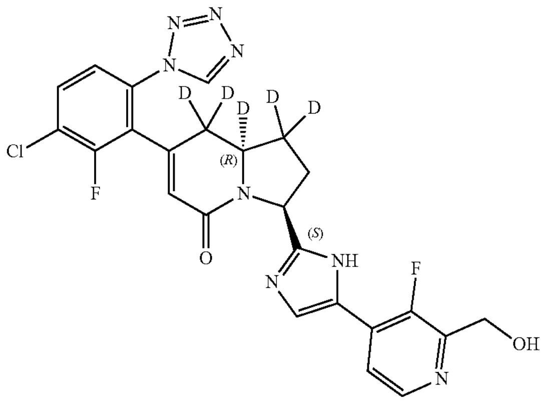

Step 1: 2-(2-(((Tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate-1,1,8,8,8a-d5

A mixture of (3S)-7-(6-amino-3-chloro-2-fluorophenyl)-5-oxo-1,2,3,5,8,8a-hexahydroindolizine-3-carboxylic-1,1,8,8,8a-d5 acid (120 mg, 0.36 mmol, 1.0 equiv.) and $Cs_2CO_3$ (71 mg, 0.22 mmol, 0.6 equiv.) in DMF (8 mL) was stirred at room temperature for 30 min. 2-Bromo-1-(2-(((tert-butyldimethylsilyl)oxy)methyl)-3-fluoropyridin-4-yl)ethan-1-one (185 mg, 0.51 mmol, 1.4 equiv.) was then added to the mixture. The reaction mixture was stirred at room temperature for 4 h. The resulting mixture was then diluted with EtOAc (120 mL), washed with water (3×20 mL), brine (2×20 mL), dried over $Na_2SO_4$, and concentrated. The residue was purified by flash column chromatography on silica gel (40 g, MeOH/DCM: 1/20) to yield of 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate-1,1,8,8,8a-d5 as a yellow solid. LC/MS: mass calculated for $C_{29}H_{29}ClD_5F_2N_3O_5Si$: 610.22, measured (ES, m/z): 611.15 $[M+H]^+$.

Step 2: (3S)-7-(6-Amino-3-chloro-2-fluorophenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one-1,1,8,8,8a-d5

Under an inert atmosphere of nitrogen, a mixture of 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate-1,1,8,8,8a-d5 (130 mg, 0.21 mmol, 1.0 equiv.) and $NH_4OAc$ (164 mg, 2.13 mmol, 10.0 equiv.) in AcOH (2 mL) and toluene (20 mL) was stirred at 110° C. for 30 min and then concentrated. The residue was purified by flash column chromatography on silica gel (40 g, MeOH/DCM: 1/15) to yield (3S)-7-(6-amino-3-chloro-2-fluorophenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one-1,1,8,8,8a-d5 as a yellow solid. LC/MS: mass calculated for $C_{29}H_{29}D_5ClF_2N_5O_2Si$: 590.25, measured (ES, m/z): 591.30 $[M+H]^+$.

Step 3: (3S,8aR)-7-(3-Chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-1,1,8,8,8a-d5

A mixture of (3S)-7-(6-amino-3-chloro-2-fluorophenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one-1,1,8,8,8a-d5 (80 mg, 0.14 mmol, 1.0 equiv.), $TMSN_3$ (156 mg, 1.35 mmol, 10.0 equiv.) and trimethoxymethane (143 mg, 1.35 mmol, 10.0 equiv.) in AcOH (8 mL) was stirred at 55° C. overnight. The solvent was removed under reduced pressure and the residue was applied onto a C18 reverse column (330 g, ACN/$H_2O$ (0.05% $NH_4HCO_3$): 5→50%) to yield (3S)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-1,1,8,8,8a-d5 as a white solid, which was further purified by prep-chiral-HPLC to yield (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-1,1,8,8,8a-d5 as a white solid.

LC/MS: mass calculated for $C_{24}H_{14}D_5ClF_2N_8O_2$: 529.16, measured (ES, m/z): 530.10 $[M+H]^+$. $^1H$ NMR (400 MHz, DMSO-$d_6$) (400 MHz, DMSO-$d_6$) δ 12.26 (s, 1H), 9.84 (s, 1H), 8.34 (d, J=5.0 Hz, 1H), 7.90-8.00 (m, 1H), 7.90 (t, J=5.4 Hz, 1H), 7.75-7.85 (m, 1H), 7.51-7.62 (m, 1H), 5.70 (s, 1H), 5.27 (t, J=6.0 Hz, 1H), 5.04 (d, J=8.7 Hz, 1H), 4.58-4.69 (m, 2H), 2.13-2.30 (m, 1H), 1.84-2.00 (m, 1H). $^{19}F$-NMR: (376 MHz, DMSO-$d_6$) δ −112.86, −130.15.

Example 12: Compound of Formula (I-H)

(3S,8aR)-7-(3-Chloro-2-fluoro-6-(1H-tetrazol-1-yl)phenyl)-3-(5-(3-fluoro-2-(hydroxymethyl-d2)pyridin-4-yl)-1H-imidazol-2-yl-4-d)-2,3,8,8a-tetrahydroindolizin-5(1H)-one

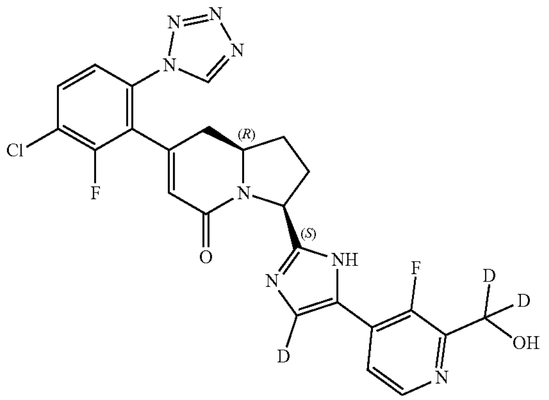

To a mixture of (3R,8aS)-7-(3-chloro-2-fluoro-6-(1H-tetrazol-1-yl)phenyl)-3-(5-(3-fluoro-2-(hydroxymethyl-d2)pyridin-4-yl)-4-iodo-1H-imidazol-2-yl)-2,3,8,8a-tetrahydroindolizin-5(1H)-one (25 mg, 0.038 mmol) and Zn dust (25 mg, 0.38 mmol) was added 1.5 g of $CD_3COOD$ (1.5 g) and the resulting mixture was stirred at room temperature for 4 h. The precipitate was then filtered off. The filtrate was concentrated under reduced pressure and the residue was purified by Gilson HPLC to yield 3S,8aR)-7-(3-chloro-2-fluoro-6-(1H-tetrazol-1-yl)phenyl)-3-(5-(3-fluoro-2-(hydroxymethyl-d2)pyridin-4-yl)-1H-imidazol-2-yl-4-d)-2,3,8,8a-tetrahydroindolizin-5(1H)-one as a light yellow solid.

LC/MS calculated for $C_{24}H_{19}ClF_2N_8O_2$: 527.1, measured 528.3 ($MH^+$); $^1H$ NMR (400 MHz, METHANOL-d4) δ 9.62 (s, 1H), 8.56 (s, 1H), 8.46 (s, 1H), 7.85 (dd, J=7.83, 8.80 Hz, 1H), 7.58 (dd, J=1.71, 8.56 Hz, 1H), 5.77-5.85 (m, 1H), 5.21-5.30 (m, 1H), 3.96-4.13 (m, 1H), 2.75-2.88 (m, 1H), 2.66-2.73 (m, 1H), 2.35-2.45 (m, 1H), 2.27-2.33 (m, 1H), 2.16-2.24 (m, 1H), 2.02-2.12 (m, 1H).

Example 13: Compound of Formula (I-J)

(3R,8aS)-7-(3-Chloro-2-fluoro-6-(1H-tetrazol-1-yl-d)phenyl)-3-(4-(3-fluoro-2-(hydroxymethyl-d2)pyridin-4-yl)-1H-imidazol-2-yl)-2,3,8,8a-tetrahydroindolizin-5(1H)-one

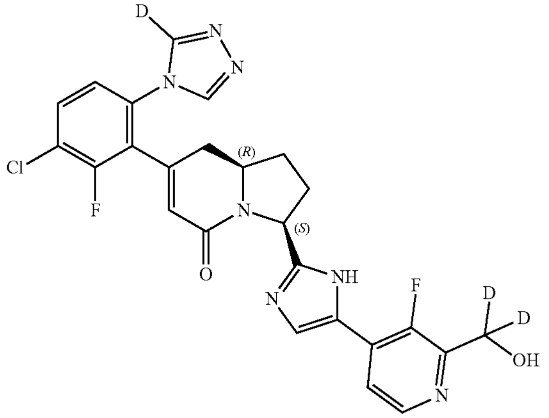

To a solution of (3S,8aR)-7-[3-chloro-2-fluoro-6-(tetrazol-1-yl)phenyl]-3-[4-[2-[dideuterio(hydroxy)methyl]-3-fluoro-4-pyridyl]-1H-imidazol-2-yl]-2,3,8,8a-tetrahydro-1H-indolizin-5-one (35 mg, 0.07 mmol) in $CD_3OD$ in a NMR tube was added $NaHCO_3$ and the sample was analyzed by $^1H$ NMR. Within a few mins, the acidic proton in the tetrazole ring exchanged with deuterium to yield (3R,8aS)-7-(3-chloro-2-fluoro-6-(1H-tetrazol-1-yl-d)phenyl)-3-(4-(3-fluoro-2-(hydroxymethyl-d2)pyridin-4-yl)-1H-imidazol-2-yl)-2,3,8,8a-tetrahydroindolizin-5(1H)-one.

LC/MS calculated for $C_{24}H_{16}D_3ClF_2N_8O_2$: 527.1, measured 528.3 ($MH^+$). $^1H$ NMR (400 MHz, METHANOL-d4) δ 8.02 (dd, J=8.31, 9.78 Hz, 1H), 7.78-7.88 (m, 1H), 7.54-7.61 (m, 1H), 7.14 (d, J=3.42 Hz, 1H), 6.49 (dd, J=1.96, 8.31 Hz, 1H), 5.73 (d, J=2.93 Hz, 1H), 5.16 (d, J=8.80 Hz, 1H), 3.84-3.96 (m, 1H), 2.89-3.04 (m, 1H), 2.56-2.65 (m, 1H), 2.28-2.39 (m, 1H), 2.16-2.26 (m, 2H), 1.99-2.12 (m, 1H).

Example 14: Compound of Formula (I-K)

(3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8,8,8a-d3

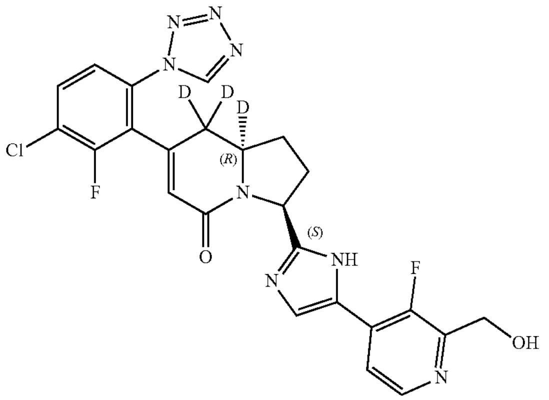

Step 1: (3S)-7-(6-amino-3-chloro-2-fluorophenyl)-3-(5-(3-fluoro-2-(hydroxymethyl)pyridin-4-yl)-1H-imidazol-2-yl)-2,3,8,8a-tetrahydroindolizin-5(1H)-one-8,8,8a-d3

To a solution of 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate-8,8,8a-d3 (0.51 g, 0.837 mmol, 1.0 equiv.) in toluene (10 mL) was added $NH_4OAc$ (0.65 g, 8.4 mmol, 10 equiv.) and AcOH (0.5 mL) and the resulting mixture was stirred for 1 h at 100° C. The mixture was then concentrated and purified by reverse phase chromatography on C18 (80 g, MeCN/$H_2O$ (0.05% $CF_3COOH$): 0>45%) to yield (3S)-7-(6-amino-3-chloro-2-fluorophenyl)-3-(5-(3-fluoro-2-(hydroxymethyl)pyridin-4-yl)-1H-imidazol-2-yl)-2,3,8,8a-tetrahydroindolizin-5(1H)-one-8,8,8a-d3 as a yellow solid (0.24 g, 60.4% yield). LC/MS: mass calculated. for $C_{23}H_{17}ClD_3F_2N_5O_2$: 474.15, measured: 476.20 $[M+H]^+$.

Step 2: (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8,8,8a-d3

A mixture of (3S)-7-(6-amino-3-chloro-2-fluorophenyl)-3-(5-(3-fluoro-2-(hydroxymethyl)pyridin-4-yl)-1H-imidazol-2-yl)-2,3,8,8a-tetrahydroindolizin-5(1H)-one-8,8,8a-d3 (0.22 g, 0.463 mmol, 1.0 equiv.), trimethoxymethane (2 mL), azidotrimethylsilane (2 mL) and acetic acid (2 mL) was stirred for 2 h at room temperature. The solvent was evaporated under vacuum to yield (3S)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8,8,8a-d3. The racemic product was separated by chiral-HPLC (Column: CHIRALPAK IF-3, 4.6*50 mm, 3 μm; Mobile Phase: MtBE (0.1% DEA): EtOH=70:30; Flow rate: 1 mL/min) to yield (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8,8,8a-d3 as a white solid.

LC/MS: mass calculated. for $C_{24}H_{16}ClD_3F_2N_8O_2$: 527.15, measured: 528.10 $[M+H]^+$. $^1H$ NMR (400 MHz, DMSO-$d_6$) δ 12.27 (s, 1H), 9.85 (s, 1H), 8.30-8.40 (m, 1H), 7.94-8.01 (m, 1H), 7.86-7.93 (m, 1H), 7.69-7.75 (m, 1H), 7.54-7.60 (m, 1H), 5.70 (s, 1H), 5.28 (t, J=6.0 Hz, 1H), 5.08-5.01 (m, 1H), 4.64 (dd, J=5.9, 2.3 Hz, 2H), 2.14-2.28 (m, 1H), 1.91-2.00 (m, 2H).

Example 15: Compound of Formula (II-A)

4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinic acid

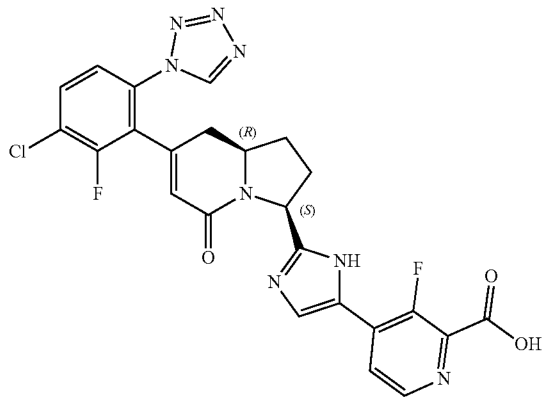

To a mixture of (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one (1.2 g, 2.286 mmol, 1.00 equiv) in DCM (60 mL) and $H_2O$ (30 mL) was added TEMPO (179 mg, 1.146 mmol, 0.50 equiv) and $PhI(OAc)_2$ (2.2 g, 6.830 mmol, 3.0 equiv). The reaction mixture was stirred at room temperature for 2 h. The resulting mixture was concentrated and the residue was applied onto a $C_{18}$ reverse phase column (330 g, ACN/$H_2O$ (0.05% $NH_4HCO_3$): 5%>>>23%>>>25%) to yield of 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinic acid as a white solid.

$^1H$ NMR (400 MHz, DMSO-$d_6$) δ 12.30 (br., 1H), 9.85 (s, 1H), 8.28 (d, J=8.0 Hz, 1H), 7.93-8.01 (m, 1H), 7.84-7.92 (m, 1H), 7.71 (d, J=8.7 Hz, 1H), 7.55 (d, J=4.0 Hz, 1H), 5.69 (d, J=2.7 Hz, 1H), 5.05 (d, J=8.8 Hz, 1H), 3.65-3.85 (m, 1H), 2.63-2.86 (m, 1H), 2.52-2.62 (m, 1H), 2.15-2.19 (m, 1H), 2.05-2.14 (m, 1H), 1.89-2.05 (m, 2H); $^{19}F$ NMR (376 MHz, DMSO-d6) δ −112.81, −127.49; LC/MS: mass calculated for $C_{24}H_{17}ClF_2N_8O_3$: 538.11, measured: 539.05 $[M+H]^+$;

Example 16: Compound of Formula (III-A)

4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoro-2-(hydroxymethyl)pyridine 1-oxide

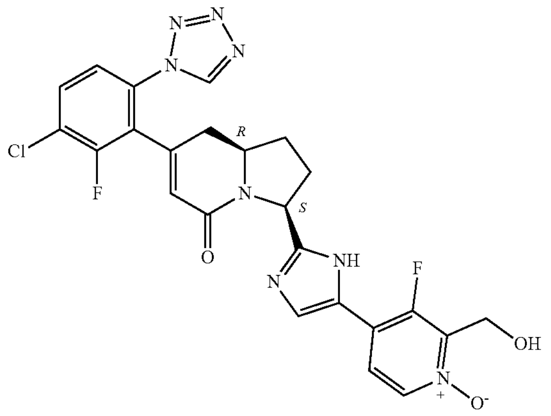

Step 1: 2-(((tert-butyldimethylsilyl)oxy)methyl)-4-(1-ethoxyvinyl)-3-fluoropyridine A mixture of 2-(((tert-butyldimethylsilyl)oxy)methyl)-3-fluoro-4-iodopyridine (0.80 g, 2.178 mmol, 1.00 equiv), tributyl(1-ethoxyvinyl)stannane (1.180 g, 3.267 mmol, 1.50 equiv) and $Pd(PPh_3)_4$ (0.252 g, 0.218 mmol, 0.10 equiv) in 1,4-dioxane (10 mL) was stirred at 100° C. for 4 h. The reaction was diluted with water and extracted with ethyl acetate twice. The combined organic layers were washed with brine, dried over sodium sulfate and concentrated to yield 2-(((tert-butyldimethylsilyl)oxy)methyl)-4-(1-ethoxyvinyl)-3-fluoropyridine as a light yellow solid. LC/MS: mass calculated for $C_{16}H_{26}FNO_2Si$: 311.2, measured: 312.2 $[M+H]^+$.

Step 2: 1-(3-fluoro-2-(hydroxymethyl)pyridin-4-yl)ethan-1-one

To a solution of 2-(((tert-butyldimethylsilyl)oxy)methyl)-4-(1-ethoxyvinyl)-3-fluoropyridine (2.5 g, 8.027 mmol, 1 equiv) in THF (15 mL) was added 2M HCl (20 mL). The mixture was stirred for 5 h at room temperature, then the pH value was adjusted to 8~10 with $NaHCO_3$ solution. The resulting mixture was extracted with EA three times. The combined organic layers were washed with brine, dried over $Na_2SO_4$ and concentrated under vacuum to yield 1-(3-fluoro-2-(hydroxymethyl)pyridin-4-yl)ethan-1-one as a light yellow solid.

Step 3: 4-acetyl-3-fluoro-2-(hydroxymethyl)pyridine 1-oxide

To a solution of 1-(3-fluoro-2-(hydroxymethyl)pyridin-4-yl)ethan-1-one (1.25 g, 7.390 mmol, 1 equiv) in DCM (20 mL) was added m-CPBA (2.550 g, 14.780 mmol, 2.0 equiv).

The reaction mixture was stirred for 2 h at room temperature, then quenched with $NaHCO_3$ solution. The resulting mixture was extracted with DCM three times. The combined organic layers were dried over $Na_2SO_4$ and concentrated under vacuum. The residue was applied onto a silica gel column with EA/PE (0-100%) to yield 4-acetyl-3-fluoro-2-(hydroxymethyl)pyridine 1-oxide as a white solid. LC/MS: mass calculated for $C_8H_8FNO_3$: 185.05, measured: 186.05 $[M+H]^+$ Step 4: 2-(acetoxymethyl)-4-(2-bromoacetyl)-3-fluoropyridine 1-oxide To a solution of 4-acetyl-3-fluoro-2-(hydroxymethyl) pyridine 1-oxide (0.9 g, 4.861 mmol, 1 equiv) in acetic acid (20 mL) was added a hydrogen bromide solution in acetic acid (2.384 g, 9.722 mmol, 2 equiv), followed by the addition of pyridinium tribromide (1.477 g, 4.618 mmol, 0.95 equiv) slowly. The reaction mixture was stirred for 2 h at room temperature, then concentrated under vacuum. The residue was admixed with water and EA. The organic phase was collected, dried over $Na_2SO_4$ and concentrated under vacuum to yield 2-(acetoxymethyl)-4-(2-bromoacetyl)-3-fluoropyridine 1-oxide as a light yellow oil. LC/MS: mass calculated for $C_{10}H_9BrFNO_4$: 304.97, measured: 306.00 $[M+H]^+$, 308.00 $[M+2+H]^+$.

Step 5: 2-(acetoxymethyl)-4-(2-(((3S)-7-(3-chloro-2-fluoro-6-(1H-tetrazol-1-yl)phenyl)-5-oxo-1,2,3,5,8,8a-hexahydroindolizine-3-carbonyl)oxy)acetyl)-3-fluoropyridine 1-oxide To a solution of (3S)-7-(3-chloro-2-fluoro-6-(1H-tetrazol-1-yl)phenyl)-5-oxo-1,2,3,5,8,8a-hexahydroindolizine-3-carboxylic acid (0.01 g, 0.026 mmol, 1.0 equiv) in MeCN (1 mL) was added potassium carbonate (0.007 g, 0.053 mmol, 2.0 equiv). After the mixture was stirred for 30 min, 2-(acetoxymethyl)-4-(2-bromoacetyl)-3-fluoropyridine 1-oxide (0.012 g, 0.040 mmol, 1.5 equiv) was added. The reaction mixture was stirred for 2 h at room temperature. LCMS showed that 2-(acetoxymethyl)-4-(2-(((3S)-7-(3-chloro-2-fluoro-6-(1H-tetrazol-1-yl)phenyl)-5-oxo-1,2,3,5,8,8a-hexahydroindolizine-3-carbonyl)oxy)acetyl)-3-fluoropyridine 1-oxide was generated and the reaction mixture was taken into the next step without further isolation or purification. LC/MS: mass calculated for $C_{26}H_{21}ClF_2N_6O_7$: 602.11, measured: 603.15 $[M+H]^+$.

Step 6: 2-(acetoxymethyl)-4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridine 1-oxide To a solution of 2-(acetoxymethyl)-4-(2-(((3S)-7-(3-chloro-2-fluoro-6-(1H-tetrazol-1-yl)phenyl)-5-oxo-1,2,3,5,8,8a-hexahydroindolizine-3-carbonyl)oxy)acetyl)-3-fluoropyridine 1-oxide (0.34 g, 0.564 mmol, 1.0 equiv) in toluene (15 mL) was added ammonium acetate (0.870 g, 11.290 mmol, 20 equiv) followed by the addition of acetic acid (0.5 mL) under $N_2$. The reaction mixture was stirred for 1 h at 100° C., then cooled to room temperature, and concentrated under vacuum. The residue was purified by silica gel chromatography with MeOH/DCM (0-15%) to yield 2-(acetoxymethyl)-4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridine 1-oxide as a light yellow oil. LC/MS: mass calculated for $C_{26}H_{21}ClF_2N_8O_4$: 582.13, measured: 583.10 $[M+H]^+$ Step 7: 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoro-2-(hydroxymethyl)pyridine 1-oxide To a solution of 2-(acetoxymethyl)-4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridine 1-oxide (0.16 g, 0.274 mmol, 1 equiv) in acetonitrile (10 mL) were added LiBr (0.119 g, 1.372 mmol, 5 equiv), triethylamine (0.278 g, 2.745 mmol, 10 equiv) and water (0.25 mL). The reaction mixture was stirred for 5 h at 60° C., then concentrated under vacuum. The residue was purified by (Column: YMC-Actus Triart C18 ExRS, 30 mm×150 mm, 5 μm; Mobile Phase A: Water (10 mmol $NH_4HCO_3$), Mobile Phase B: ACN; Flow rate: 60 mL/min; Gradient: 20 B to 30 B in 12 min) to yield 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoro-2-(hydroxymethyl)pyridine 1-oxide as a white solid.

LC/MS: mass calculated for $C_{30}H_{19}ClF_4N_6O_4$: 540.12, measured: 541.15 $[M+H]^+$. $^1$H NMR (400 MHz, Methanol-d4) δ 9.57 (s, 1H), 8.29 (d, J=6.9 Hz, 1H), 8.10 (t, J=7.9 Hz, 1H), 7.81 (dd, J=8.7, 7.6 Hz, 1H), 7.60 (d, J=4.1 Hz, 1H), 7.55 (dd, J=8.7, 1.6 Hz, 1H), 5.76 (d, J=2.7 Hz, 1H), 5.16 (d, J=8.6 Hz, 1H), 4.94 (d, J=3.2 Hz, 2H), 3.88-4.01 (m, 1H), 2.72-2.89 (m, 1H), 2.56-2.69 (m, 1H), 2.14-2.39 (m, 3H), 1.97-2.12 (m, 1H); $^{19}$F NMR (376 MHz, Methanol-$d_4$) δ −113.62, −124.02.

One skilled in the art will recognize that additional stereoisomers (e.g. enantiomers, diastereomers, etc.) of the compounds of formula (I), compounds of formula (II), the compounds of formula (III), compounds of formula (IV), compounds of formula (V), and compounds of formula (VI) may be prepared as described herein, by selecting and substituting suitably enantiomerically and/or diastereomerically enriched (e.g. ≥90% ee, preferably ≥98% ee) reagents or staring materials, and/or by preparation of the corresponding racemic compound, followed by chiral separation by for example, preparative chiral supercritical fluid chromatography (SFC) in which isocratic method conditions and stacked injections are used for optimal collection efficiency, by crystallization of the salt with chiral resolving reagents, kinetic resolution, or other known methods.

BIOLOGICAL EXAMPLES

Biological Example 1: Factor XIa Inhibition Assay

Using Fluorophore-quencher Pair Peptide Substrate

A fluorescence intensity-based assay was used to monitor inhibition of Factor XIa. The peptide substrate, 5Fam-KLTRAETV-K5Tamra (purchased from New England Peptide) was chosen based on the FXI sequence. Conversion of zymogen FIX to its activated form, FIXa, occurs by proteolytic cleavage by FXIa at two sites, Arg146 and Arg180. The custom peptide used in this assay was based on the Arg146 cleavage site. The peptide substrate was designed with a fluorophore-quencher pair, where the fluorescence is quenched until FXIa cleaves the 8-mer peptide after the Arg residue. The substrate $K_M$ was fit to a substrate inhibition model whereby $k_{cat}$=0.86 $s^{-1}$, $K_M$=12.4 μM, $K_i$=61.6 μM with an enzymatic efficiency, and $k_{cat}/K_M$=69523 $M^{-1}s^{-1}$.

Factor XIa FLINT assay was used with the following 5Fam-KLTRAETV-K5Tamra assay buffer: 50 mM Tris, pH 7.5, 100 mM NaCl, 5 mM $CaCl_2$, 0.1 mg/mL BSA, 0.03% CHAPS was used. Assay buffer was prepared by mixing all ingredients fresh. 2×5Fam-KLTRAETV-K5Tamra peptide substrate was first prepared in 100% DMSO, then diluted 10 mM to 3 mM in 100% DMSO. Assay buffer was then added directly to the 3 mM stock of substrate to prepare the 30 μM 2× working concentration (15 μM final concentration). The 2× Factor XIa stock solution was prepared by diluting 6.562 μM stock in 1× assay buffer for a 200 pM working stock solution (100 pM final concentration).

Test compound(s) were run in an 11-point, 3-fold serial dilution with a final top compound concentration of 100 nM. Final DMSO in assay was 2% DMSO. FXIa and compound were pre-incubated for 30 minutes and substrate was then added to initiate the reaction. The assay was linear using 100 pM FXIa greater than 30 minutes. More specifically, the assay was run as follows:

100 nL of 1 mM test compound was dispensed into a black 384-well non-binding Greiner BioOne 784900 plate for 10 μM final concentration with 1% DMSO final concentration;

5 μL of 1× assay buffer was dispensed to column 24 (low control) and 5 μL 2× Factor XIa solution was dispensed to columns 1-23 (column 23 high control);

the plate was centrifuged with a "cover" plate at 500 rpm for 1 min the plate was pre-incubated for 30 minutes at room temperature with plate covered;

5 μL of 2× 5Fam-KLTRAETV-K5Tamra peptide substrate was dispensed into the entire plate, columns 1-24;

the plate was centrifuged with a cover plate at 500 rpm for 1 min;

the plate was read kinetically monitoring fluorescence intensity on the BMG PHERAStar at room temperature, using fluorescence module F1 485 mm/520 mm.

Percent inhibition ($IC_{50}$) curves were generated per compound tested, and data was analyzed using a 4-parameter logistic fit using GeneData Screener. The relative fluorescence unit (RFU) values were normalized to percent inhibition using the following equation:

$$\%\ inhibition=((HC-LC)-(compound-LC)/(HC-LC))*100$$

where LC—low control=mean signal of no Factor XIa or 100% inhibition of Factor XIa; HC—high control=mean signal of Factor XIa+5Fam-KLTRAETV-K5Tamra peptide substrate with DMSO only.

An 11-point dose response curve for the test compound(s) was generated using GENDATA to determine $IC_{50}$ value based on the following equation:

$$Y=Bottom+(Top-Bottom)/(1+10^{\wedge}((\log IC_{50}-X)*HillSlope))$$

Where Y is the % inhibition in the presence of X inhibitor concentration, Top=high control=mean signal of Factor XIa+5Fam-KLTRAETV-K5Tamra peptide substrate with DMSO only; Bottom=low control—mean signal of no Factor XIa or 100% inhibition of Factor XIa; HillSlope—Hill coefficient; and IC50=concentration of compound with 50% inhibition in relation to top/high control.

Biological Example 2: Kallikrein Inhibition Assay

Utilizing Quenched AMC Peptide Substrate

A fluorescence intensity-based assay was used to monitor inhibition of human plasma kallikrein. The peptide substrate, Z-Gly-Pro-Arg-AMC (Purchased from Bachem; Catalog #1-1150) was chosen based on its relatively low $K_M$ for kallikrein which enables running the assay at lower substrate concentrations to control background fluorescence. The kinetic parameters for this substrate were determined by fitting titration data to the Michaelis-Menten equation yielding a $K_M$=40 μM, $k_{cat}$=0.76 $s^{-1}$, and $k_{cat}/K_M$=18932 $M^{-1}s^{-1}$.

Kallikrein FLINT assay was used with the following Z-Gly-Pro-Arg-AMC assay buffer: 50 mM Tris, pH 7.5, 100 mM NaCl, 5 mM $CaCl_2$, 0.1 mg/mL BSA, 0.03% CHAPS. Assay buffer was prepared by mixing all ingredients fresh. 2× Z-Gly-Pro-Arg-AMC peptide substrate was prepared by diluting 10 mM stock into 1× assay buffer for a 100 μM working concentration (50 μM final concentration). The 2× kallikrein stock solution was prepared by diluting 14.76 μM stock in 1× assay buffer for a 4 nM working stock solution (2 nM final concentration).

Test compound(s) were run in an 11-point, 3-fold serial dilution with a final top compound concentration of 1 μM. Final DMSO in assay: 2% DMSO. 2 nM kallikrein and test compound were pre-incubated for 30 minutes and 50 μM substrate was then added to initiate the reaction. The assay was linear using 2 nM kallikrein greater than 30 minutes. More specifically, the assay was run as follows:

100 nL of 1 mM test compound was dispensed into a black 384-well non-binding Greiner BioOne 784900 plate for 10 μM final concentration with 1% DMSO final concentration;

5 μL of 1× assay buffer was dispensed to columns 24 (low control) and 5 μL 2× human kallikrein enzyme solution was dispensed to columns 1-23 (column 23 high control);

the plate was centrifuged with a cover plate at 500 rpm for 1 min the plate was pre-incubated for 30 minutes at room temperature with plate covered;

5 μL of 2× Z-Gly-Pro-Arg-AMC peptide substrate was dispensed into the entire plate, columns 1-24;

the plate was centrifuged with a "cover" plate at 500 rpm for 1 min;

the plate was read kinetically monitoring fluorescence intensity on the BMG PHERAStar at room temperature, using fluorescence module F1 340 mm/440 mm.

Percent inhibition ($IC_{50}$) curves were generated per compound tested, and data was analyzed using a 4-parameter logistic fit using GeneData Screener. The relative fluorescence unit (RFU) values were normalized to percent inhibition using the following equation:

$$\%\ inhibition=((HC-LC)-(compound-LC)/(HC-LC))*100$$

where LC—low control=mean signal of human kallikrein enzyme or 100% inhibition of human kallikrein enzyme; HC—high control=mean signal of human kallikrein enzyme+Z-Gly-Pro-Arg-AMC peptide substrate with DMSO only.

An 11-point dose response curve for the test compound(s) was generated using GENDATA to determine $IC_{50}$ value based on the following equation:

$$Y=Bottom+(Top-Bottom)/(1+10^{\wedge}((\log/IC_{50}-X)*HillSlope))$$

Where Y is the % inhibition in the presence of X inhibitor concentration, Top=high control=mean signal of human kallikrein enzyme+Z-Gly-Pro-Arg-AMC peptide substrate with DMSO only; Bottom=low control—mean signal of no human kallikrein enzyme or 100% inhibition of human kallikrein enzyme; HillSlope—Hill coefficient; and $IC_{50}$=concentration of compound with 50% inhibition in relation to top/high control.

Representative compounds of the present invention were tested according to the procedure described in Biological Example 1 and Biological Example 2 above, with results as listed in Table B-1, below.

TABLE B-1

FXIa and Plasma Kallikrein Biological Activity

| Assay | Compound Formula | Results |
|---|---|---|
| Factor XIa $IC_{50}$ | (I-A) | 1.8 nM |
| Factor XIa $IC_{50}$ | (I-B) | 2.9 nM |
| Factor XIa $IC_{50}$ | (I-C) | 2.2 nM |
| Factor XIa $IC_{50}$ | (I-D) | 5.7 nM |
| Factor XIa $IC_{50}$ | (I-E) | 22.5 nM |
| Factor XIa $IC_{50}$ | (I-F) | 5.1 nM |
| Factor XIa $IC_{50}$ | (I-G) | 3.9 nM |
| Factor XIa $IC_{50}$ | (I-H) | 3.2 nM |
| Factor XIa $IC_{50}$ | (I-J) | 4.1 nM |
| Factor XIa $IC_{50}$ | (I-K) | 5.0 nM |
| Factor XIa $IC_{50}$ | (II-A) | 0.3 nM |
| Factor XIa $IC_{50}$ | (III-A) | 45.4 nM |
| Plasma kallikrein (PK) $IC_{50}$ | (I-A) | 13 nM |
| Plasma kallikrein (PK) $IC_{50}$ | (I-B) | 25 nM |
| Plasma kallikrein (PK) $IC_{50}$ | (I-C) | 17 nM |
| Plasma kallikrein (PK) $IC_{50}$ | (I-D) | 43 nM |
| Plasma kallikrein (PK) $IC_{50}$ | (I-E) | 72 nM |
| Plasma kallikrein (PK) $IC_{50}$ | (I-F) | 34 nM |
| Plasma kallikrein (PK) $IC_{50}$ | (I-G) | 33 nM |
| Plasma kallikrein (PK) $IC_{50}$ | (I-H) | 27 nM |
| Plasma kallikrein (PK) $IC_{50}$ | (I-J) | 32 nM |
| Plasma kallikrein (PK) $IC_{50}$ | (I-K) | 9.7 nM |
| Plasma kallikrein (PK) $IC_{50}$ | (II-A) | 11 nM |
| Plasma kallikrein (PK) $IC_{50}$ | (III-A) | 420 nM |

Biological Example 3

Reactive Metabolite Study in Human Liver Microsomes

The compound of formula (I-A) was assessed for bioactivation in HLM using GSH and KCN as trapping agents. The compound was incubated in human liver microsomes supplemented with NADPH, KCN and GSH at 37° C. for 60 min. The incubations were conducted with 1 mg/mL protein, 10 μM substrate, 1 mM GSH (non-labeled and labeled at 3:1) and KCN 1 mM (non-labeled and labeled at 3:1) in a total volume of 1 mL. Nefazodone (10 μM) was incubated under the same conditions as a positive control. After incubations, protein precipitation was performed for extraction of the metabolites by mixing with 5× volume of acetonitrile. The proteins were pelleted by centrifugation (3000 rpm, 10 minutes, 4° C.) and the supernatants were transferred into clean test tubes and evaporated to dryness under a gentle stream of nitrogen. The resulting residues were reconstituted in 300 μL of solvent mixture of water: acetonitrile (8:2 v/v) containing 0.1% formic acid prior to filtration using 0.45 μm nylon filter at 10,000×g at room temperature for 3 minutes. The filtrate was transferred to a 96-well plate for liquid chromatography/tandem mass spectrometric (LC-MS/MS) analysis.

LC-MS/MS analysis: Agilent 1260 Infinity UHPLC was coupled to a Bruker Q-TOF. The mass spectrometers were operated in a positive electrospray ionization mode. Column was Phenomenex, Luna C8 (150×2.0 mm ID, 3 μm). Mobile phases were A: 0.1% formic acid in water; mobile phase B: 0.1% formic acid in acetonitrile. A linear gradient with a flow rate of 0.2 mL/min was used throughout the analysis as follows:

| Time (min) | % Acetonitrile |
|---|---|
| 0 | 5 |
| 5 | 5 |
| 20 | 95 |
| 24 | 95 |
| 24.5 | 5 |
| 30 | 5 |

The compound of formula (I-A) was tested according to the reactive metabolite in HLM assay procedure described above and did not form GSH adducts or KCN adducts.

Biological Example 4

In Vitro Metabolism of in Human Cryopreserved Hepatocytes

The human hepatocytes used for in vitro metabolism of the compound of formula (I-A) were purchased from Bioreclamation IVT (Westbury, NY); cryopreserved male human hepatocytes (lot number: UYG).

Hepatocyte Incubation

Cryopreserved hepatocytes were rapidly thawed on ice, and vials were placed in a 37° C. water bath for approximately 90 sec, then immediately added to pre-warmed hepatocyte thawing media. The cells were resuspended within the media and then centrifuged at 700×g for 7 minutes at room temperature.

The supernatant was discarded, and the cells were resuspended in 2 mL of Krebs-Henseleit buffer containing 12.5 mM HEPES pH 7.4 (KHB). Cell viability and yield were determined by Trypan Blue exclusion. The hepatocytes were then diluted in KHB to a cell concentration of $2\times10^6$ cells/mL (500 μL/well in 10 mL glass tubes). The tubes were placed on a rotary shaker in a humidifier incubator supplied with 5% $CO_2$ and allowed 15 minutes acclimation at 37° C. prior to use. The compound of formula (I-A) or positive control, diclofenac (10 μM), in KHB was then added to the hepatocytes to achieve a final concentration of 10 μM and cell concentration of $1\times10^6$ cells/mL (1000 μL final incubation volume). Cells were incubated for zero or 3 hours. At the end of the incubation period, the cells were quenched with 6-volumes of ice-cold acetonitrile containing 0.02% formic acid, vortexed and sonicated (5 min). Precipitated proteins were pelleted by centrifugation (3000 rpm, 10 minutes, 4° C.) and the supernatant was transferred to borosilicate tubes and evaporated to dryness under a gentle stream of nitrogen.

Sample Preparation

The resulting residue after evaporation was reconstituted in 250 μL of water:acetonitrile (9:1 v/v) containing 0.01% formic acid with sonication and vortexing to aid solubilization of drug-derived materials prior to filtration using 0.45μ nylon filter at 10,000×g at room temperature for 10 minutes. The filtrate was transferred to a 96-well plate for liquid chromatography/ultraviolet/mass spectrometry (LC-UV/MS) analysis.

LC/UV/MS (Liquid Chromatography/Ultraviolet/Mass Spectrometry)

LTQ/Orbitrap (Thermo Scientific, Inc., Bremen, Germany) was carried out by data-dependent accurate mass measurements at resolving powers of 15,000 for full scan MS and 7,500 for $MS^2$ (also known as MS/MS or tandem mass spec) under single ion locked mass mode. Chromatographic separation of the unchanged drug and metabolites was achieved using a Kinetex Phenyl-hexyl column (150× 2.1 mm ID, 1.7 μm) from Phenomenex, Inc. (Torrance, CA, US) maintained at 35° C. and eluted with a nonlinear gradient consisting of water (solvent A) and acetonitrile (solvent B) containing 0.1% formic acid.

Quantification of the unchanged drug and its metabolites was carried out by integration of the individual chromatographically separated UV peaks and provided the percentage of total peak area.

Results:

The compound of formula (I-A) was tested according to the in vitro metabolite assay procedure as described above. The compound of formula (I-A) exhibited low turnover in human hepatocytes, with three oxidative and two glucuronide metabolites generated from the incubation. Diclofenac was used as positive control for the study and the turnover of diclofenac from human hepatocytes was 89%, indicating that the incubation system was valid. The (3-fluoropyridin-2-yl) methanol moiety was the major metabolic softspot of the compound of formula (I-A). The carboxylic acid metabolite, the compound of formula (II-A)

(II-A)

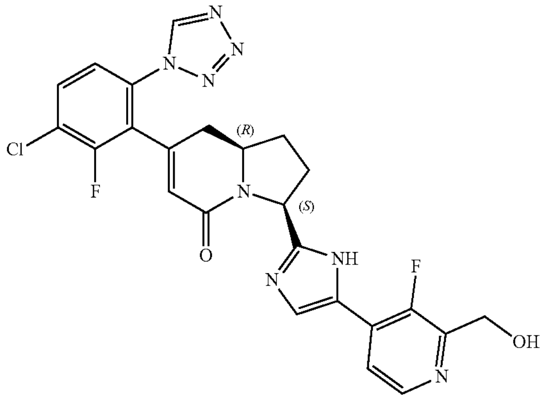

was a metabolite in human hepatocytes.

Biological Example 5: PK Studies

Animals: Male Sprague-Dawley rats (7-8 weeks old, body weight 250-300 g) were kept in plastic cages with free access to standard rat diet (Keaoxieli, Beijing, China) and water. The animals were maintained at a temperature of 20-25° C. with a 12-hour light/dark cycle and relative humidity of 40%-70% before the experiment.

Pharmacokinetics in rats: The cannulation of the jugular vein was pre-treated to the rats 2-3 days prior to the study. Test compound (dissolved in PEG400/water (1:1) or suspended in 0.5% HPMC) was administered orally via oral gavage at a dose of 5 or 10 mg/kg to 3 rats, and test compound (dissolved in 20% HPbCD or PEG400/water (1:1)) was injected to the tail vein at a dose of 1 or 2 mg/kg to 3 rats.

Blood samples (approximately 0.2 ml, each) were collected from the jugular vein at 0 (as a pre-dose), 5 (only for IV administration), 15, 30, 60, 120, 240, 360, 480 and 1440 mins post dose. A volume of 0.2 ml of heparinized 0.9% NaCl injectable solution (50 U/mL) was used to flush each cannula immediately after obtaining each blood sample, in order to prevent blood clotting and to compensate for fluid loss. Blood samples were separated by centrifugation, and approximately 0.1 ml aliquot of plasma was stored at −80° C. until analysis.

LC-MS/MS analysis: The analyte was assayed by a liquid chromatography coupled with tandem mass spectrometry (LC-MS/MS) method. The LC-MS/MS system consisted of a Shimadzu HPLC system (Kyoto, Japan) and API 5500 triple-quadrupole mass spectrometer equipped with a turbo electrospray ionization (ESI) source (AB Sciex, Toronto, Canada). LC conditions were as follows: column, Synergi 2.5μ Polar-RP 100A (50*3.0 mm) (Phenomenex, Torrance, CA); gradient elution at 0.5 mL/min with 5% acetonitrile in water containing 0.1% formic acid or 95% acetonitrile in water containing 0.1% formic acid; and injection volume, 10 μL. A multiple reaction monitoring (MRM) method was selected for quantitative analysis. The optimized transitions were Q1→Q3 and M1→M3 for analyte and internal standard, respectively. The instrumental parameters were set as follows: ion spray voltage: 5500 V; curtain gas: 30 psi; nebulizer gas: 50 psi; turbo gas: 50 psi; collision gas: 10 psi; temperature: 450° C.

Data analysis: Standard methods were used to calculate the pharmacokinetic parameters, such as the total area under the plasma concentration-time curve from time 0 to infinity ($AUC_{0-t}$) and terminal half-life, using non-compartmental analysis (WinNonlin), the peak plasma concentration ($C_{max}$) and time to reach $C_{max}$ ($T_{max}$) were determined directly from the experimental data.

Results: Rat PK for the compound of formula (I-A) was measured according to the assay procedure described above, with results as listed in Table B-2 below:

TABLE B-2

Rat PK for Compound of Formula (I-A)

| | |
|---|---|
| IV clearance | 19.6 ml/min/kg |
| $t_{1/2}$ (IV) | 3.25 h (formulation vehicle: 20% HPbCD at 2 mg/kg) |
| Oral $C_{max}$ | 3767 ng/ml |
| $t_{1/2}$ (PO) | 2.66 h |
| F | 53.4% (formulation vehicle: 0.5% HPMC at 10 mg/kg) |

Biological Example 6: hERG Assay

HERG (human ether-à-go-go-related gene) encodes a potassium channel with biophysical properties similar to the rapidly activating delayed-rectifier $K^+$ current ($I_{Kr}$) in cardiac myocytes. This $I_{Kr}$ current contributes to the $K^+$ current responsible for the repolarization phase of the cardiac action potential. Blockage of this current may prolong action potential duration and cause long QT-syndrome. The development of QT prolongation can lead to the occurrence of ventricular arrhythmias such as Torsades de Pointes, which can result in sudden death.

Experimental procedures: The effect of test compounds on the HERG current was studied at single-cell level using the single electrode, whole-cell voltage clamp technique.

Cells: A human embryonic kidney cell line (HEK293) with a stable transfection of HERG was used. The cells were continuously kept in culture. Before use the cells were seeded to small Petri dishes coated with poly-L-lysine. Experiments were performed on the cells 1-2 days after plating.

Solutions: The bath solution contained (in mM) 150 NaCl, 4 KCl, 5 glucose, 10 HEPES, 1.8 $CaCl_2$ and 1 $MgCl_2$ (pH 7.4 with NaOH). The pipette solution contained (in mM) 120 KCl, 5 EGTA, 10 HEPES, 4 MgATP, 0.5 $CaCl_2$ and 2 $MgCl_2$ (pH 7.2 with KOH). Test compounds were dissolved in DMSO to yield a stock solution of $10^{-2}$ M or $10^{-1}$ M. Control (=bath solution+DMSO) and test solutions (=bath solution+DMSO+test compound) contained 0.3% or 0.03% DMSO. Solutions were applied to the cell under study using a Y-tube system, allowing to rapidly change solutions (less than 0.5 s) in the vicinity of the cell.

Electrophysiological measurements: The membrane current of the cells was measured at distinct membrane potentials with the patch clamp technique by means of an EPC-9 patch clamp amplifier. The holding potential was −80 mV. The HERG current (K+-selective outward current) was determined as the maximal tail current at −40 mV after a 2 second depolarization to +60 mV. Pulse cycling rate was 15 s. Before each test pulse a short pulse (0.5 s) from the holding potential to −60 mV was given to determine (linear) leak current. After establishing whole-cell configuration a 5-minute equilibration period allowed for internal perfusion of the cell with the pipette solution. Thereafter test pulses were given for 5 minutes to quantify the HERG current in control conditions. While continuing the pulse protocol, perfusion was switched from control solution to test compound-containing solution. The effect of the test compound was measured after 5 minutes of drug application. One to three concentrations of the test compound were tested per cell.

Measurements: The HERG current was determined as the maximal tail current at −40 mV after a 2 second depolarization to +60 mV, starting from a holding potential of −80 mV.

The amplitude of the HERG current gradually decreased with time, even in control conditions. In order to accurately quantify the extent of block by test compounds, continuous rundown of the HERG current has to be taken into account. Therefore, the time course of the HERG current was fitted exponentially to the initial period of 5 minutes in control solution and extrapolated for the remainder of the experiment. These extrapolations provide the estimated amplitude of the current if no test compound would have been given. To determine the extent of block by the test compounds, the ratio between the measured current and the fitted current in control solution, extrapolated to the same point of time was calculated.

Standard conditions: The test compounds were dissolved in DMSO (final DMSO concentration: 0.3 or 0.03%). The effect of the test compound on the HERG current was measured after 5 minutes of drug application.

All-or-none criteria: If more than 5% reduction of the HERG current can be observed, the R-compound is considered to (partially) block the HERG current.

Results: The compound of formula (I-A) was tested in the hERG assay according to the procedure as described above and was measured to exhibit an $IC_{50}$ of >30 μM.

Biological Example 7: AMES II Assay

The aim of this study was to evaluate compound(s) and/or their metabolite(s) for their ability to induce reverse mutations in a gene of histidine-requiring *Salmonella typhimurium* strains to produce histidine-independent strains of these bacteria, in the absence and in the presence of a mammalian metabolic activation system. The Ames reverse mutation test has been shown to be a rapid and sensitive indicator for mutagenic activity of a broad range of chemical classes.

Mutagenic potential was assessed by using an in-house adaptation of the Ames II Mutagenicity Assay kit from Xenometrics (Boulder, CA, USA). The strains TA98 and TA mixed (a combination of 6 strains) used in this study were able to detect frame-shift mutations and base pair substitutions respectively.

Experimental procedures: The test compound was dissolved in DMSO and was handled at all times in a manner to reduce the risk of any accidental exposure to the staff and the environment.

In the in vitro gene reverse mutation test, effects were determined by exposing a mutant strain of *Salmonella typhimurium* to various concentrations of the test compound. Normally *Salmonella typhimurium* is capable of synthesizing the histidine which it requires for growth, but the mutant strain used in this test is incapable of this function. When large numbers of these bacteria are exposed to a mutagen, reverse mutation to the original histidine independent form takes place in a proportion of the bacterial population. These colonies (revertants) are readily detectable due to their ability to grow on a histidine deficient medium. Since many compounds do not exert their mutagenic effect until they have been metabolized by enzyme systems not available in the bacterial cell, the test compound and the bacteria are incubated in the presence of a supplemented liver fraction taken from animals previously treated with a compound known to induce a higher level of enzyme activity. The bacterial reverse mutation test uses amino acid requiring strains of *Salmonella typhimurium* to detect point mutations, which involve substitution, addition or deletion of one or a few DNA base pairs. The principle of this bacterial reverse mutation test is that it detects mutations, which revert mutations present in the test strains and restore the functional capability of the bacteria to synthesize an essential amino acid. The revertant bacteria are detected by their ability to grow in the absence of the amino acid required by the parent test strain. The bacterial reverse mutation test has been shown to be a sensitive, rapid and accurate indicator of the mutagenic activity of a wide range of chemical classes. The *S. typhimurium* strains TA98 and TA mixed were used in this study. They are histidine dependent (his−) and revert to histidine prototrophy (his+) by mutations. These strains have additional mutations that increase their sensitivity to mutagens. In bacteria, almost all of the primary damage caused to DNA by a mutagen is repaired by excision and repair systems so that only a small percentage of the potential mutagenic damage is expressed. The uvrB mutation is a deletion in the uvrB gene which results in a deficient DNA excision repair system making the strains more sensitive to mutagens. The uvrB deletion extends through the bio gene so that the bacteria also require biotin for growth. The rfa mutation (deep rough) affects the cell-membrane so that the normal lipopolysaccharide (LPS) cell-wall is defective. The rfa mutation increases the permeability of the cell-wall to large molecules such as those containing large ring systems that would otherwise be excluded by a normal cell wall. The strains containing the plasmid, pKM101, are reverted by a number of mutagens that are detected weakly or not at all with the non plasmid bearing parent strains. This pKM101 plasmid increases chemical and spontaneous mutagenesis by enhancing an error-prone DNA repair system.

Genotypes of the *S. typhimurium* used in the assay were as listed in Table B-3 below.

TABLE B-3

| Genotypes of the *S. typhimurium* Strains | | | | | | |
|---|---|---|---|---|---|---|
| Strains | Mutation | Type | Target | Cell wall | Repair | pKM101 |
| TA98 | hisD3052 | frameshift | GC | rfa | uvrB | yes |
| | | "Mixed strains" | | | | |
| TA7001 | hisG1775 | b.p. subst. | A:T > G:C | rfa | uvrB | yes |
| TA7002 | hisC9138 | b.p. subst. | T:A > A:T | rfa | uvrB | yes |
| TA7003 | hisG9074 | b.p. subst. | A:T > G:C | rfa | uvrB | yes |
| TA7004 | hisG9133 | b.p. subst. | G:C > A:T | rfa | uvrB | yes |
| TA7005 | hisG9130 | b.p. subst. | G:C > A:T | rfa | uvrB | yes |
| TA7006 | hisC9070 | b.p. subst. | C:G > G:C | rfa | uvrB | yes |

The tester strains were prepared from fresh overnight Oxoid nutrient broth cultures using the frozen strains which are stored below −70° C. Bacterial cultures for the studies were obtained by inoculating the Oxoid nutrient broth with frozen culture and incubating overnight at 37° C.

The in vitro metabolic activation system was comprised of rat liver enzymes (S9-fraction) and an energy producing system (Core) containing Nicotinamide Adenine Dinucleotide Phosphate (NADP) and Glucose-6-Phosphate (G-6-P). In short, the enzymes were contained in a 9000×g supernatant from liver homogenate prepared from adult male Wistar rats treated with 500 mg/kg of Aroclor 1254 five days prior to sacrifice. The treatment with Aroclor 1254 was used to induce mixed function oxidase enzymes capable of metabolizing chemicals to more active forms. The S9 fraction was retained frozen at about −70° C. until used. The S9 fraction was thawed immediately before use and combined with the Core to form the activation system (S9-mix) described in Table B-4, below.

TABLE B-4

| AMES Activation System (S9-mix) | |
|---|---|
| Component | Final Concentration |
| NADP | 4 mM |
| G-6-P | 5 mM |
| Mg | 8 mM |
| KCl | 33 mM |
| phosphate buffer, pH 7.4 | 0.1 M |
| S9 | 30% |

Standard conditions: The test compound concentrations and S9-mix were prepared just before use. All concentration levels of the test compound, negative controls and positive controls were plated in triplicate in a 24 well plate in the presence of bacteria. After a 90 min incubation (37° C.) step (orbital shaker, 250 rpm), 2.75 ml Indicator Medium was added to each well, whereafter 50 μl volumes were transferred to a 384 well plate according to a fixed pattern. The 384 well plates were incubated in the dark at 37° C. for 48 h. After incubation the plates were analyzed by scoring the number of positive wells (yellow color or bacterial colony visible at the bottom of the well). Information of possible precipitation of the compound in the wells was also recorded. Individual plate counts were entered directly into the computer which allowed proper presentation of each plate count against those of the control or the compound, by bacterial strain and metabolic activation system.

All-or-none criteria: The number of yellow colored wells on the solvent control plates was taken as the background level of mutation for the test. Reversion values are considered positive if: (a) the test compound produced at least a threefold increase in the mean number of revertants with one of the strains (TA98 or Mixed) at one or more concentration levels, as compared to the concurrent solvent control. Due to the nature of the strains, low spontaneous mutation rates can sometimes lead to an extremely low number of revertant wells in the solvent control. At this moment, the historical background level must be taken into consideration; and (b) a dose-effect relationship is observed.

These criteria were applied in most cases. If equivocal results were obtained, more tests were required to evaluate the mutagenic potential of the test compound. If the test compound produced a positive response in a single test that could not be reproduced in additional runs, the initial positive test data was discounted.

Control experiments: Before a test was considered valid, the positive controls were tested and showed at least a threefold increase in the number of revertant wells above the solvent control value for the mixed strains and TA98.

PIR-observations: were noted as follows:

- PIR1=no increase in revertant colonies
- PIR2=equivocal increase (no clear dose response or reproducibility)
- PIR3=clear dose related and reproducible increase in revertant colonies.

Reference compounds: The positive control articles were 2-aminoanthracene for the experiment with metabolic activation and 2-nitrofluorene and 4-nitroquinoline-N-oxide for the experiment without metabolic activation, as listed in Table B-5 below.

TABLE B-5

| AMES Reference Compounds | | | | | |
|---|---|---|---|---|---|
| Compound | CAS No. | Solvent | Final conc. | S9 | Strains |
| 2-aminoanthracene | 613-13-8 | DMSO | 5.0 μg/ml | + | All strains |
| 2-nitrofluorene | 607-57-8 | DMSO | 1.0 μg/ml | − | TA98 |
| 4-nitroquinoline-N-oxide | 56-57-5 | DMSO | 1.0 μg/ml | − | TAmixed |

The control articles were handled at all times in a manner to reduce the risk of any accidental exposure to the staff and the environment. Solutions of the positive control articles were prepared immediately prior to use and a final 2% DMSO solvent solution will be present in each culture. The stability of the positive control articles in solution was unknown, but an increase in the number of revertant colonies in the expected range demonstrates biological stability.

Results: The compound of formula (I-A) was tested according to the procedure described above and was determined to be negative in the AMES II assay.

Biological Example 8: In Vitro Micronucleus Assay

The in vitro micronucleus test (MNT) is a genotoxicity test for the detection of micronuclei (MN) in the cytoplasm of interphase cells. Micronuclei may originate from acentric chromosome fragments (i.e., lacking a centromere) or whole chromosomes that are unable to migrate to the poles during the anaphase stage of cell division. Compounds and/or their metabolites are evaluated for their ability to induce chromosome/genome aberrations in a TK6 human lymphoblastoid cell line, in the absence and in the presence of a mammalian metabolic activation system. Human TK6 cells are often used in the in vitro micronucleus test and it is noteworthy that these cells have a wild-type p53 status, a feature that some groups speculate may help to reduce the frequency of false positive results. The assessment is done by means of manual and/or semi-automated microscopical analysis. The in vitro MNT has been shown to be a sensitive test for the assessment of the genotoxic potential of chemical and physical agents in primary cells and cell lines. MN have the same morphology as an interphase nucleus with the exception that they are smaller than the main nuclei in the cell, hence the term "micronucleus".

The in vitro micronucleus test using TK6 cells is an accepted regulatory genotoxicity assay. Studies involving the micronucleus assay in TK6 are designed to meet the requirements of the current international guidelines issued by the OECD 487 test guideline and ICH S2 (R1).

Reference Compounds: Concurrent positive control agents were used to assure responsiveness of the test system and to demonstrate the potential of the metabolizing system to convert pro-mutagens into active metabolites, but not to provide a standard for comparison with the test item. The positive control chemicals used in this test for each treatment condition (treatment time and metabolic activation) were as shown in Table B-5, below. The solvent used for each positive control chemical and the final test concentrations in each condition were as listed in Table B-6, below.

TABLE B-6

Positive controls

| Positive control chemical | CAS no. | Genotoxic action | Solvent Test concentration | Metabolic activation (±S9) |
|---|---|---|---|---|
| Cyclophosphamide (3 h) | 6055-19-2 | Clastogen (+S9 only) | DMSO 2.5 μg/mL | + |
| Cyclophosphamide (3 h) | 6055-19-2 | Clastogen (+S9 only) | DMSO 4 μg/mL | + |
| Mitomycin C (continuous) | 50-07-7 | Clastogen | DMSO 30 ng/ml | − |
| Mitomycin C (continuous) | 50-07-7 | Clastogen | DMSO 40 ng/ml | − |

A concurrent negative (vehicle) control containing dimethyl sulfoxide (DMSO; CAS no. 67-68-5) was included (the final DMSO concentration is 1%).

Assay principle: Cell cultures were exposed to the test compound both with and without an exogenous source of metabolic activation. Concurrent negative, solvent/vehicle and positive controls were included in all tests. During or after exposure to the test compound, the cells were grown for a period sufficient to allow chromosome or spindle damage to lead to the formation of micronuclei in interphase cells. Harvested and stained interphase cells were analyzed for the presence of micronuclei. It was important to demonstrate that the cells analyzed were likely to have undergone cell division during or after exposure to the test compound. For all protocols, it was important to demonstrate that cell proliferation occurred in both the control and treated cultures, and the extent of test compound-induced cytotoxicity and/or cytostasis was assessed in the cultures scored for micronuclei. The total duration allowed the cells to complete at least one division and, hence, expression of induced lesions as micronuclei (i.e. 1-5-2.0 cell doublings should have occurred).

The in vitro micronucleus test was performed using two treatment schedules: treatment for three hours in the presence of a rat liver S9-based metabolic activation system (S9 mix) and continuous treatment, approximately 24 hours, in the absence of S9 mix. As needed, a second test was conducted to confirm the findings of the first.

Devices used in the Assay: Freezer (approx. −10° C. to −30° C.); Freezer (approx. −80° C.); Refrigerator (approx. 2° C. to 8° C.); Centrifuge (capable of centrifuging 96 well plates); $CO_2$-regulated, 37° C. incubator; Z1 Coulter Counter; Shandon Cytospin 4 Thermo; Vortex mixer; Ultrasonic bath (Grant Water Bath OLS 200); Microscope (Axio Imager 2—Zeiss); and Microscope (GXML3201—GX Microscopes)

Test specific materials used in the Assay: Cell line TK6 (ATTC CRL-8015); R10P culture medium; Medium containing RPMI 1640+Glutamax™—I (Gibco™ 61870044)+ horse inactivated Serum (Gibco 16050-122)+Penicillin/Streptomycin (Gibco 15140-122)+Sodium Pyruvate (Gibco 11360-039)+Pluronic Acid (Gibco 24040-032); Centrifuge tubes (15 ml/50 ml)—5 mL round bottom tubes (Corning/falcon 352054); Micropipettors/multichannels—Cell culture flasks T75 (Falcon, BD—Cat no. 353136); 96 well plates U-bottom, sterile, polystyrene (Star Lab E2996-1700); Breath Easy Sealing Membranes (Sigma Aldrich/Merck 2380059); 96 well flat bottom plates, sterile with lid—96 well plates V-bottom, sterile, polystyrene (Thermo Fisher 249662); DMSO (Fisher BP231-100)

Methods and Procedures: The test compound was solubilized in DMSO (dimethylsulfoxide). Vortex mixing, sonication and warming up to 37±2° C. were employed as needed to aid solubilization. Test compound was stored protected from light at room temperature. After formulation in DMSO and use in initial experiment, remaining formulated test compound was stored at room temperature in a vented storage cabinet protected from light alongside desiccant.

The test compound formulation was prepared immediately before dosing according to the relevant Gentronix Standard Operating Procedures. Briefly, a stock solution of the test compound in the solvent was prepared and then diluted in the same solvent to formulate the required concentration(s). Doses for any subsequent tests were based on the findings in the initial test.

The TK6 cell line was purchased from the European Collection of Authenticated Cell Cultures. This was then used to create an in-house master stock of TK6 cells and from this, working stocks were created. All stocks were stored in liquid nitrogen. Cells were maintained in log phase and passaged every 1-4 days in RPMI 1640 containing 10% heat inactivated horse serum (Gibco, Life Technologies, UK), antibiotics and Pluronic F68.

TK6 culture wells were treated with 2.2 μl of the test compound solution or positive control solution; negative control cultures were treated with the same volume of solvent. Cells in 218 μl were added to wells. The final total volume was 220 μl.

Assay Procedure:

DAY 1: TK6 cells were seeded into a T75 culture flask at a density of approximately 200,000 cells/ml (5% CO2 at 37° C.).

DAY 2: On the day of treatment, cultures were prepared at a density of 200,000 cells/ml in a flat bottom 96 well plate. Cells were treated with at least 24 concentrations of the test compound in 3 replicates (final concentration of DMSO is 1%). Concurrent negative, vehicle and positive controls were included. At least 2 possible treatment designs were performed. Cells were treated for 3 hours in the presence of a rat metabolic activation system, after which the cultures were centrifuged (in a U-bottom 96 well plate), washed with medium and then resuspended with fresh medium for a post-treatment recovery period (in a U-bottom 96 well plate). Cells were counted with a Z1 Coulter Counter. Continuous treatment (23-28 hours) occurs in the absence of metabolic activation.

The mammalian liver post-mitochondrial fraction (S9 homogenate) used for metabolic activation was prepared from male Sprague Dawley rats induced with Aroclor 1254 and purchased from Molecular Toxicology Inc. (MOLTOX, USA). Batches of S9 were stored frozen (−80° C.) and thawed just prior to use. Each batch was certified by the manufacturer for sterility, protein content, cytochrome P450 catalyzed enzyme activities and the ability to convert known promutagens to bacterial mutagens. S9 fractions require exogenous cofactors for activation. The cofactors that were used consisted of a NADPH regenerating system which was purchased from Apollo. Cofactor reagents were prepared in R10P culture media as follows: (a) Glucose-6-phosphate (mol. wt. 260.14) at 7.0 g/L for a finished solution of 25 mM; and (b) NADP (mol. wt. 743.41) at 3.8 g/L for a finished solution of 5 mM.

Equal quantities of the two solutions were mixed and adjusted to pH 7.2 with 1 M aqueous sodium hydroxide. The solutions were filter sterilized and approximately 5.5 mL aliquots were dispensed into suitable containers. All solutions were stored at approximately −80° C. and used within six months.

S9 homogenate was adjusted to a protein content of 30 mg/mL before addition to culture medium. The final concentration of liver homogenate (S9) in the test system was 2.0%:

DAY 3: Cytotoxicity profile: After treatment, the number of viable cells was determined by a cell count of one of the replicate cultures wells using a Z1 Coulter Counter to calculate the number of Population Doublings (PDs) and the Relative Population Doubling (RPD):

$$PD=[\log(Ni/N0)]/\log 2$$

where N0: baseline count at time zero; Ni: cell concentration at a given time point (i, end of incubation). For the treated cultures, the PDs were expressed as a percentage of the number of PDs in the concurrent vehicle controls.

RPD=[# of PDs in treated cultures/# of PDs in control cultures]×100

Based on the obtained cytotoxicity profile, test compound concentrations were selected (per treatment arm) for MN analysis. The aim was to select at least one concentration that covered 55±5% cytotoxicity. If no cytotoxicity or precipitate was observed, the highest test concentration was selected as corresponding to 1 mM or 500 μg/ml, whichever was lower (ICH S2 (R1), 2011). When solubility was the limiting factor, the maximum concentration, was the lowest concentration at which minimal precipitate was visible in cultures, provided there was no interference with scoring. Evaluation of precipitation was done by light microscopy at the end of treatment.

Microscopic analysis: After treatment, cells were centrifuged (cytospin) onto glass slides, fixed in methanol and stained with acridine orange (manual analysis) or DAPI (semi-automated analysis). For all selected test conditions (test compound(s) and positive controls), cytoslides were made from separate cultures: 2 cultures for microscopic analysis.

Microscopic analysis (of blind coded cytoslides) was performed to determine the number of micronucleated cells (MNC). The presence of micronuclei was evaluated in at least 2000 mononuclear cells per test condition (at least 1000 cells per culture; 2 cultures per concentration). As a measure for genotoxicity, the number of MNC was used to calculate the percentage of MNC:

% MNC=[#MNC/#mononuclear cells analyzed]×100

In addition, the fold increase in MNC in the treated cultures compared to the concurrent vehicle control was calculated:

Fold increase in MNC=% MNC in treated culture/% MNC in VC culture

For semi-automated analysis, the acquired images (Metafer 4.0.8 and Neon 1.1.6) were also assessed manually in order to allow the exclusion of false positives. To confirm obtained results, ad hoc concentrations were verified by manual microscopic analysis. Manual microscopic analysis allowed the quantification of additional cellular effects, such as the induction of binucleated (BN), polynucleated (POLY) and apoptotic (APO) cells; endpoints which are typically not quantified by semi-automated analysis.

Microscopy scoring criteria: A suitable area of the slide was selected by the analyst (i.e. not too thinly or densely spread). ells should not be overlapping and cytoplasm must be clearly visible around the nuclei. Suspected MN were confirmed or rejected according to the following criteria: (a) the MN diameter was less than one-third of the diameter of the main nucleus and be located within the intact cytoplasm of the cell; (b) the MN evenly stained, the same color and in the same focal plane as the main nucleus; (c) the MN were non-refractile and spherical, with a well-defined outline; and (d) the MN were not linked or connected to the main nucleus. Care was taken not to score binuclear cells with irregular shapes or where the two nuclei differed greatly in size; neither were binuclear cells confused with poorly spread multinuclear cells. Multinuclear cells were analyzed for micronuclei.

Test acceptance criteria: A treatment condition was considered acceptable for the evaluation of genotoxic effects if: (a) at least 1.5 cell population doublings occurred in the vehicle control cultures; (b) the frequency of MNC in the vehicle control cultures approximated those of the acceptable ranges from Gentronix's historical control database and/or published values; (c) the positive control compound (s) induced a biologically significant increase (statistically significant and outside the historical vehicle control range) in the frequency of MNC above the concurrent vehicle control value; (d) the maximum concentration reached (i) the cytotoxicity limit around 55±5% (RPD=45±5%), (ii) solubility limit or (iii) 500 μg/ml or 1 mM, whichever is lower. Note that the test acceptance criteria are not absolute and other extenuating factors may enter into the final acceptability decision. Experiments were repeated independently, as needed, to satisfy the acceptance criteria.

Test evaluation criteria: If the test acceptance criteria were met, the following criteria were used for the evaluation of the results based on the OECD 487 test guideline (2016):

Clearly Positive (score 3): (a) At least one test concentration induced a statistically significant (Fisher exact test, p value<0.05) increase compared with the concurrent vehicle control. (b) The increase in MNC was dose-related in at least one experimental condition when evaluated with a trend test (Cochran Armitage test, p value<0.05). (c) Any statistically significant increases in MNC were outside the distribution of the laboratory historical vehicle control data (Poisson based 95% confidence limits). A test compound which met all of the above criteria in at least one experimental condition (treatment arm) was considered able to induce biologically relevant chromosome breaks and/or chromosome gain or loss in this system.

Clearly Negative (score 1): (a) None of the test concentrations induced a statistically significant increase compared with the concurrent vehicle control (Fisher exact test). (b) There was no concentration related increase in MNC evaluated with a trend test (p value<0.05). (c) All results were within the distribution of the historical vehicle control data (95% control limits). A test compound which met all of the above criteria was considered unable to induce chromosome breaks and/or gains or loss in this test system.

Equivocal (score 2): A test compound which meets only some of the above criteria for a clearly positive or clearly negative response was evaluated by expert judgment and/or further investigations (e.g. analyzing more cells from existing experiments or repeat testing with an adjusted concentration range).

In rare cases, when even after further investigations, the data set could not allow a conclusion of positive or negative, then the result was concluded as equivocal.

Inconclusive (score 0): Test acceptance criteria were not met and further testing was required prior to final compound classification.

Note that there was no requirement for the verification of clearly positive or clearly negative results. The preceding criteria were not absolute and other extenuating factors may enter into the final evaluation decision. A trend test was only considered valid for those experiments where a statistically significant MN induction was observed.

Results: The compound of formula (I-A) was tested according to the in vitro MNT assay procedure described above and was negative (score of 1).

Biological Example 9

Assessment of TDI Potential Using the $IC_{50}$ Shift Method

To establish the potential for TDI of a particular P450 isozyme, the test compound is preincubated over a concentration range (typically 0.04 to 10 μM) with HLMs in the presence of cofactor NADPH for 30 minutes. After pre-incubation, a probe substrate known to be specifically metabolized to a defined metabolite by the isoform under investigation is then added at fixed concentration. Following a pre-defined incubation period (e.g. 10 minutes for the CYP3A4 testosterone assay), the reaction is terminated by addition of a suitable organic solvent (typically, acetonitrile) containing an internal standard. The samples are centrifuged prior to analysis by LC-MS/MS analysis and IC50 TDI value is calculated using curve fitting. This is compared to the IC50 for reversible inhibition, obtained when the pre-incubation step is performed in the absence of test compound (IC50 Rev). A leftwards shift in the IC50 (i.e. increased inhibition) upon pre-incubation indicates the potential for TDI of that isozyme. The IC50 shift value is calculated as the ratio of IC50 Rev/IC50 TDI.

The assay was performed on a fully automated Tecan robotic system. Sample analysis was performed via LC-MS/MSMS using stable-labelled internal standard of the probe substrate metabolite.

Final incubation conditions were as listed in Table B-7, below:

TABLE B-7

| Incubation Conditions, TDI Potential Assay | |
|---|---|
| CYP | 3A4 |
| Probe Substrate | Testosterone |
| Activity | 6β-hydroxylation |
| Probe Substrate Conc (μM) | 25 |
| Protein conc (mg/ml) | 0.15 |
| Inc Time (mins) | 10 |
| Reversible Reference inhibitor (negative control for TDI) | Ketoconazole (incubation range 0.0005-0.375 μM) |
| Positive control for TDI: | Troleandomycin (incubation range 0.0412-30 μM) |

Results: CYP3A4 (testosterone): The compound of formula (I-A) was tested according to the TDI potential assay as described above, under standard solvent conditions. Without pre-incubation, the measured $IC_{50}$ was 12.2±1.4 μM (68.2% maximum concentration). With pre-incubation, the measured $IC_{50}$ was 17.5±2.5 μM (62.8% maximum concentration). The $IC_{50}$ shift is 0.70.

Biological Example 10

Human Liver Microsomes CYP450 Cocktail Inhibition Assay

The cocktail DDI assay was used to evaluate test compound(s) for potential to cause drug-drug interactions via inhibition of clinically important P450 isoforms (CYP1A2, 2C8, 2C9, 2C19, 2D6, and 3A4) in early discovery. Discrimination of the inhibitory potential of the test compound towards each isoform was achieved by using a cocktail of specific probe substrates which are known to be selectively metabolized to defined metabolites by the isoforms under investigation. For example, dextromethorphan is known to be demethylated exclusively by the 2D6 isoform. Co-incubation of the probe substrates in human liver microsomes (HLM) with the test compound(s) at a range of inhibitor concentrations allows calculation of $IC_{50}$ values for multiple CYP isoforms simultaneously and therefore offers a higher throughput compared to a traditional single probe assay.

Methods and Procedures: Final protein concentration in the incubation was 0.2 mg/ml and incubation time was 10 mins. The final total solvent in the incubation was 0.15% DMSO and 0.8% acetonitrile. The assay was automated on a Beckman Biomek FX automated liquid handler with multi-channel pipetting tools (8-channel and 96-channel), on deck reagent cooling capabilities and integrated automated Cytomat incubator (37° C.) with plate shaking facilities (Kendro).

Test compounds were supplied as 5 mM DMSO stock solutions. 0.1 M Phosphate buffer (pH7.4) was prepared in house using $Na_2HPO_4 \cdot 12H_2O$ and $KH_2PO_4$.

Frozen human liver microsomes (HLM) were thawed at 37° C. while agitating regularly until the whole volume was thawed, then held on ice. Based on the protein concentration of the HLM batch, the suspension was further diluted in assay buffer and the probe substrate mixture (substrate for each CYP isoform) to yield the final protein concentration of 0.2 mg/mL.

Probe substrates were prepared separately in assay buffer (phenacetin, tolbutamide, S-mephenytoin, dextromethorphan) or water (amodiaquine, midazolam). These were combined (at the appropriate conc per substrate) with HLM and assay buffer to yield the final Enzyme/Substrate mix.

The final total solvent in the incubation was 0.15% DMSO and 0.8% acetonitrile. NADPH (5.27 mM) was prepared as a solution in assay buffer (Room Temp). The quenching solution containing deuterated analogues of each of the seven probe substrate metabolites was dissolved at an appropriate concentration in acetonitrile.

Assay procedure: Samples for incubation were prepared by combining appropriate volumes of Enzyme/Substrate mix (80 µl) and stock solutions of test or reference inhibitors (1 µl solutions added from a dilution series). Following a pre-incubation period (typically, 10 minutes), the reaction was initiated by the addition of NADPH solution (19 µl, 5.27 mM). The samples were incubated at 37° C. for 10 mins. The incubations were quenched by the addition of 1.6 volumes of chilled quenching solution. The incubations were then centrifuged for 10 minutes at 4000 rpm at 4° C. A defined volume of the supernatant (S/N) was transferred into a separate container and diluted with water (S/N: Water=60 µL/180 µL). Each sample was injected onto a UPLC/MS system using an LC/MS method selective for the simultaneous measurement of all seven probe substrate metabolites (and associated deuterated internal standards).

Calculations and Formulas: Percentage activity was calculated as $$\% \text{ activity}=(Ri/R)*100$$

where Ri and R were the metabolite to internal standard peak area ratios in the presence and absence of TC, respectively. The percentage activity data were then plotted against log (TC concentration) and a curve was fitted to the data to return the $IC_{50}$ using a data reduction tool within 3DX. Specifically, the algorithm used within the tool was based on the sigmoidal four parameter relationship: response (% activity) as a function of the concentration, where the four parameters are $IC_{50}$, Hill slope, baseline and range and the relationship between them is:

$$\text{Response}=\text{Range}/(1+(\text{concentration}/\text{IC50})^\wedge\text{Hill})+\text{Baseline}.$$

The line of best fit using the above relationship, was achieved using the non-linear fitting algorithm of Marquardt-Levenberg. A curve generated from seven single-point concentrations was used to calculate $IC_{50}$.

Results: The compound of formula (I-A) was tested according to the TDI potential assay procedure described above, with measured $IC_{50}$ values against human liver microsomes as listed in Table B-8, below.

TABLE B-8

| Human Liver Microsomes Inhibition | |
|---|---|
| HLM | Calculated $IC_{50}$ |
| 1A2 | $IC_{50}$ > 20 µM |
| 2C19 | $IC_{50}$ > 20 µM |
| 2C8 | $IC_{50}$ > 20 µM |
| 2C9 | $IC_{50}$ > 20 µM |
| 2D6 | $IC_{50}$ > 20 µM |
| 3A4 | $IC_{50}$: 14.4 µM |

Biological Example 11: Seahorse Assay

The purpose of this assay was to investigate the effect of the compound of formula (I-A) on mitochondrial respiration in HepG2 cells using the Agilent Seahorse XFe96 analyzer. Cell viability was also determined in HepG2 cells in parallel to the Seahorse assay.

Measurement of mitochondrial respiration in HepG2 Cells: Compound doses were prepared in 100% DMSO and subsequently diluted in assay medium to achieve final solvent concentration of 0.10%. HepG2 cells were plated overnight in a Seahorse plate (Agilent Technologies, Santa Clara, California) at a density of 40,000 cells/well in EMEM containing 10% HI FBS and 1× Pen/Strep cell culture. The cultures were washed twice with assay medium containing Seahorse XF base medium (Agilent, Part no. 103334-100), 16 mM glutamine, 5.5 mM glucose, and 8 mM pyruvate. Following the washes, 175 µl of assay medium was added and the plate was put in a 37° C. (without $CO_2$) incubator to begin the assay. Mitochondrial respiration, quantitated as oxygen consumption rate (OCR), was measured on an Agilent Seahorse XFe96 analyzer using the Seahorse Mito Stress test assay as per the manufacturer's protocol. Briefly, to assess compound-specific effects on mitochondrial function, each test compound (at concentrations of 0.3, 1, 3, 10, 30, and 100 µM) or vehicle control (0.1% DMSO) was added, followed by the sequential addition of three mitochondrial modulators, each shifting a unique metabolic parameter of the cell. First, 2 µM oligomycin, a complex V (ATP synthase) inhibitor, followed by 1 µM FCCP (Carbonyl cyanide-p-trifluoromethoxyphenylhydrazone), an uncoupling reagent, and finally a 0.5 µM combination of rotenone/antimycin A, complex I and III inhibitors, respectively.

Cell viability measurements: HepG2 cells were seeded onto black-walled 96 well plates at a density of 40,000 cells/well in EMEM containing 10% HI FBS and 1× Pen/Strep and allowed to attach overnight. The next day, test compounds were prepared and diluted in EMEM. Following a one-hour incubation with the test article(s), cell viability was assessed using the Cell Titer Fluor Assay (Promega, Cat no. G6081) according to the manufacturer's protocol. The viability assay monitors activity of cathepsin, a ubiquitous protease found in live cells.

Data Analyses: Mitochondrial SRC (spare respiratory capacity) was calculated by subtracting the rate of the basal respiration from the rate of the maximal respiration. SRC values were automatically generated by the Report Generator (Agilent Technologies-version 4.0). All experiments were run in triplicate and the mean and standard deviations were calculated for each test concentration. All data were normalized to vehicle controls.

$IC_{50}$ values were determined by nonlinear regression and fitting of the dose response curves to a two-parameter equation with variable slope (Hill coefficient):

$$Y = \left[\frac{100}{1 + 10^{[logTC50-X]*Hill\ coefficient}}\right]$$

where Y is the normalized response between 0% and 100% and X is the log (inhibitor concentration). All analyses were performed using GraphPad Prism 7.0 (San Diego, California).

Results: The compound of formula (I-A) was tested according to the Seahorse assay procedures described above and exhibited no direct effect on mitochondrial respiration with $IC_{50}$>100 µM, as measured by spare respiratory capacity. There was also no effect on cellular viability, with $IC_{50}$>100 µM.

Biological Example 12

Rabbit AV Shunt (Thrombosis) Assay and Ex Vivo Clotting Time

Male New Zealand White (NZW) rabbits were purchased from Charles River Lab (CRL) at a body weight range between 2.45-3.22 kg, and at about 10-14 weeks of age. Animals were housed in standard rabbit cages using one animal per cage and maintained at 22° C., 12 h daylight cycle in the animal room. Standard rabbit diet and water were provided, along with enrichment with fruits and carrots. No green leaves were provided to avoid interference with anticoagulant studies.

The rabbit AV shunt model was established as described in the literature (Wong, P. C., et al., Nonpeptide factor Xa inhibitors III: effects of DPC423, an orally-active pyrazole antithrombotic agent, on arterial thrombosis in rabbits, J Pharmacol Exp Ther, 2002; pp 993-1000, Vol 303(3)). Rabbits were randomly divided into different experiments groups, and the group sizes (n=2-5) varied depending on the availability of test compound.

Ketamine HCl (20.0-50.0 mg/kg, IM) and xylazine (2.0-10.0 mg/kg, IM) were used for anesthetic induction. Subsequent anesthetic maintenance was provided as needed (i.e., approximately every 30-50 minutes) with ketamine HCl (@22.7-25.0 mg/kg/~0.5 hr, IM) and xylazine (@2.27-5.0 mg/kg/~ 0.5 hr, IM) for the duration of the study. Alternatively, rabbits were induced and subsequently maintained on Isoflurane gas anesthetic (2-4% isoflurane and $O_2$ flow rate at 0.9-1.2 L/min via nose cone).

Following anesthesia, a 2-cm incision was made on each thigh to expose the femoral artery and vein, respectively, from the opposing thighs. The vein and artery were cannulated with a PE-100 tubing. Following the vascular cannulation, the rabbit was allowed to equilibrate for 20 minutes. An AV shunt device was then connected between the femoral arterial (at one thigh) and femoral vein (at the opposite thigh) cannulas. The shunt device consisted of an outer piece of TYGON tubing (length, 8 cm; i.d., 7.9 mm) and an inner piece of tubing (length, 2.5 cm; i.d., 4.8 mm). The shunt also contained an 8-cm length of 2-0 silk thread as the trigger for thrombus formation. Forty (40) min after blood flow through the shunt was initiated, the shunt was disconnected and the silk thread, along with the clot, was removed and weighed.

The following test compound and vehicle were used for the rabbit AV shunt studies:

Compound of formula (I-A) with vehicle of 35% HydroxyPropyl β- -Cyclodextrin (HPBCD) in 10 mM phosphate buffer, pH7;

Vehicle of 70/20/10 PEG/water/ethanol.

Dosing solutions were prepared fresh daily in vehicle at various doses. Vehicle or test compound was administered using i.v. dosing, via the marginal ear vein, 20 minutes prior to beginning the AV shunt thrombosis study (initial or loading dose) and subsequently continuous infusion for 40 mins (maintenance dose).

Statistical analysis: All the data are expressed as mean±SEM. Statistical analyses were performed using GraphPad Prism software (v8.0). Significance was defined at $p<0.05$ as determined by one-way ANOVA. Tukey's test was used for multiple comparisons.

Results:

Compared to vehicle, thrombus weight reduction for the compound of formula (I-A) was as listed in Table B-9, below.

TABLE B-9

| Thrombin Weight | | | |
|---|---|---|---|
| Initial Dose (mg/kg) | Maintenance Dose (mg/kg) | Thrombin Reduction (weight %) | p Value |
| 0.15 | 0.13 | 26.7% | |
| 0.5 | 0.43 | 52.3% | <0.001 |
| 1.5 | 1.3 | 51.3% | <0.001 |
| 5.0 | 4.3 | 71.2% | <0.0001 |
| 15.0 | 13 | 82.6% | <0.0001 |

Ex Vivo Clotting Assay:

The following coagulation reagents were purchased from Diagnostica Stago (Parsippany, NJ): Thrombin 10 (Catalog No: 00611, lot No: 251851) for thrombin time (TT), Neoplastine® Cl 5 (Catalog No: 00666, lot No: 01504) for prothrombin time (PT), C.K. Prest® 5 (Catalog No: 00597, lot No: 112768) and $CaCl_2$ (0.025 M, Catalog No: 00367, Lot No: 254158) for activated partial thromboplastin time (aPTT). Coagulometer STA rt4 (Diagnotica Stago) was used for ex vivo clotting time analysis.

Blood samples (1 mL each) were collected in 3.2% sodium citrate (BD Biosciences, Franklin Lakes, NJ) before and after shunt set up from the femoral artery cannula and centrifuged at 2500 g for 15 minutes at 20° C. The resulting platelet poor plasma (PPP) was transferred into clean tubes and stored at −80° C. until use.

Coagulation assays were performed with PPP in a 4 channel coagulometer STA rt4 (Diagnotica Stago). For the aPTT assay, 50 µl C.K. Preset reagent was incubated with 50 µl PPP for 3 min at 37° C. in a cuvette, and coagulation was initiated by adding 50 µl 25 mM $CaCl_2$). The onset of clotting was recorded as the coagulation time.

Statistical analysis: All the data are expressed as mean±SEM. Statistical analyses were performed using GraphPad Prism software (v8.0). Significance was defined at $p<0.05$ as determined by one-way ANOVA. Tukey's test was used for multiple comparisons.

Results:

Compared to vehicle, measured onset of clotting for the compound of formula (I-A) was as listed in Tables B-10 and B-11, below.

TABLE B-10

| Individual Rabbit ex vivo aPTT Onset of Clotting Time | | | | | | |
|---|---|---|---|---|---|---|
| Initial + Maintenance | Rabbit ID | | | | | |
| Dose in mg/kg (test time point[a]) | 1 | 2 | 3 | 4 | 5 | 6 |
| | Onset of Clotting Time (min) | | | | | |
| 0.15 + 0.13 (20 min) | 31.8 | 29.3 | 24.5 | 26.4 | | |
| 0.15 + 0.13 (60 min) | 30.4 | 25.4 | 22.3 | 17.4 | | |
| 0.5 + 0.43 (20 min) | 24.2 | 24.4 | 25.1 | 27.9 | | |
| 0.5 + 0.43 (60 min) | 20.7 | 19.8 | 19.7 | 23.6 | | |
| 1.5 + 1.3 (20 min) | 37.2 | 27.9 | 31.4 | 33.5 | | |
| 1.5 + 1.3 (60 min) | 32.7 | 31.5 | 24.7 | 23.3 | | |
| 5.0 + 4.3 (20 min) | 54.9 | 39.5 | 50.4 | 44.8 | | |
| 5.0 + 4.3 (60 min) | 42.2 | 37.0 | 55.8 | 40.0 | | |
| 15.0 + 13.0 (20 min) | 59.4 | 60.3 | 96.9 | 61.8 | | |
| 15.0 + 13.0 (60 min) | 63.3 | 71.9 | 59.6 | 73.2 | | |
| Baseline | 19.6 | 17.1 | 19.7 | 21.7 | 26.2 | 18.5 |
| Vehicle | 21.6 | 20.7 | 18.9 | 22.0 | 25.5 | 23.6 |

[a]test time point is post initial dose

TABLE B-11 ex vivo aPTT Onset of Clotting Time

| Initial + Maintenance Dose in mg/kg (test time point[a]) | mean | SD | n | SEM | Fold vs baseline |
|---|---|---|---|---|---|
| 0.15 + 0.13 (20 min) | 28.00 | 3.21 | 4 | 1.61 | 1.37 |
| 0.15 + 0.13 (60 min) | 23.88 | 5.46 | 4 | 2.73 | 1.17 |
| 0.5 + 0.43 (20 min) | 25.40 | 1.71 | 4 | 0.86 | 1.24 |
| 0.5 + 0.43 (60 min) | 20.95 | 1.82 | 4 | 0.91 | 1.02 |
| 1.5 + 1.3 (20 min) | 32.50 | 3.89 | 4 | 1.95 | 1.59 |
| 1.5 + 1.3 (60 min) | 28.05 | 4.74 | 4 | 2.37 | 1.37 |
| 5.0 + 4.3 (20 min) | 47.40 | 6.69 | 4 | 3.35 | 2.32 |
| 5.0 + 4.3 (60 min) | 43.75 | 8.31 | 4 | 4.16 | 2.14 |
| 15.0 + 13.0 (20 min) | 69.6 | 18.23 | 4 | 9.11 | 3.40 |
| 15.0 + 13.0 (60 min) | 67.00 | 6.61 | 4 | 3.30 | 3.27 |
| Baseline | 20.47 | 3.19 | 6 | 1.30 | |
| Vehicle | 22.05 | 2.29 | 6 | 0.94 | 1.08 |

[a]test time point is post initial dose

Formulation Example 1

Solid, Oral Dosage Form—Prophetic Example

As a specific embodiment of an oral composition, 100 mg of the compound of formula (I-A), prepared as in Example 5 above, or the compound of formula (II-A), prepared in Examples 13 above, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Throughout this application, various publications are cited. The disclosure of these publications is hereby incorporated by reference into this application to describe more fully the state of the art to which this invention pertains.

What is claimed:

1. A compound of formula (I)

(I)

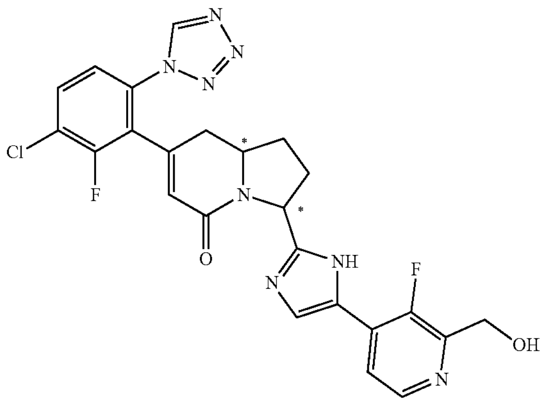

or a tautomer, stereoisomer, isotopologue, or pharmaceutically acceptable salt or solvate thereof.

2. The compound of claim 1 has formula (I-A)

(I-A)

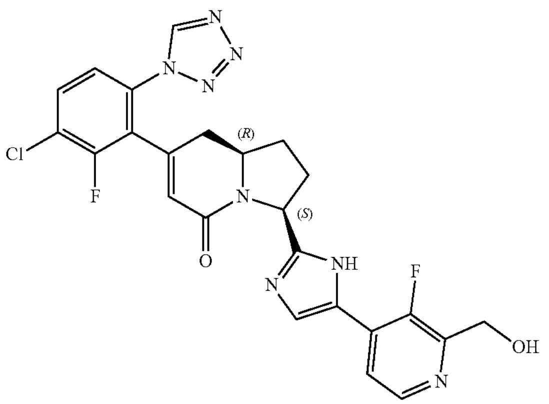

or a tautomer, stereoisomer, isotopologue, or pharmaceutically acceptable salt or solvate thereof.

3. The compound of claim 1, selected from (a) compound of formula (I-B)

(I-B)

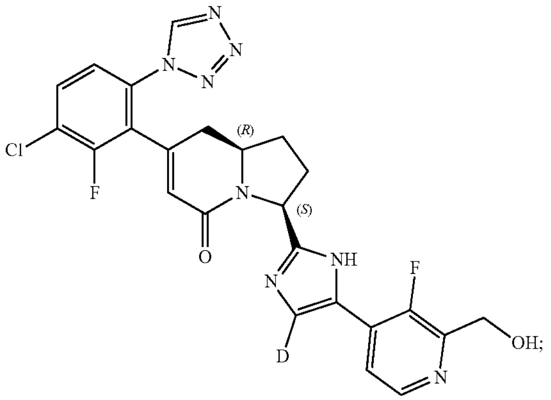

(b) compound of formula (I-C)

(I-C)

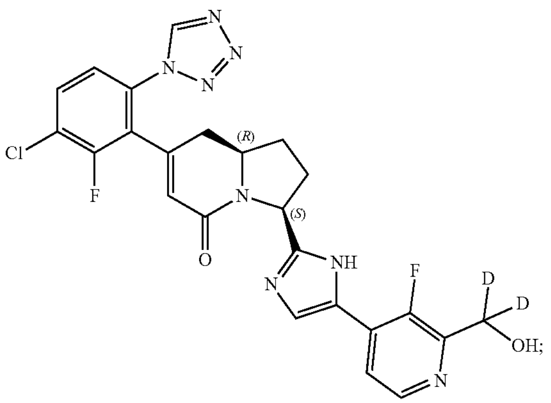

(c) compound of formula (I-D)
(I-D)
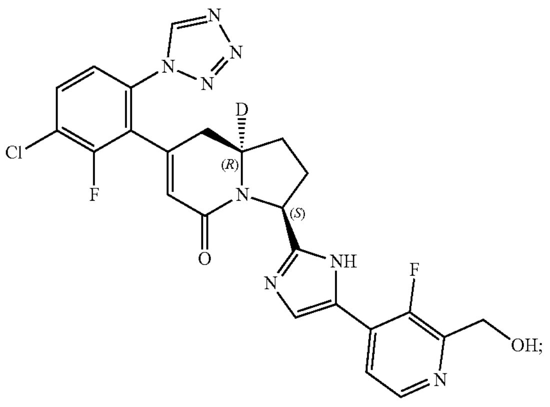
(d) compound of formula (I-E)
(I-E)
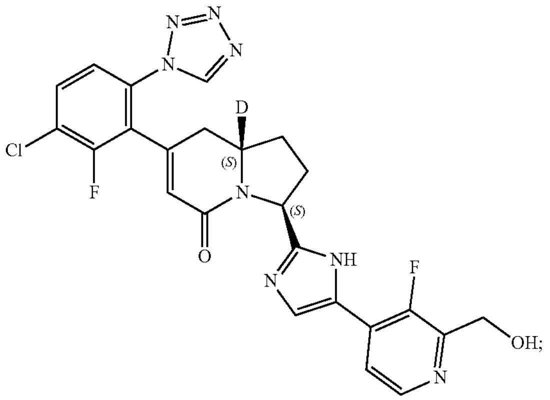
(e) a compound of formula (I-F)
(I-F)
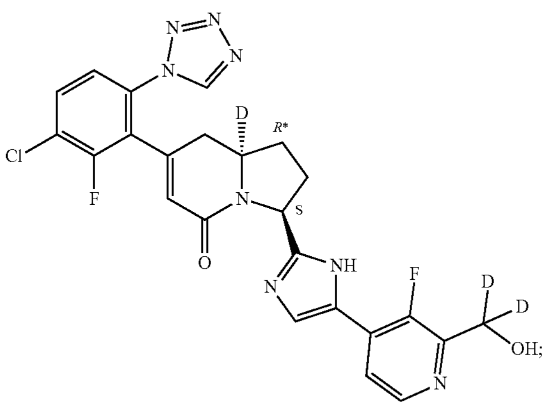
(f) compound of formula (I-G)
(I-G)
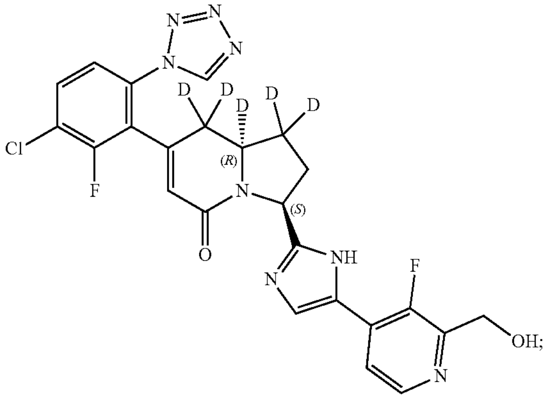
(h) compound of formula (I-H)
(I-H)
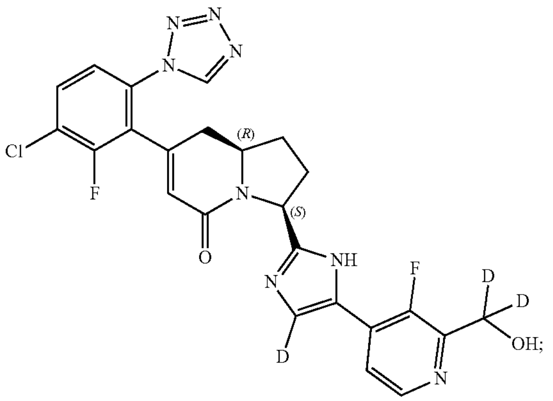
(j) compound of formula (I-J)
(I-J)
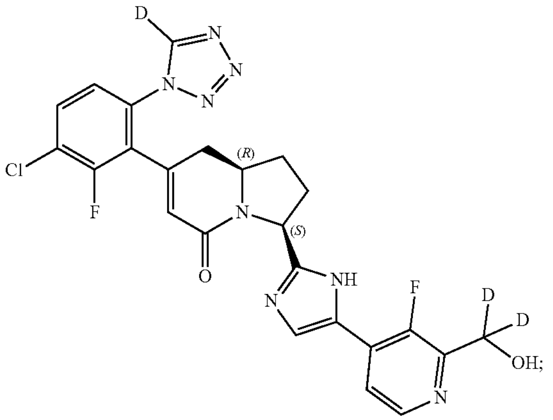

(k) compound of formula (I-K)

(I-K)

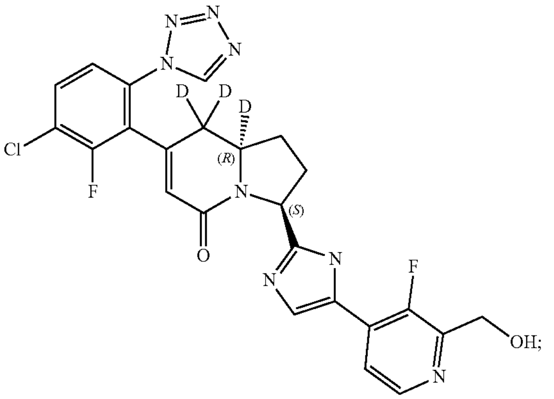

or a tautomer, stereoisomer, isotopologue or pharmaceutically acceptable salt or solvate thereof.

4. A compound of formula (II)

(II)

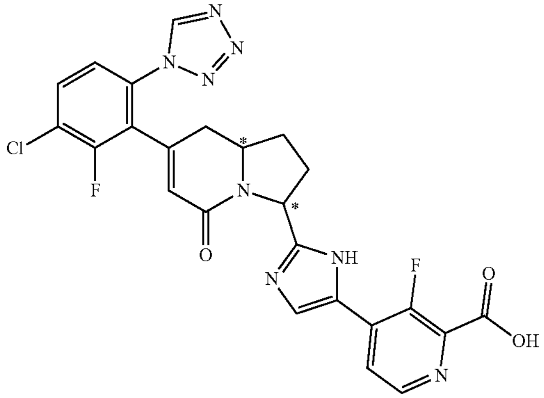

or a tautomer, stereoisomer, isotopologue, or pharmaceutically acceptable salt or solvate thereof.

5. The compound of claim 4 has formula (II-A)

(II-A)

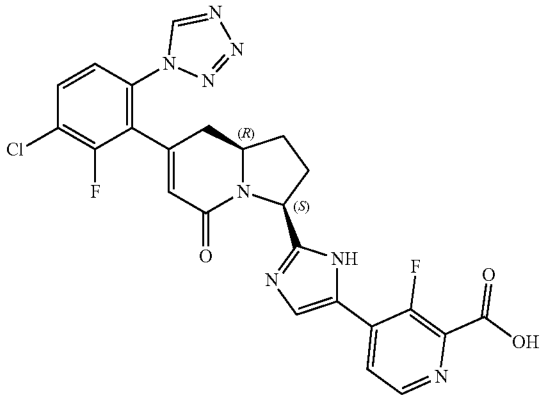

or a tautomer, stereoisomer, isotopologue, or pharmaceutically acceptable salt or solvate thereof.

6. A compound of formula (III)

(III)

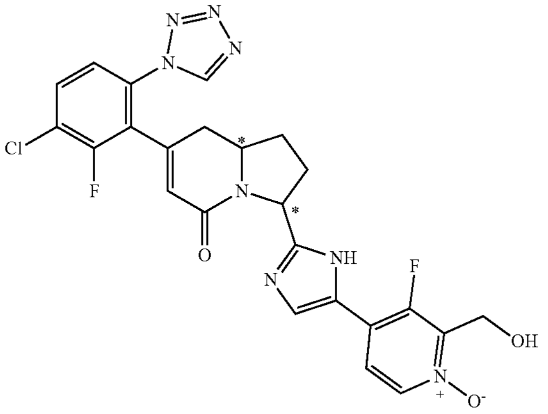

or a tautomer, stereoisomer, isotopologue, or pharmaceutically acceptable salt or solvate thereof.

7. The compound of claim 6 has the formula (III-A)

(III-A)

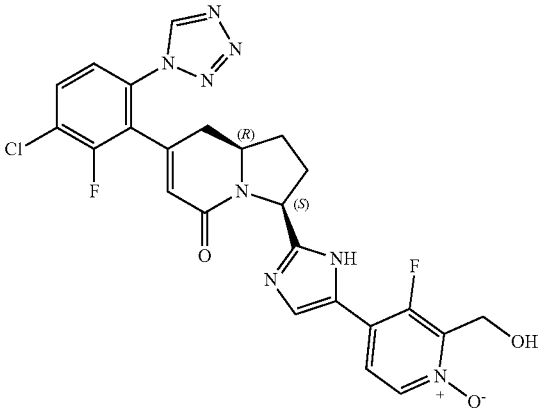

or a tautomer, stereoisomer, isotopologue, or pharmaceutically acceptable salt or solvate thereof.

8. A compound selected from the group consisting of (a) compound of formula (IV-A)

(IV-A)

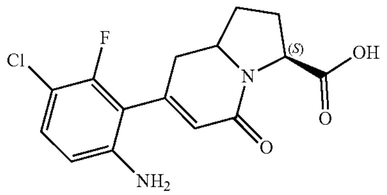

or stereoisomer, isotopologue, or salt thereof;

(b) compound of formula (V-A)

(V-A)

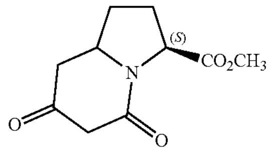

or stereoisomer, isotopologue, or salt thereof;

and (c) compound of formula (VI-A)

(VI-A)

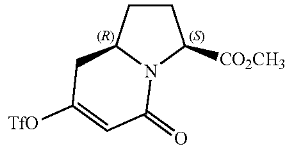

or stereoisomer, isotopologue, or salt thereof.

9. A pharmaceutical composition comprising a pharmaceutically acceptable carrier and a compound of claim 1.

10. A method for the treatment or prophylaxis of (a) a thromboembolic disorder; (b) an inflammatory disorder; or (c) a disease or condition in which plasma kallikrein activity is implicated, comprising administering to a subject in need thereof a therapeutically effective amount of the compound of claim 1.

11. The method of claim 10, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

12. The method of claim 10, wherein the thromboembolic disorder is selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from prosthetic valves or other implants, indwelling catheters, stents, cardiopulmonary bypass, hemodialysis, or other procedures in which blood is exposed to an artificial surface that promotes thrombosis.

13. The method of claim 10, wherein the thromboembolic disorder is selected from the group consisting of hereditary angioedema (HAE) and diabetic macular edema (DME).

14. The method of claim 10, wherein the inflammatory disorder is selected from the group consisting of sepsis, acute respiratory distress syndrome, and systemic inflammatory response syndrome.

15. The method of claim 10, wherein the disease or condition in which plasma kallikrein activity is implicated is selected from the group consisting of impaired visual acuity, diabetic retinopathy, diabetic macular edema, hereditary angioedema, diabetes, pancreatitis, nephropathy, cardiomyopathy, neuropathy, inflammatory bowel disease, arthritis, inflammation, septic shock, hypotension, cancer, adult respiratory distress syndrome, disseminated intravascular coagulation, and cardiopulmonary bypass surgery.

16. A pharmaceutical composition comprising a pharmaceutically acceptable carrier and a compound of claim 4.

17. A method for the treatment or prophylaxis of (a) a thromboembolic disorder; (b) an inflammatory disorder; or (c) a disease or condition in which plasma kallikrein activity is implicated, comprising administering to a subject in need thereof a therapeutically effective amount of the compound of claim 4.

18. A pharmaceutical composition comprising a pharmaceutically acceptable carrier and a compound of claim 6.

19. A method for the treatment or prophylaxis of (a) a thromboembolic disorder; (b) an inflammatory disorder; or (c) a disease or condition in which plasma kallikrein activity is implicated, comprising administering to a subject in need thereof a therapeutically effective amount of the compound of claim 6.

* * * * *